(12) United States Patent
Figueiredo et al.

(10) Patent No.: US 11,022,604 B2
(45) Date of Patent: *Jun. 1, 2021

(54) DOCK DERIVED COMPOUND AGAINST LAMININ RECEPTOR (37 LR) AND USES THEREOF

(71) Applicant: Purdue Research Foundation, West Lafayette, IN (US)

(72) Inventors: Marxa L. Figueiredo, Lafayette, IN (US); Charles Samuel Umbaugh, Heidelberg (DE); Herman O. Sintim, West Lafayette, IN (US); Adriana Diaz-Quinones, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/555,486

(22) Filed: Aug. 29, 2019

(65) Prior Publication Data

US 2020/0064334 A1     Feb. 27, 2020

Related U.S. Application Data

(63) Continuation-in-part of application No. 16/113,718, filed on Aug. 27, 2018, now Pat. No. 10,438,688.

(60) Provisional application No. 62/551,412, filed on Aug. 29, 2017.

(51) Int. Cl.
| | |
|---|---|
| *G01N 33/50* | (2006.01) |
| *G01N 33/574* | (2006.01) |
| *G16B 15/30* | (2019.01) |
| *G16C 20/60* | (2019.01) |
| *G16C 20/50* | (2019.01) |
| *A61K 31/497* | (2006.01) |

(52) U.S. Cl.
CPC ........ *G01N 33/5011* (2013.01); *A61K 31/497* (2013.01); *G01N 33/57434* (2013.01); *G16B 15/30* (2019.02); *G16C 20/50* (2019.02); *G16C 20/60* (2019.02)

(58) Field of Classification Search
CPC ............. A61K 31/497; G01N 33/5011; G01N 33/57434; G01N 2333/78; G01N 2800/105; G01N 2800/7095; G01N 33/582; G01N 33/6812; G16C 20/50; G16C 20/60; G16C 20/64; G16B 15/30; G16B 40/10
See application file for complete search history.

*Primary Examiner* — Jean P Cornet
(74) *Attorney, Agent, or Firm* — Purdue Research Foundation; Liang Zeng Yan

(57) ABSTRACT

An in silico screening method generated compounds that are against laminin receptor 37LR and their anti-cancer functions in prostate cancer cell lines are disclosed herein. A group of derivatives based on the hit compound from the in silico screening are synthesized and tested with improved $IC_{50}$ value that can have relevant clinical use for prostate cancer or osteoarthritis.

4 Claims, 32 Drawing Sheets

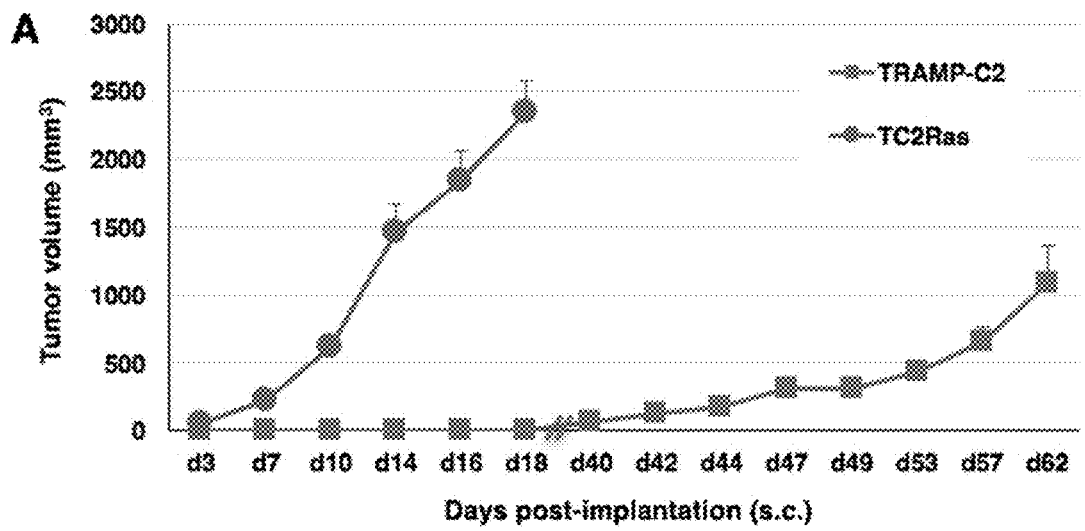
Fig. 14A
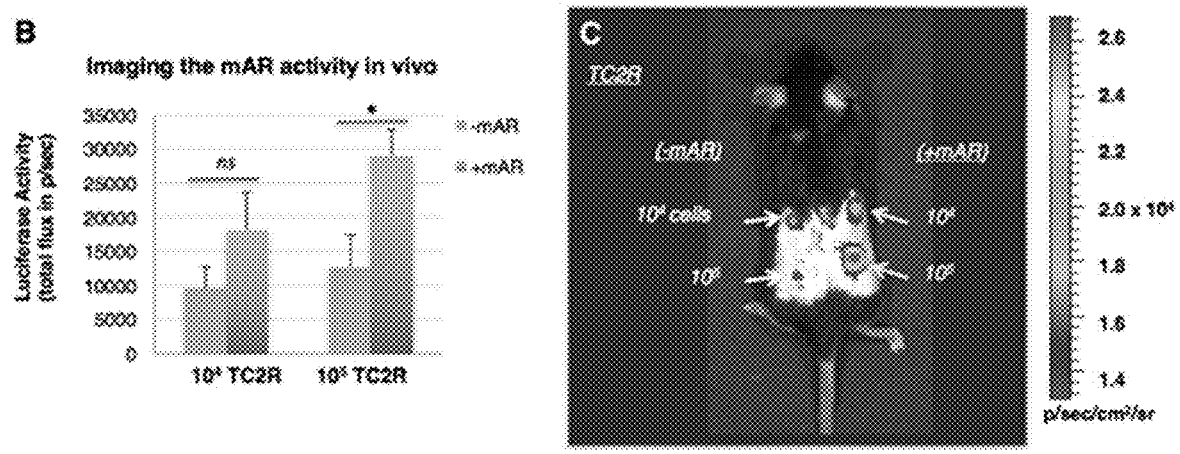
Fig. 14B
Fig. 14C

C3-HTS07944  II-03  II-05  II-09

DOCK DERIVED COMPOUND AGAINST LAMININ RECEPTOR (37 LR) AND USES THEREOF

CROSS REFERENCE

This application is a continuation-in-part for U.S. patent application Ser. No. 16/113,718, filed on Aug. 27, 2018, which claims the benefit of U.S. Provisional application 62/551,412, filed on Aug. 29, 2017. The contents each of which is expressly incorporated herein entirely.

FIELD OF INVENTION

This disclosure relates to novel method of validating in silico screen generated compounds that are against laminin receptor 37LR and their anti-cancer functions in prostate cancer cell lines.

Particularly, peptide G is utilized as a readout of hit compound interaction with 37LR, an interaction designed to mimic the 37LR with the pigment epithelium-derived factor (PEDF). This disclosure also relates to compounds identified by in silico method described herein that exert anti-inflammation and pro-chondrogenic effects and useful for osteoarthritis therapy. Derivatives with improved $EC_{50}$ values are provided based on the hit compound structure.

BACKGROUND

Laminin receptor (67 LR) is a 67 kDa protein derived from a 37 kDa precursor (37 LR). 37/67 LR is a strong clinical correlate for progression, aggression, and chemotherapeutic relapse of several cancers including breast, prostate, and colon. The ability of 37/67 LR to promote cancer cell aggressiveness is further increased by its ability to transduce physiochemical and mechanosensing signals in endothelial cells and modulate angiogenesis. Recently, it was demonstrated that 37/67 LR modulates the anti-angiogenic potential of the secreted glycoprotein pigment epithelium-derived factor (PEDF).

In silico (literally Latin for "in silicon", alluding to the mass use of silicon for semiconductor computer chips) is an expression used to mean "performed on computer or via computer simulation." The phrase was coined as an allusion to the Latin phrases in vivo, in vitro, and in situ, which are commonly used in biology and refer to experiments done in living organisms, outside of living organisms, and where they are found in nature, respectively.

In silico study in medicine is thought to have the potential to speed the rate of discovery while reducing the need for expensive lab work and clinical trials. One way to achieve this is by producing and screening drug candidates more effectively. In 2010, for example, using the protein docking algorithm EADock (see Protein-ligand docking), researchers found potential inhibitors to an enzyme associated with cancer activity in silico. Fifty percent of the molecules were later shown to be active inhibitors in vitro. This approach differs from use of expensive high-throughput screening (HTS) robotic labs to physically test thousands of diverse compounds a day often with an expected hit rate on the order of 1% or less with still fewer expected to be real leads following further testing.

Osteoarthritis affects over 27 million Americans age 25 and older and is a debilitating disease in which articular cartilage degradation leads to inflammation and pain in the joint. Medical management has not been very successful, as cartilage is avascular and has a difficult time regenerating itself. In joints, when PEDF (pigment epithelial derived factor) bind to laminin receptors (LR), it has anti-inflammatory, pro-chondrogenic and anti-angiogenic characteristics. However, the relatively large size and low stability of PEDF at 25° C. indicates that smaller, more stable molecules could be an alternative for therapeutic purposes. Thus, there is a need to identify smaller, more stable molecules for these therapeutic purposes.

SUMMARY OF THE INVENTION

This disclosure provides a method to identify hit compounds that interfere with cancer signaling triggered between Laminin receptor (67LR/37LR) and pigment epithelium derived factor (PEDF) binding. The method comprising the steps of:

docking a compound library against the 37LR crystal structure;

generating a plurality of compounds with predicted docking scores ranging from 9.3 Kcal/mol to -7.9 Kcal/mol;

selecting at least one compound with piperazine-like moieties from the plurality of compounds for in vitro testing to validate said at least one compound binds to 37LR and PEDF interaction region.

In some embodiment the aforementioned compound library is Maybridge Hitfinder™ library.

In some embodiment the aforementioned hit compound is identified as [4-(9h-fluoren-9-yl)piperazino](6-fluoro-4h-1,3-benzodioxin-8-yl)methanone or HTS07944SC in Maybridge Hitfinder™ library.

In some embodiment the aforementioned hit compound is identified from the group consisting of C1, C2, C4, C5 and C7.

In some embodiment the aforementioned in vitro testing comprising using the selected compound to treat cancer cell lines, evaluate anti-inflammatory effect, or pro-chondrogenic effect.

This disclosure provides an assay to validate a hypothesized compound to interfere with 37LR and PEDF binding. The assay comprising the steps of:

Obtaining fluorescence reading of intrinsic tryptophan in Peptide G in an assay buffer;

Providing the hypothesized compound to the buffer containing peptide G;

Observing any reduced intrinsic tryptophan florescence in a dose dependent manner of the hypothesized compound;

Determining EC50 of the hypothesized compound against peptide G.

In some embodiment the aforementioned hypothesized compound is derived from [4-(9h-fluoren-9-yl)piperazino](6-fluoro-4h-1,3-benzodioxin-8-yl)methanone or HTS07944SC in Maybridge Hitfinder™ library.

In some embodiment the aforementioned compound has an EC50 of about 16.1 μM.

This disclosure provides a method of treating prostate cancer by providing pharmaceutically effective amount of [4-(9h-fluoren-9-yl)piperazino](6-fluoro-4h-1,3-benzodioxin-8-yl)methanone and salt thereof to a patient.

In some embodiment the aforementioned anti-inflammatory effect is measured by downregulation of inflammatory genes selected from the group consisting of IL-8 and IL-1Beta in THP-1 monocytes following treatment of the selected compound.

In some embodiment the aforementioned pro-chondrogenic effect is measured by upregulation of cartilage specific genes selected from the group consisting of COL2A1, ACAN and SOX9 in ASC cell pellets following treatment of the selected compound.

This disclosure provides a method of treating osteoarthritis by administering pharmaceutically effective amount of compound selected from the group consisting of C1, C2, C3, C4, C5, C6 and C7 and salt thereof to a patient.

This disclosure further provides a group of C3 derivatives that has improved $IC_{50}$ value compared to C3 parent compound that was first identified from aforementioned method. As such, the claimed method can be used to identify and further deduct derivatives that has improved features for relevant clinical use.

These and other features, aspects and advantages of the present invention will become better understood with reference to the following figures, associated descriptions and claims.

BRIEF DESCRIPTION OF THE DRAWINGS

FIG. 2A, compound C1; FIG. 2B, compound C2; FIG. 2C, compound C3; FIG. 2D, compound C4; FIG. 2E, compound C5; FIG. 2F, compound C5; FIG. 2G, compound C7; FIG. 2H, DMSO.

FIGS. 14A-14C. TC2-Ras cell line characterization in vivo. The TC2-Ras cell line was generated by transduction of parental cells TRAMP-C2 with a lentivirus expressing a Ras gene at MOI=1. FIG. 14A Comparison of subcutaneous growth rate in vivo between parental cell line TRAMP-C2 ($10^6$) and TC2-Ras ($5 \times 10^5$) in 6-8 week old C57/BL6 male mice.

FIG. 14B mAR activity was assayed in vivo by bioluminescence imaging. An adenoviral vector containing an AR-responsive cassette expressing reporter gene luciferase was administered intravenously ($2 \times 10^8$ pfu/i.v.) 3 days following subcutaneous TC2-Ras cell implantation ($10^4$ or $10^5$, without mAR (-mAR control) or with mAR (+mAR) in C57/BL6 male mice. Mice were injected intraperitoneally with 150 mg/kg Luciferin (10-20 min incubation) followed by a 5 min signal acquisition using an IVIS100 imager (Caliper/PerkinElmer, Downers Grove, Ill.) and analyzed with LivingImage 3.1 software (Caliper/PerkinElmer). Statistics used a student's t-test to compare between mAR (−/+) groups for each cell concentration used. ns, $p>0.05$ (p=0.21); *, $p<0.05$ (p=0.023). FIG. 14C Representative image of a mouse that received either $10^4$ or $10^5$ TC2-Ras cells (−/+mAR) and received reporter adenovirus intravenously as described in (B). Color bar, p/sec/cm$^2$/sr.

(FIG. 16A) In silico drug design; (FIG. 16B) Unbiased or blind docking for compound 3 positions this compound at the interface of the Laminin Receptor at an interaction pocket containing His 169.

FIG. 20A IPA analyses indicated that LPS treatment generally upregulated cellular functions related to lipid metabolism (Akt/IkB), cell cycle, and cellular development (Rb1).

FIG. 20B IPA analyses indicated that C3 treatment generally upregulated cellular functions related to cellular assembly/maintenance, cell-cell signaling and tissue development, nucleic acid metabolism/RNA post translational modification and protein synthesis, and inflammatory response. Several molecules related to the EIF2 and eIF4, mTOR, PLC and integrin signaling pathways were altered. Predicted upstream regulators included MYCN, CST5, CD3 and MAPT. Causal networks suggested associations with S100A4, VEGF, SUMO-Ubc9 E2 and VIM.

FIG. 20C IPA analyses indicated that LPS followed by C3 treatment generally upregulated cellular functions related to free radical scavenging, RNA post-transcriptional modification, cell morphology and movement and cell-cell signaling and interaction. Several molecules related to the PLC, integrin, chemokine, geranylgeranyl disphophate biosynthesis, and CXCR4 signaling pathways were altered. Causal networks suggested associations or common mechanisms with quercetin (an anti-inflammatory plant polyphenol), CC-15 (DNA-PK/TOR kinase inhibitor and mTORC2 regulator), ATF (regulated by quercetin, Jun, and Erk), Harmine (regulates PCNA, MMP2, RUNX2, BMP2, FOS) and ARH (RhoGDP dissociation inhibitor). Predicted activation of molecules including PLN, MYB, and P53. Top disease processes associated with the proteomics patterns included rheumatic disease (arthritis), with 11 molecules altered including upregulation of ANXA1 (annexin A1), which is regulated by dexamethasone and belongs in the glucocorticoid receptor signaling pathway. Interestingly, this is the treatment that most mimics inflammation treated by C3.

FIG. 20D IPA analyses indicated that C3 followed by LPS treatment generally upregulated cellular functions related to cellular movement, gene expression, cell-cell signaling, cell death and survival and RNA pros-transcriptional modification. Causal networks analysis suggested associations or common mechanisms with RICTOR, isoflurophate, CH5126766 (coumarin derivative, RAF/ERK regulator), SUMO-ubc9 E2. Predicted upstream regulators included RICTOR, POLG, ARNT, T2, and guanidinopropionic acid. Predicted activation of molecules including a profile similar to butyric acid (which regulates MYC). Top diseases associated with the protein profile were infectious, inflammatory and immunological diseases and top physiological system development and function were related to connective tissue development and function, immune cell trafficking, immune response.

FIG. 28A, DMSO; FIG. 28B DBGII-3, 30 uM; FIG. 28C, EGCG, 30 uM; FIG. 28 D, DBGII-5, 30 uM, FIG. 28E, C3, 30 uM; FIG. 28 F, DBGII-9, 30 uM.

DETAILED DESCRIPTION

Figure 1:
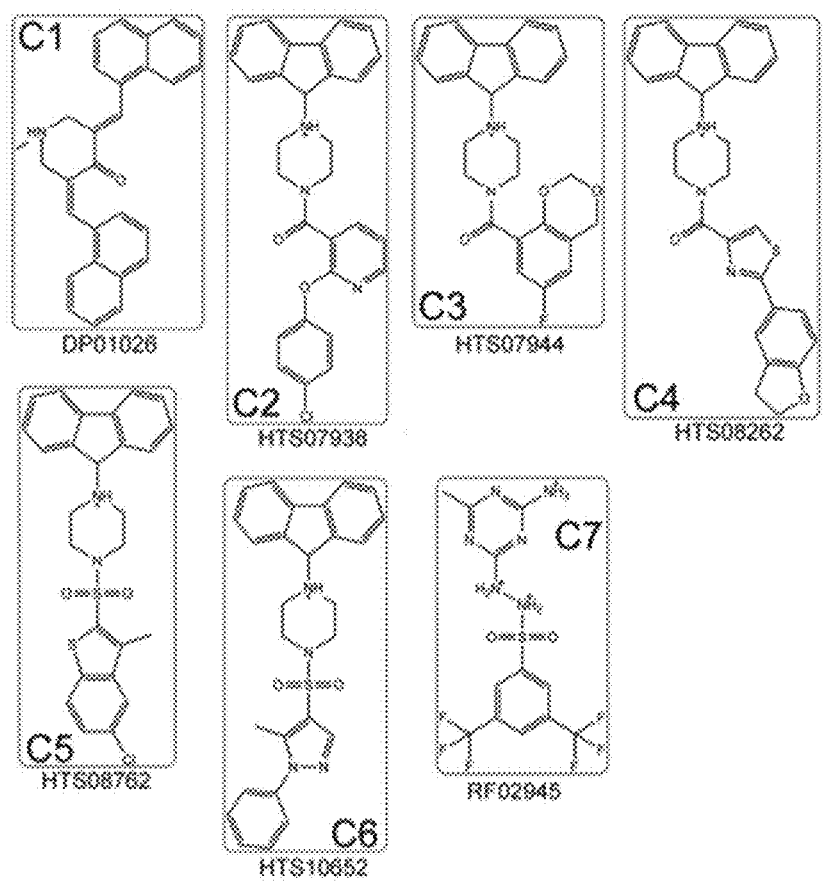
FIG. 1. Dock Derived Compounds Tested via in vitro screen. Dock derived compounds depicted with nicknames (C #) and Maybridge Hitfinder™ designations. Structures were generated using Chemdraw.
Figure 2A:
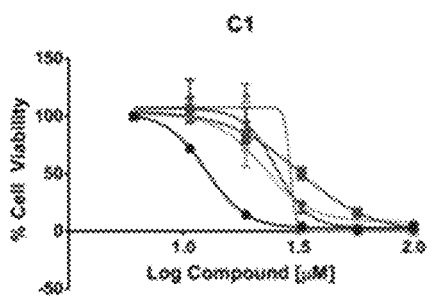
FIGS. 2A-2H. Dose response curves. Does response curves for cell lines treated with 6, 10.5, 18.6, 32.4, 57.5 and 100 μM of compound (log) for 96 hours using % cell viability derived from CCK-8 absorbance readings at 450 nm (n=3, mean±SEM). A DMSO equivalent control (n=2±SEM) was also included for each cell line tested: Ea.hy.926 endothelial cells (Endo), LNCaP androgen dependent metastatic prostate cancer cells, TC2-Ras mouse prostate cancer cells, PC-3 androgen independent metastatic prostate cancer cells, and SH-SY5Y neruoblastoma cells. Curves were fit using GraphPad Prism as described in the methods.
Figure 2B:
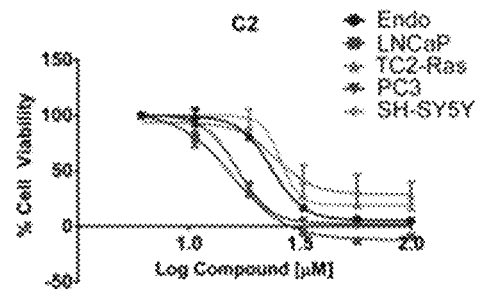
Figure 2C:
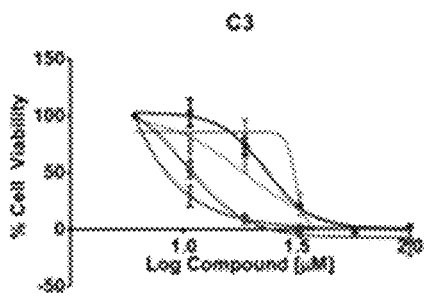
Figure 2D:
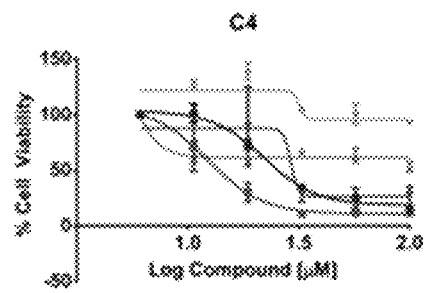
Figure 2E:
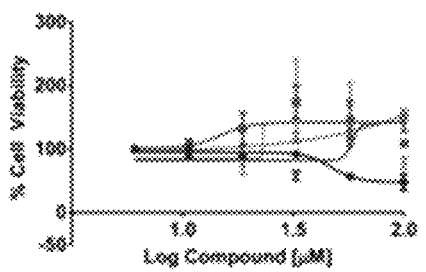
Figure 2F:
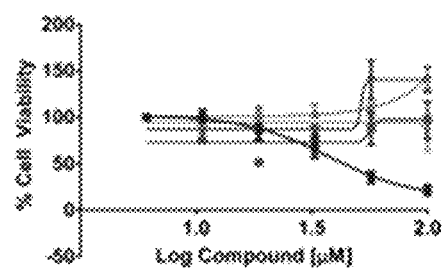
Figure 2G:
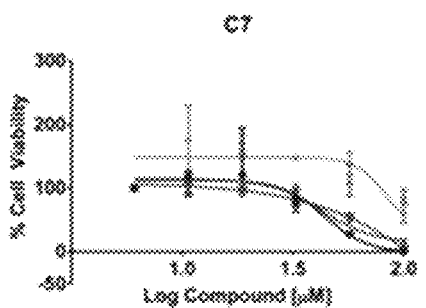
Figure 2H:
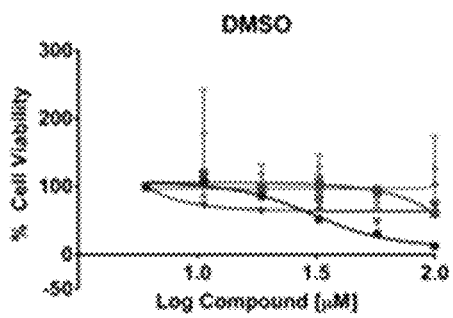

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

As used herein, LR refers to Laminin Receptor. PEDF refers to pigment epithelium derived factor. VEGF refers to vascular endothelial growth factor. THBS thrombospondin-1 refers to matrix metalloproteinase (MMP)-2 and -9. Vascular endothelial growth factor receptor 2 is described as VEGFR2, transforming growth factor beta is described as TGFB, tissue inhibitor of metalloproteinase 2 is described as TIMP2, caspase-3 is referred to CASP3, bcl-2-associated x protein is referred to as BAX, Rho guanine nucleotide exchange factor 7 is referred to as PIXB and PAK1 (P21 (RAC1) Activated Kinase 1). DMSO, dimethyl sulfoxide, CCK-8, cell counting assay-8, ATCC, American Type Culture Collection, NCI, National Cancer Institute.

Laminin receptor (67 LR) is a 67 kDa protein derived from a 37 kDa precursor protein (37 LR). The derivation process most likely involves post-translational modification of 37 LR by acylation or other lysine-directed conjugations. Because the two species are interrelated, Laminin Receptor at large is referred to as 37/67 LR. 37/67 LR is a member of the non-integrin receptor family. 37 LR is encoded by the gene RPSA, facilitates ribosome assembly, and is distributed to nuclear and cytoplasmic compartments of the cell. Using laminin sepharose columns and/or tumor cells, several groups isolated and identified 67 LR. 37/67 LR, perhaps owing to its laminin binding capacity, is frequently found at the plasma membrane. Both 37 LR and 67 LR are able to bind laminin and laminin derived peptides, molecules intimately involved in normal cell to matrix contact and pathologically associated with cancer progression, metastasis, and invasion.

37/67 LR is regarded as a strong clinical correlate for progression, aggression, and chemotherapeutic relapse of several cancers including breast, prostate, and colon. The C-terminus of 37/67 LR has been suggested to increase viability and enhance survival of breast cancer cells. In a lung cancer model, endogenous 37 LR expression levels were correlated with metastatic status, and overexpression of 37 LR enabled lung cancer cells to establish lung metastases in vivo. Upregulation of 67 LR also has been associated with melanocyte tumor development, and invasiveness of ovarian and endometrial cancer. Downregulation of 37/67 LR by RNA interference (RNAi) inhibits cell migration and invasiveness, reduces cell binding to laminin and enhances the apoptotic response of colon cancer cells to doxorubicin, and inhibits hepatoma cell viability.

The ability of 37/67 LR to promote cancer cell aggressiveness is further increased by the ability of 37/67 LR to transduce physiochemical and mechanosensing signals in endothelial cells and modulate angiogenesis—a key component of the tumor/microenvironment interaction. Recently, it was demonstrated that 37/67 LR modulates the anti-angiogenic potential of the secreted glycoprotein pigment epithelium-derived factor (PEDF). Originally discovered as a regulator of retinal and ocular health, PEDF is a non-inhibitory member of the serine protease inhibitor family that has been regarded as a novel and potent inhibitor of angiogenesis. Administration or expression of full length PEDF or peptides derived from PEDF markedly reduces vascularization and endothelial cell viability concomitant with a decrease in endogenous vascular endothelial growth factor (VEGF).

Outside of angiogenic models, imbalance of endogenous PEDF has been observed in many cancers. Restoration of PEDF balance is a desirable therapeutic outcome and has been achieved largely via gene delivery regimens or through administration of PEDF peptides. Additionally, 37/67 LR has been identified as an emerging and promising target for pharmacological intervention in cancer progression. Therapeutic targeting to 37/67 LR has focused on the interaction between 37/67 LR and the green tea natural product, epigallocatechin gallate (EGCG). Acting through 37/67 LR, EGCG elicits anti-proliferative and anti-cancer effects in several cell lines. Of high relevance to our study, a recent virtual based screen of National Cancer Institute (NCI) compounds against the laminin binding domain of 37/67 LR isolated several active chemicals with the ability to inhibit cell migration and binding to laminin at low micromolar doses.

Restoration of PEDF balance is a desirable therapeutic outcome, and we sought to identify a small molecule that could recapitulate known signaling properties of PEDF but without the additional complications of peptide formulation or gene delivery safety validation. We used an in silico drug discovery approach to target the interaction interface between PEDF and 37LR. Following cell based counter screening and binding validation, we characterized a hit compound's anti-viability, activation of PEDF signaling-related genes, anti-wound healing, and anti-cancer signaling properties. This hit compound has potential for future development as a lead compound for treating tumor growth and inhibiting angiogenesis.

Anti-Cancer

Briefly, we used an in silico drug discovery approach to target the interaction interface between PEDF and 37LR. Following cell based counter screening and binding validation, we characterized a hit compound's anti-viability, activation of PEDF signaling-related genes, anti-wound healing, and anti-cancer signaling properties. This hit compound has potential for future development as a lead compound for treating tumor growth and inhibiting angiogenesis.

We have demonstrated that phenotypic cell survival assays can be effectively coupled to virtual based screening methods to identify novel compounds that alter and inhibit castration resistant prostate cancer cell (PC-3) growth in the context of the PEDF/LR interaction interface. It has been shown that in silico approaches to drug discovery are a useful tool for cancer biologists and facilitate hypothesis driven research avenues without the expensive startup costs associated with biochemical drug discovery that may be underutilized on compounds that do not display desirable anti-tumor properties in downstream in vitro and in vivo functional assays. Moreover, in silico approaches are becoming more accessible and user friendly and the datasets generated can be explored and readily refined with input from expert medicinal chemists.

Figure 21:
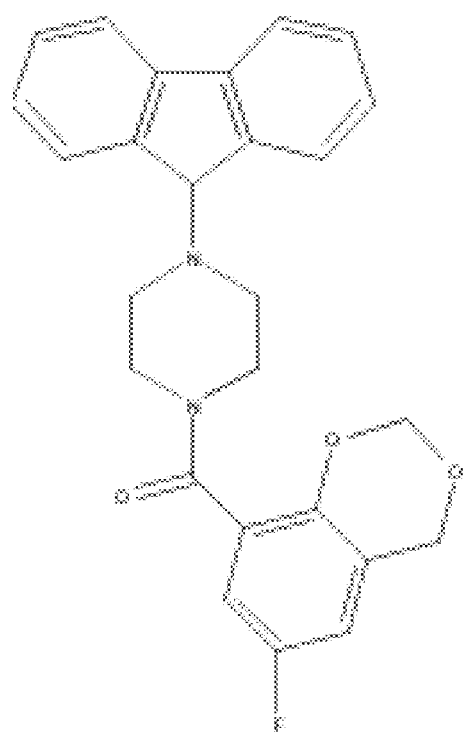
FIG. 21. Structure of C3.

We have identified HTS07944, or C3, with the structure in FIG. 21, was able to inhibit cell viability at ~1 µM and inhibited cellular proliferation at 10 µM in PC3 cells. Additionally, a 50 µM dose was sufficient to inhibit cell migration in a wound healing assay. Taken together, C3 had a clear effect on PC-3 cell viability and function. C3 is a piperazine analogue, a class of compounds well characterized for their diverse uses in medicinal chemistry ranging from neuropsychiatric applications, tuberculosis treatment, anti-angiogenic therapy, to cancer. Our in silico structural predictions suggest that C3 binds to 37 LR in the laminin binding pocket and that this binding may be facilitated by a hydrogen bond between His 169 and the benzodioxin moiety of the compound. This hypothesis is supported by recent work highlighting a class of compounds from (or derived from) the NCI Diversity Set that were predicted to interact with the same general binding pocket, termed peptide G, of 37LR (161 to 180 aa), albeit through hydrogen bonding with Gly 172 and a hydrophobic interaction with His 169. Of relevance, this binding region falls squarely within the known interaction region for PEDF and 37 LR (120 to 210 aa).

Our in silico predictions were validated by an intrinsic tryptophan fluorescence assay employing Peptide G (161 to 180 aa), whereby titration of C3 decreased intrinsic tryptophan fluorescence in a dose dependent manner with an EC50 of 16.1 µM while having no appreciable effect on tryptophan fluorescence in a same sequence scrambled peptide (Scramble G), suggesting that C3 binds specifically to the intrinsic fold of Peptide G. Taken together with the evidence that C3's potency (reduction in cell viability) is correlated with endogenous 37 LR levels, we suggest that C3 interacts with 37 LR.

Figure 13:
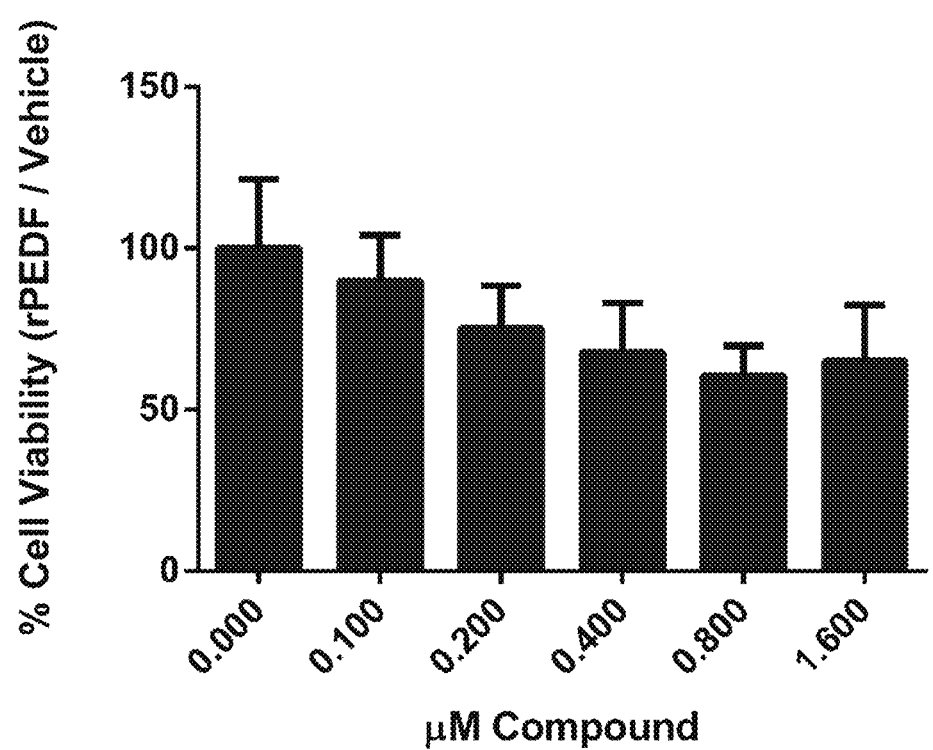
FIG. 13. PC-3 Cell Viability Response To Recombinant PEDF PC-3 cells were treated with 0.1 to 0.6 μM rPEDF for 48 hours and cell viability was measured using the CCK-8 assay (n=3, mean±SEM). A one-way ANOVA was used for statistical analysis (n.s. p=0.11) however the linear trend was significant (post test for linear trend, p<0.05).
Figure 15:
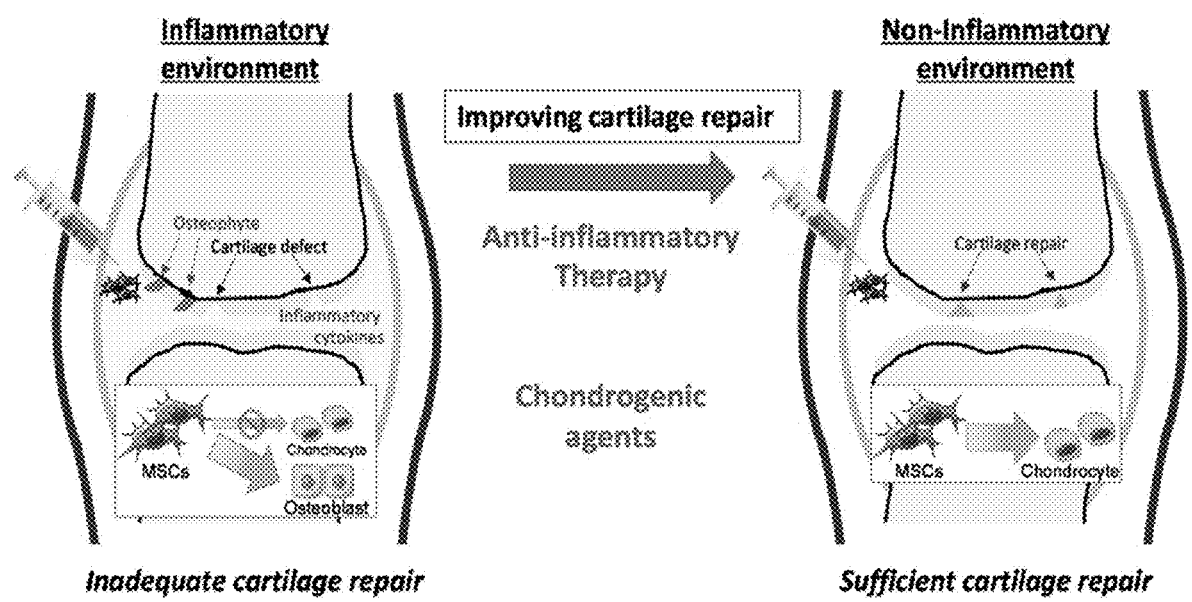
FIG. 15. The challenges underlying endogenous joint repair in Osteoarthritis (OA). A compound that could promote both chondrogenesis by ASC and anti-inflammatory responses could augment cartilage repair. ASC may reside already in the fat pads surrounding the joint.
Figure 16A:
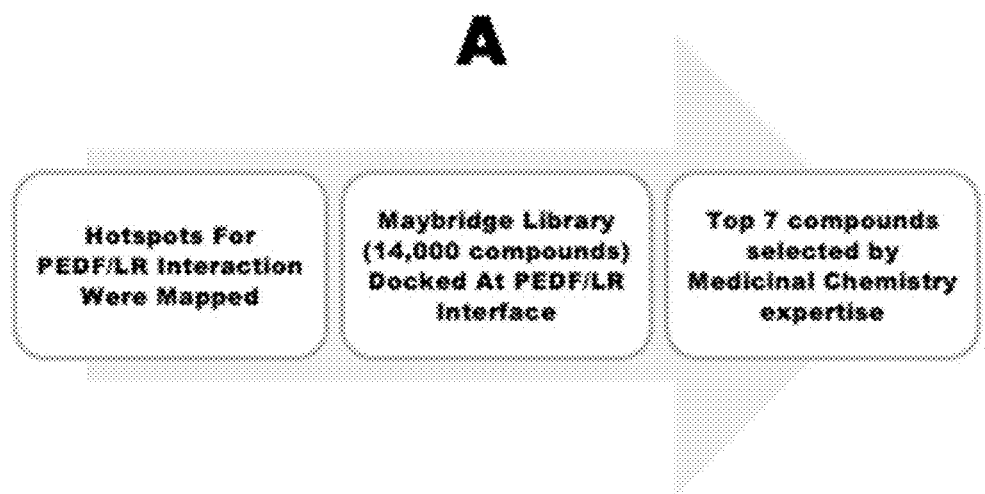
FIGS. 16A-16B In silico drug design and unbiased docking.
Figure 16B:
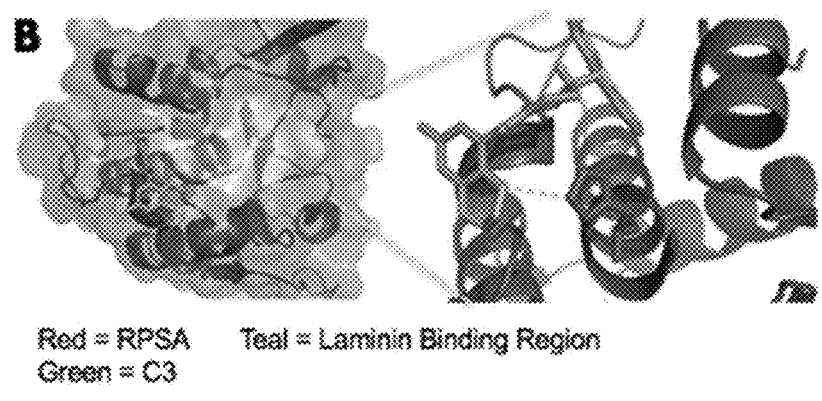

Our lab and others have demonstrated that PEDF's potent antiangiogenic potential can be leveraged to treat both the tumor and the surrounding angiogenic microenvironment. While these gene delivery driven therapies show promise, we sought to identify small molecules that could recapitulate known signaling properties of PEDF but without the additional complications of peptide formulation, delivery of a recombinant protein, or gene delivery safety validation. In our hands, we were unable to demonstrate a significant dose/response relationship between survival of PC-3 cells and increasing doses of recombinant PEDF (FIG. 13). This was not surprising to us as the anti-cancer/anti-angiogenic PEDF peptide p18 does not markedly alter PC-3 cell viability while still maintaining an in vivo potency, however, the result could also be due to variability inherent to PEDF preparations.

We investigated the expression of a panel of genes implicated in either proposed mechanisms for PEDF function or for 37 LR function. Treatment of PC-3 cells with 50 µM C3 for 48 hours markedly reduced transcription of VEGFR2 (>-15 fold change or FC), a known effect of PEDF treatment, previously shown to be mediated through a gamma secretase dependent proteolysis of VEGFR2. A compensatory upregulation of VEGF was observed (~4 FC) but with no concomitant upregulation of HIF1A. The known upregulation of MMP2 and MMP9 in response to PEDF treatment was also observed. However, where recombinant or endogenous full length PEDF protein is a substrate for proteolytic degradation (71) by MMP2 or MMP9, a small molecule that mimics PEDF should avoid such degradation, as the specific proteolytic sites are not present in C3. C3 also upregulated thrombospondin-1 (THBS1, >10 FC). THBS1, much like PEDF, has been implicated as a protein with dual anti-tumor and anti-angiogenic activity (72). Additionally, the two proteins work in concert to downregulate angiogenesis (41). Consistent with our finding that C3 did not alter cell viability via a caspase 3/7 dependent mechanism, we did not observe a significant upregulation of caspase 3 (CASP3) or BAX at the mRNA level. Overall, these results suggest that C3 could mimic PEDF responsive-genes or pathways in a manner consistent with an anti-angiogenic function.

While VEGF receptors have been demonstrated to be expressed by PC-3 cells and to facilitate an autocrine VEGF mediated signaling loop that may promote tumor growth, we wanted to orthogonally validate the C3-induced PEDF associated gene changes by testing the compound in an endothelial cell tube formation assay. 1, 10, and 50 µM doses of C3 were able to completely or nearly completely inhibit endothelial tube formation, suggesting that C3's observed effects on angiogenesis-associated genes correlates with functional inhibition of angiogenesis.

Because the functions of 37 LR and PEDF are diverse and the mechanisms underlying PEDF's anti-tumor properties are still unclear (in contrast with its well-characterized role in anti-angiogenesis), we employed an unbiased label-free quantitative mass spectrometry approach to determine the types and levels of proteins modulated in PC-3 cells following treatment with a moderate dose of C3 (10 µM), chosen from the BrdU and t-scratch functional assays. Our objective was to gain insight into the potential mechanisms of activity of C3 in PC-3 cells through proteomic analyses. The most downregulated protein (RPL29, log 2FC −5.2), is a member of the 60S ribosome which indicates that C3 may be acting to modify translational pathways, consistent with a hypothesis that C3 is exerting anti-tumor effects through 37LR. Moreover, RPL29 binds and interacts with the extracellular matrix and knockdown of RPL29 has been reported to induce colon cancer cell differentiation. siRNA knockdown of RPL29 in an aortic model of angiogenesis resulted in significantly decreased microvessel sprouting in response to VEGF stimulation. These alterations might suggest a role for C3 in the regulation of angiogenesis through impacting regulation of translation.

Consistent with our observations that C3 inhibited cell viability, cell proliferation, and cell migration, we observed a downregulation of several MCM family proteins, MCM-3, MCM-4, and MCM-6. MCM proteins serve as a checkpoint for the S phase of the cell cycle and are considered diagnostic markers for poor prognosis in a variety of cancers. Further evidence for disruption of DNA synthesis, as evidenced by C3's ability to inhibit BrdU incorporation, was confirmed by down regulation of the E2 ligases UBE2S and UBE2C, proteins required for mitotic exit. UBE2C is considered a potent oncogene and is highly upregulated in castration-resistant prostate cancer. The mitotic/centromere associated protein WDHD1 was also downregulated. C3 decreased levels of CDA, cytidine deaminase, an enzyme well characterized for its ability to decrease the efficacy of gemcitabine chemotherapy, suggesting that C3 could be explored in the future as a part of a combinatorial chemotherapeutic regimen. We also observed downregulation of KPNA2, an importin and a key marker of poor disease prognosis and metastatic prostate cancer aggressiveness. In combination, these changes suggest a role for C3 in regulating cancer cell aggressiveness through regulation of mitotic/cell division machinery function.

C3 also upregulated GPX1, glutathione peroxidase 1, a response protein that facilitates sequestration of cytotoxic oxidants and a described putative tumor suppressor with loss of function in PC-3 cells. Upregulation of FTH1, ferritin heavy chain 1, may be a compensatory response to C3's effects on angiogenic pathways, as FTH1 can reestablish tumor angiogenesis. Upregulation of ASNS, asparagine synthetase, may also be a compensatory response, as ASNS is upregulated under cellular stress conditions including the unfolded protein response or endoplasmic reticulum stress. Consistent with the hypothesis that C3 may disrupt translation events, we noted an upregulation of ICT 1, a peptidyl tRNA hydrolase that responds to mitoribosomal arrest, but the significance of this finding is unknown since ICT1 may be implicated in cancer progression.

While the majority of the proteins detected via mass spectrometry appeared to support the hypothesis that the net effect of C3 on PC-3 cells was an activation of anti-tumor signaling, we further analyzed the dataset using ingenuity pathway analysis to assess the effects of C3 en masse. Pathway analysis indicated a predicted activation of P53, a predicted inactivation of MYC, and suggested that the signature of proteins altered by C3 was consistent with the known effects of doxorubicin. Both activation of P53 and inactivation of MYC involved the MCM family of proteins detected in this study as well as UBE2S and/or UBE2C. We chose to orthogonally validate our proteomic data set and IPA interpretations using a luciferase reporter system for MYC binding elements, reasoning that PC-3 cells are functionally considered P53 null and that advanced prostate cancers frequently overexpress c-myc. 50 μM C3 was able to significantly decrease c-myc binding activity in a reporter assay, validating our proteomic results.

Taken together, C3's phenotypic effects on PC-3 cells are a dual combination of anti-tumor/anti-growth pathway and anti-angiogenic pathway activation, of which there is some overlap. The dual anti-tumor/anti-angiogenesis activity is consistent with the described effects of PEDF reported by us and others. Given that C3 inhibits BrdU uptake, downregulates MCM family proteins, and downregulates c-myc activity, we propose that C3 is a bona fide anti-proliferative agent that warrants further pre-clinical investigation in the realm of prostate cancer drug discovery and development, and that 37 LR continues to be a promising avenue for targeted therapeutic intervention. We believe future efforts in the 37 LR targeting field would benefit from development of a high throughput binding assay and we aim to test both C3 and derivatives of C3 in such a format, perhaps employing a tryptophan fluorescence assay using Peptide G. A peptide based high-throughput binding assay is economical and facilitates true structure activity relationships to be derived between Peptide G/37 LR and lead iterations of C3 or other 37 LR active compounds. Moreover, we plan to test the efficacy of C3 in a mouse model of prostate cancer prior to lead optimization.

Anti-Inflammatory and Osteoarthritis Therapy

We developed seven small compounds that bind to the PEDF docking zone at the LR, with the goal to mimic the effects of PEDF. In order to test our drugs in a pro-inflammatory environment, THP-1 macrophage cultures were stimulated with lipopolysaccharide. Quantitative real-time polymerase chain reaction (qPCR) was used to assess up- and down-regulation of inflammatory genes, including IL-1β. Compound 3 (C3) appears to be the best PEDF mimic as it reduced IL-1f3 expression by ~8-fold. A cell pellet chondrogenesis assay using adipose-derived stem cells (ASC) was used to examine the effect of compounds on upregulating cartilage-specific genes at day 8 of differentiation. In the future, ASC pellets will be harvested at differentiation days 7, 14 and 21 to determine the timing of cartilage-specific gene expression following treatment with the small compounds. From our results, C3 appears to be the most promising drug for future development since it is able to reduce expression of pro-inflammatory gene IL-1β and promote ASC to express cartilage-specific genes. Other compounds such as C1, C5, C6, and C7 also hold promise for anti-inflammatory activity and cartilage-promoting ability.

Results from the THP-1 macrophage cell culture experiment indicate that no compounds were able to significantly downregulate IL-8. However, C3 did not upregulate IL-8 to the extent of Kartogenin, the other available small molecule for OA therapy, which is strictly chondrogenic [4] and not anti-inflammatory. IL1β was downregulated by three compounds, with C3 averaging an 8-fold reduction in transcription of the gene. As IL1β is the major mediator of inflammation in the knee, we deem these compounds, and in particular C3, very promising as an anti-inflammatory therapy.

By using luciferase reporter plasmids containing response elements that bind the transcription factors that regulate IL1β levels, we can estimate that GR and AP-1 may be working together to transrepress IL1β′ following C3 treatment. Also, it appears as if STAT3, an activator of IL1β, also is downregulated by C3 suggesting that more than one mechanism is at work by which IL1β levels are decreased by our compounds of interest.

As cartilage is degraded in the joint, leading to pain and inflammation, it becomes imperative to treat and cure OA with a drug which is pro-chondrogenic. It is important for C3 to encourage ASC to differentiate into chondrocytes, yet not too far as to become hypertrophic chondrocytes which eventually mature to bone. We show that C3, as well as other compounds from our in silico screen, can upregulate the expression of early cartilage-specific genes, which suggest ASC began to differentiate into chondrocyte-like precursors. This experiment in the future will have ASC pellets harvested at days 7, 14, and 21 to determine the genes being expressed at different time points and whether hypertrophic genes are expressed or not.

EXAMPLES

Materials and Methods for Anti-Cancer Treatment
In Silico Screening Ligand & Protein Preparation. The 2.15 Å crystal structure of 37 LR (PDB ID: 3BCH) (92) was cleaned and prepared using AutoDock Vina and Autodock-Tools (93). The Maybridge HitFinder™ version 10 library comprising 14,400 drug-like compounds was accessed using "Docking At UTMB" (now "Docking At TACC"), a virtual screening drug discovery web portal that performs automated docking of pre-cleaned .pdbqt libraries against an input structure (65). The top 24 compounds (−9.3 kcal/mol to −7.9 kcal/mol) were recorded and evaluated for downstream applications.

Refinement of In Silico Hits. The top 24 compounds as assessed by predicted binding scores via docking were evaluated for drug-likeness by a medicinal chemist. 7 final compounds were ordered and synthesized from Maybridge via ThermoFisher Scientific. Compounds were resuspended in 100% dimethylsulfoxide (DMSO, Sigma Aldrich) to 10 mM, vigorously mixed, inspected for absence of precipitates, and stored at −20° C. in amber tubes until use. Maybridge compound names, clogp, and nicknames are provided in Table 1.

Cell Culture Conditions. All cell lines were routinely passaged and maintained at 37° C. with 5% $CO_2$. EA.hy926 endothelial cells (Endo, ATCC CRL-2922) were cultured in 10% fetal bovine serum (FBS, ThermoFisher) with 1× Dulbecco's Modified Eagle Medium (DMEM, Corning) and 1× antibiotic-antimycotic (anti-anti, 100 units/mL penicillin, 100 μg/mL streptomycin, and 0.25 μg/mL amphotericin B; Gibco). LNCaP prostate tumor cells (ATCC CRL-1740) were cultured in 10% FBS (ATCC) with 1×RPMI-1640 (Corning) and 1× anti-anti. PC-3 prostate tumor cells (ATCC CRL-1435) were cultured in 10% FBS (ThermoFisher) with 1×RPMI-1640 and 1× anti-anti. SH-SY5Y neuroblastoma cells (gift from Dr. Rakez Kayed) were cultured in 10% FBS (ThermoFisher) with 1×Opti-MEM I (Gibco) and 1× anti-anti. Mouse TRAMP-C2 cells were obtained from ATCC and maintained in Dulbecco's Modified Eagle's Medium Nutrient Mixture F-12 (DMEM:F12; Corning) with 10% FBS (ThermoFisher) and 1× anti-anti. TRAMP-C2 cells (94) were transduced with a lentivirus expressing activated H-rasG12V (Lv-Hras) (95) at a multiplicity of infection of 1 and a lentivirus expressing mouse androgen receptor (mAR) at a multiplicity of infection of 1, resulting in TC2-Ras. Their characterization is shown in FIGS. 14A-14C. Cells were regularly passaged by trypsinization (0.05% (v/v) trypsin, 0.53 mM EDTA) or lifted using 20 mM EDTA (Sigma) in 1×DPBS.

Cell Viability Screen. PC-3, Endo, TC2-Ras, SH-SY5Y, and LNCaP cells were seeded in 96-well plates at 1,500 cells per well using the Scepter cell counter (EMD Millipore). Cells were continuously incubated with compound using a 6-point dose curve: 100, 57.5, 32.4, 18.6, 10.5, and 6.0 μM in their respective complete media. Cell viability was measured by using the cell counting kit-8 (CCK-8, Dojindo). CCK-8 uses a highly water soluble tetrazolium salt, WST-8, which is reduced by dehydrogenase in cells to yield a yellow formazan dye, which is directly proportional to the number of living cells. CCK-8 absorbance was measured at 450 nm using a GloMax Multimode Reader (Promega). Readings were performed the day after seeding to normalize for variations in cell seeding and after 96 hours of compound treatment. After each reading, CCK-8 media was removed and replaced with media containing compound as described previously. A serial dilution using vehicle, dimethyl sulfoxide (DMSO), for each cell line was performed in parallel along with inclusion of a media only negative control and a cell only positive control.

Cell Viability Screen Statistics. As described previously, an initial baseline CCK-8 reading was performed at 24 hours post seeding to correct for variations in seeding density. First, 450 nm values for each well were subtracted from media only readings to correct for baseline absorbance. Then, the 96 hour readings were normalized to their respective 24 hour readings to control for seeding variation. Percent cell viability was obtained by dividing corrected 96 hour values by untreated cell only control readings, which were normalized to 100% on the y-axis. Average compound values were reported in triplicate and standard error of the mean (SEM) calculated per plate, with DMSO values reported in duplicate with SEM per plate. Since the compounds were designed to mimic PEDF, an inhibitor of 37 LR, we postulated that we could calculate $IC_{50}$ values for each compound. $IC_{50}$ represent the concentration of an inhibitor where the response is reduced by half. ICsos were calculated using a nonlinear fit (log(inhibitor) vs. response—variable slope (four parameters)) in GraphPad Prism 6.

Endogenous 37 LR Expression Levels In Screened Cell Lines. PC-3, Endo, TC2-Ras, SH-SY5Y, and LNCAP cells were grown in 100 mm plates in complete media and lifted at ~90% confluency using 20 mM EDTA in 1×DPBS. Cells were pelleted, media was aspirated, and pellets were frozen at −80° C. until required for analysis. Total protein was isolated using 1×RIPA buffer (Thermo Scientific) containing 1×Halt Protease Inhibitor (Thermo Scientific), 5 mM EDTA, and Phosphatase Inhibitor Cocktails 2 and 3 (Sigma Aldrich). Cells were lysed passively on ice for thirty minutes, sheared using a tuberculin syringe (BD) and supernatant was separated from cellular debris after a 30 minute 14,000 rpm spin at 4° C. Protein concentration was determined using the BCA assay (Thermo Scientific). 50 ag of protein was loaded onto a Bolt 4-12% Bis-Tris Plus gel (Life Technologies) and electrophoresed for 30 minutes at 200V. Proteins were transferred onto nitrocellulose using the iBlot2 system (Life Technologies). The blot was blocked for 1 hour at room temperature using 5% BSA in 1×PBS with 0.1% Tween-20 (Acros). 37 LR was probed using a rabbit polyclonal (Bioss, bs-0900R, 1:250) and beta actin was probed using a mouse monoclonal (ThermoFisher, MA5-15739, 1:5000). Goat anti-rabbit IgG secondary (Licor, 925-68021, 1:15,000) and goat anti-mouse IgG secondary (Licor, 925-32210, 1:15,000) were used to detect primary antibody and signal was detected using the Licor Odyssey CLx. Image Studio Lite (Licor, ver. 5.2) was used to quantify pixel intensity.

Redocking And Structural Validation Of Hit Compound C3. Redocking of C3 was manually performed using Autodock Vina and AutodockTools with a 100 Å box with a center of (13.8, 52.9, 39.2 (x,y,z)) and an exhaustiveness of 1000. Pymol was used for visualization. C3 structure was confirmed using 1H-NMR, 13C-NMR, and HPLC-MS-MS (data not shown).

Intrinsic Tryptophan Fluorescence Binding Assay. A 20-mer peptide encompassing the 37 LR binding site for laminin (aa 161-180) (61) was synthesized alongside a same-sequence 20-mer scramble peptide: IPCNNKGAHSVGLMWWM-LAR (Peptide G), GGKMLWISVANNRLCMAPWH (Scramble G), at 98% percent purity (United Biosystems). Dry peptides (~5 mg) were resuspended in 50 μL of DMSO and diluted dropwise with 450 μL of $dH_2O$. Final peptide concentration was determined via A280 using a Nanodrop by accounting for the molar absorptivity of the two tryptophans present in the peptides. For the binding assay, C3 was serially diluted from 100 μM to 0.1 μM in assay buffer (50 μM Peptide G or Scramble G, 1% DMSO and 1×PBS) or in assay buffer containing no peptide using a 96 well black plate (BD Falcon). Using a SpectraMax i3 MultiMode instrument (Molecular Devices), spectra were collected in 1 nm increments from 300 nm to 460 nm using an excitation wavelength of 270 nm. Tryptophan quenching was graphed as change in 350 nm fluorescence as a function of C3 concentration after subtracting baseline C3 fluorescence.

BrdU Incorporation Assay. PC-3 cells were seeded overnight in a white reflective 96 well plate (Costar) at 1,500 cells per well. Media was aspirated and cells were treated with 100 nM, 500 nM, 1 µM, 10 µM, 20 µM, 40 µM, 60 µM, 80 µM, or 100 µM C3 diluted in the previously described media with the addition of 0.5% DMSO. Compounds were incubated for 24 hours at 37° C. with 5% CO2 and assayed for BrdU incorporation using the manufacturer's kit and protocol (Cell Signaling Technology). Relative light units were quantified from Brd-U HRP using a GloMax Multi-Mode Reader. C3 signal was normalized to PC-3 cells exposed only to media with 0.5% DMSO. An $IC_{50}$ was calculated as described.

Apoptosis Assay. PC-3 cells were seeded overnight in white reflective 96 well plates at 15,000 cells per well. Media was aspirated and cells were treated for 6, 12, 24, or 48 hours with 1 µM, 10 µM, or 50 µM C3 diluted in the previously described media with the addition of 0.5% DMSO. Media was aspirated and cells were assayed for caspase 3/7 activity using a CaspaseGlo kit (Promega). Relative luciferase units were quantified using a GloMax MultiMode Reader.

RT-qPCR. PC-3 cells were seeded in 6 well plates at $3 \times 10^5$ cells per well and incubated with 50 µM C3 or DMSO equivalent in 1×RPMI-1640, 1× anti-anti, and 2% FBS (ThermoFisher) for 48 hours. PC-3 cells were lifted using 20 mM EDTA in 1×DPBS and pelleted before isolating total RNA using the RNeasy Mini Kit (Qiagen). 1 µg of RNA per sample was reverse transcribed using the amfiRivert cDNA synthesis master mix (GenDEPOT). Real-time PCR wells contained 1 µL cDNA template, 2×SYBR Green Master Mix (Applied Biosystems), and 20 µM forward and reverse primers. Primer sequences are provided in Table 2. qRT-PCR was performed on an Eppendorf Realplex 2S (Eppendorf), using: 40×95° C. for 3 mins; 95° C. for 3 s; 60° C. for 30 s; 72° C. for 8 s and analyzed using EP Realplex software (version 2.2). Fold changes were normalized to GAPDH using the ddCT method.

Wound Healing Assay. PC-3 cells were seeded in 6 well plates at $3 \times 10^5$ cells per well in complete media until the cells reached confluency. Three horizontal and three vertical scratches were made in the confluent monolayers using a standard 200 µL pipette tip and cellular debris were removed by washing with 1×DPBS three times. 1×RPMI-1640 supplemented with C3 or DMSO was added and cells were incubated for 48 hours as described previously. 0 hour and 48 hour images were acquired using a bright field microscope (VWR) and repositioning at 48 hours was achieved using x,y stage coordinates after washing the monolayer three times with 1×DPBS to remove debris. Images were uploaded and analyzed for scratch geometry using the tscratch program (96). First, global thresholding was performed, then individual images were manually inspected for single image threshold adjustment and scratch geometries were quantified.

C3 Dose Experiment for Proteomics. PC-3 cells were seeded at $2.5 \times 10^5$ cells per well in six well plates in complete media and treated with 10 µM C3 or 0.1% DMSO for 72 hours with a media change (also containing compound or vehicle) at the 48 hour mark. After 72 hours, cells were lifted using 20 mM EDTA in 1×DPBS, pelleted, snap frozen in liquid nitrogen and stored at −80° C. until digested for mass spectrometry. A moderate 10 µM dose was chosen from the BrdU and t-scratch functional assays.

Sample Digestion. Prior to digestion, cells were lysed using the Barocycler NEP2320 (Pressure Biosciences, Inc.). 50 al of 100 mM ammonium bicarbonate was added to the cells, and they were lysed at 4° C. under 35,000 psi for 45 minutes. 100 ag of protein was isolated for digestion using an acetone precipitation. After removing acetone, samples were reduced and alkylated, and sequence grade Lys-C/Trypsin (Promega) was used to enzymatically digest the extracted protein. All digestions were carried out in the Barocycler NEP2320 at 50° C. under 20,000 psi for 1 hour.

Digested samples were cleaned over C18 spin columns (Nest Group) and dried. Resulting pellets were resuspended in 97% purified water/3% acetonitrile (ACN)/0.1% formic acid (FA).

LC-MS. The samples were analyzed using the Dionex UltiMate 3000 RSLC Nano System coupled to the Q Exactive™ HF Hybrid Quadrupole-Orbitrap MS (Thermo Scientific). Peptides were loaded onto a trap column (20 µm×350 mm) and washed using a flow rate of 5 l/minute with 98% purified water/2% ACN/0.01% FA. The trap column was then switched in-line with the analytical column after 5 minutes. Peptides were separated using a reverse phase Acclaim PepMap RSLC C18 (75 µm×15 cm) analytical column using a 120 minute method at a flow rate of 300 nl/minute. Mobile phase A consisted of 0.01% FA in water and a mobile phase B consisted of 0.01% FA in 80% ACN. The linear gradient started at 5% B and reached 30% B in 80 minutes, 45% B in 91 minutes, and 100% B in 93 minutes. The column was held at 100% B for the next 5 minutes before being brought back to 5% B and held for 20 minutes. Sample was injected into the QE HF through the Nanospray Flex™ Ion Source fitted with an emission tip from Thermo Scientific. Data acquisition was performed monitoring the top 20 precursors at 120,000 resolution with an injection time of 100 milliseconds.

Proteomics Data Processing. Raw files obtained from the QExactive were uploaded using MaxQuant version 1.5.5.1 (97). The following settings were applied in MaxQuant: Label free standard analysis using a multiplicity of 1. Label free quantitation (LFQ) was performed using a minimum ratio count of 2 with fast LFQ. Peptides were re-quantified and matched. Digestion was set to trypsin and Lys-C using a max missed cleavage of 2. The Orbitrap parameter was selected with a first search peptide tolerance of 20 ppm and a main search peptide tolerance of 4.5 ppm. Individual peptide mass tolerances were turned on with a centroid match tolerance of 8 pm and a centroid half width of 35 ppm. Calibration was intensity independent with a minimum peak length of 2, a max charge of 7, and a minimum score of 70 for recalibration. Oxidation of methionine and N-terminal acetylation were selected as variable modifications with a max of five modifications per peptide. Iodoethanol was selected as a fixed modification and contaminants were not excluded during the initial quantification. The minimum peptide length was set to 7 and the max peptide mass was set to 4600 Da. For unspecified searches, the minimum peptide length was set to 8 and the max peptide length was set to 25. Unmodified unique and razor peptides were used for quantification. At the peptide match level, false discovery rate was set to 0.01. Second peptides were included and match between runs was turned on with a match window time of 1 minute and an alignment window time of 20 minutes. Peptides were identified using an annotated human proteome .fasta from the Uniprot database.

Proteomics Data Analysis. The identified protein groups generated by the MaxQuant program were uploaded to the Perseus program version 1.5.3.0 (98). Site only, reverse, and contaminant peptides were removed from the dataset and missing values were imputed using a normal distribution. Invalid values were then excluded. Empty columns were removed. The volcano plot function was used to identify proteins that were significantly changed using a t-test with a false discovery rate of 0.05 and an $S_0$ of 0.1. A 1.5 log 2 fold cutoff change was applied for Ingenuity Pathway Analysis (IPA, Qiagen).

Angiogenesis Tube Formation Assay. EA.hy926 cells were cultured as described earlier. $3 \times 10^4$ cells were seeded per well into a clear 96 well plate with 50 μL of preformed matrigel media and treated with 1, 10, or 50 μM C3 or 0.1% or 0.5% DMSO in 1×DMEM, 10% FBS (ThermoFisher), and 1× anti-anti. Calcein was added following the manufacturer's protocols (Cellbiolab) and tube formation images were captured using an inverted fluorescence microscope (Olympus, IX71).

c-MYC Binding Site Luciferase Reporter Assay. 15,000 PC-3 cells were seeded per well in a white reflective 96 well plate and transfected next day using 200 ng of a c-MYC binding site luciferase (pBV-Luc wt MBS 1-4) reporter plasmid and 4 ng of cytomegalovirus (CMV)-LacZ (B-Gal) plasmid for six hours using DMRIE-C transfection reagent according to manufacturer's instructions. pBV-Luc wt MBS 1-4 was a gift from Bert Vogelstein (Addgene plasmid #16564). Transfection reagent was removed and replaced complete media for an additional 18 hours. Cells were then treated with 1, 10, or 50 μM of C3 for 24 hours. Media was aspirated, 1× passive lysis buffer was added, and cells were freeze-thawed after being stored at −80° C. Luciferase activity detection was measured using the Luciferase Assay System (Promega) and a Glomax Discover luminometer (Promega).

Endogenous 37 LR Expression Levels in Screened Cell Lines

PC-3, Endo, TC2-Ras, SH-SY5Y, and LNCAP cells were grown in 100 mm plates in complete media and lifted at ~90% confluency using 20 mM EDTA in 1×DPBS. Cells were pelleted, media was aspirated, and pellets were frozen at −80° C. until required for analysis. Total protein was isolated using 1×RIPA buffer (Thermo Scientific) containing 1×Halt Protease Inhibitor (Thermo Scientific), 5 mM EDTA, and Phosphatase Inhibitor Cocktails 2 and 3 (Sigma Aldrich). Cells were lysed passively on ice for thirty minutes, sheared using a tuberculin syringe (BD) and supernatant was separated from cellular debris after a 30 minute 14,000 rpm spin at 4° C. Protein concentration was determined using the BCA assay (Thermo Scientific). 50 ag of protein was loaded onto a Bolt 4-12% Bis-Tris Plus gel (Life Technologies) and electrophoresed for 30 minutes at 200V. Proteins were transferred onto nitrocellulose using the iBlot2 system (Life Technologies). The blot was blocked for 1 hour at room temperature using 5% BSA in 1×PBS with 0.1% Tween-20 (Acros). 37 LR was probed using a rabbit polyclonal (Bioss, bs-0900R, 1:250) and beta actin was probed using a mouse monoclonal (ThermoFisher, MA5-15739, 1:5000). Goat anti-rabbit IgG secondary (Licor, 925-68021, 1:15,000) and goat anti-mouse IgG secondary (Licor, 925-32210, 1:15,000) were used to detect primary antibody and signal was detected using the Licor Odyssey CLx. Image Studio Lite (Licor, ver. 5.2) was used to quantify pixel intensity.

Treatment of PC-3 Cells with Exogenous PEDF

Recombinant PEDF (BioProductsMD) was resuspended in PEDF Buffer (0.2 M NaCl, 20 mM sodium phosphate, and 1 mM DTT; ph 6.4). 1,500 cells per well were seeded in a clear 96-well plate in RPMI-1640 with 1% anti-anti and 10% FBS and allowed to grow overnight. A 0-hour recording was taken using CCK-8 and compared to a 48-hour reading after incubating PC-3 cells with recombinant PEDF (0.1 μM to 1.6 aM) in RPMI-1640 with 1% anti-anti and 1% FBS. PEDF Buffer was used as a vehicle control. Each 48 hour value was divided by its respective 0 hour value and normalized to PEDF Buffer to obtain % cell viability.

Generation and Characterization of TC2-Ras Cells

The TC2-Ras cell line was generated by our group and is useful in that they are very aggressive in their growth and form tumors that are challenging to treat, hence the benefit of testing new compounds with it. As described in Materials and Methods, TC2-Ras were generated by transduction of parental cells TRAMP-C2 with a lentivirus expressing a Ras gene at MOI=1. When assayed for growth rate in vivo, TRAMP-C2 ($10^6$) are very slow growing as compared to TC2-Ras ($5 \times 10^5$) when implanted subcutaneously in 6-8 week old C57/BL6 male mice. As described in Materials and Methods, TC2-Ras also were transduced with MOI=1 of a lentivirus expressing mouse androgen receptor (mAR). mAR activity was assayed in vivo by bioluminescence imaging. An adenoviral vector containing an AR-responsive cassette expressing reporter gene luciferase was used. The adenovirus was administered intravenously ($2 \times 10^8$ pfu/i.v.) 3 days following subcutaneous TC2-Ras cell implantation ($10^4$ or $10^5$, without mAR (−mAR control) or with mAR (+mAR) in C57/BL6 male mice. Mice were injected intraperitoneally with 150 mg/kg Luciferin (10-20 min incubation) followed by a 5 min signal acquisition using an IVIS 100 imager (Caliper/PerkinElmer, Downers Grove, Ill.) and analyzed with LivingImage 3.1 software (Caliper/PerkinElmer), with signals reported as photons per second per cubic centimeter per steridian (p/sec/cm$^2$/sr).

Statistics. Statistical analysis was performed using GraphPad Prism 6. All assays were run in triplicate with values shown as the mean±SEM unless otherwise indicated. Student's t-test was used for pairwise comparisons and one-way ANOVA was used for group comparisons with significance set at p<0.05. In the case of multiple comparisons, the Holm-Sidak test was used or a false discovery rate was applied.

Example 1

In Silico Screens Produced a Hit Compound with Promising Antitumor Activity in In Vitro Assays Docking the Maybridge Hitfinder™ library against the 37 LR crystal structure using "Docking @UTMB" generated 24 compounds with predicted docking scores ranging from −9.3 kcal/mol to −7.9 kcal/mol. After excluding compounds with poor chemical qualities, seven compounds were chosen for further in vitro studies. Notably, all compounds contained piperazine-like moieties (FIG. 1) and had little to no preexisting data in the chemical literature. We carried out a 96 hour study of cell viability for the initial compound screen because we did not know the relationship between time and dose for the compounds selected a priori. A six-dose screen (6 μM to 100 aM) (FIG. 2) separated compounds into two groups. C1, C2, C3, and C4 inhibited cell viability in a dose dependent manner whereas C5, C6, and C7 had mixed responses or did not inhibit cell viability in various cell lines. The vehicle, DMSO, had no effect on tumor cell lines LNCaP, TC2-Ras, PC-3, or SH-SY5Y but did have a mild effect on Ea.hy.926 endothelial cells at higher doses. IC50s obtained from dose response curves revealed that C3 had the strongest effect on cell viability in the majority of cell lines tested. C3 inhibited cell viability in the androgen dependent LNCaP cell line (10.28 μM), the aggressive and metastatic androgen independent PC-3 cell line (~0.8 μM), and in the neuroblastoma cell line SH-SY5Y (18.57 μM) (Table 2). Because C3 strongly inhibited cell viability in PC-3 cells, we chose to investigate the mechanism for reduction of cell viability using these cells.

Example 2

Effectiveness of C3 Correlates with Endogenous 37 LR Levels

Figure 11A:
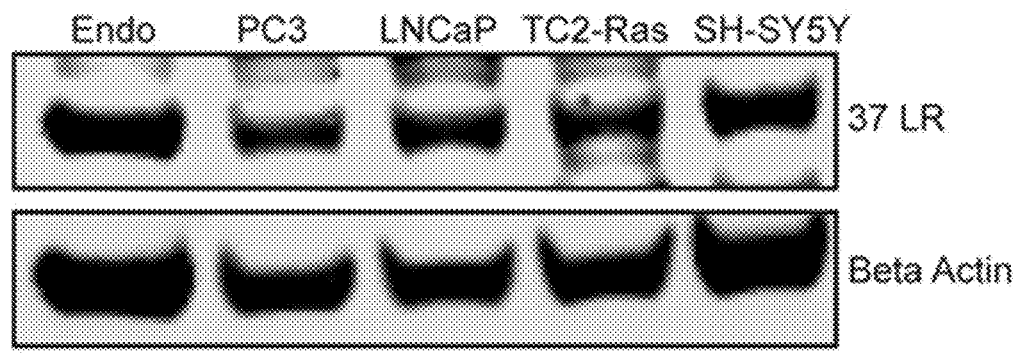
FIG. 11A. Effectiveness Of C3 Correlates With Endogenous 37 LR Levels Cell pellets for the five cell lines screened for cell viability were assayed for endogenous 37 LR levels using a rabbit polyclonal against 37 LR. Beta-actin was used as a control.
Figure 11B:
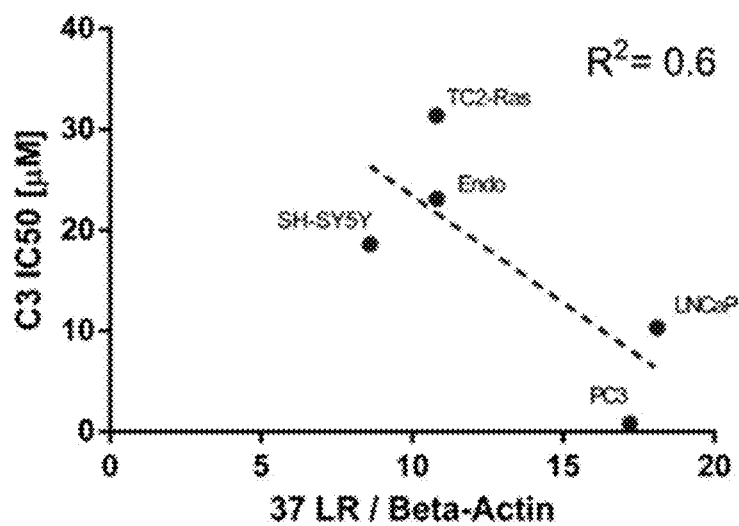
FIG. 11B shows after normalizing 37 LR protein levels to beta-actin levels, the protein expression values were graphed against the C3 $IC_{50}$ responses measured in Table 1. GraphPad Prism was used to generate a linear fit (n=1).

Because C3 reduced cell viability at lower concentrations in PC-3 and LNCaP cell lines than TC2-Ras, SH-SY5Y, and Ea.hy.926 cell lines, we examined whether C3 IC50 values might correlate with endogenous 37 LR levels. PC-3 and LNCaP cell lines expressed 37 LR approximately two fold higher than SH-SY5Y and 1.5 fold higher than Ea.hy.926 and TC2-Ras, with a modest correlation ($r^2$=0.6) between lower C3 IC50s and higher expression levels of 37 LR (FIG. 11).

Example 3

Redocking Of Hit Compound C3

Figure 3:
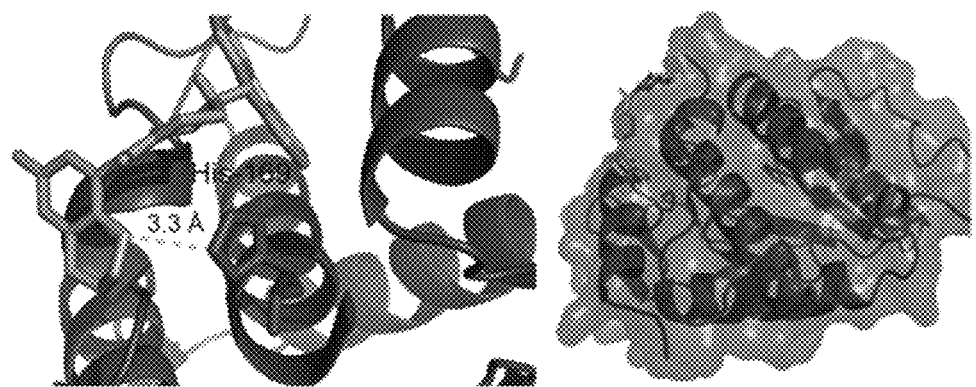
FIG. 3. Redocking of Hit compound C3. Redocking of C3 was performed as described in the methods and visualized using PyMol. Left, a pose depicting the most energentically favored positioning of C3 from the simulation featuring a 3.3 Å hydrogen bond between the benzodioxin moiety and His 169. Right, the predicted binding pocket for C3 with the 37 LR crystal structure.
Figure 12:
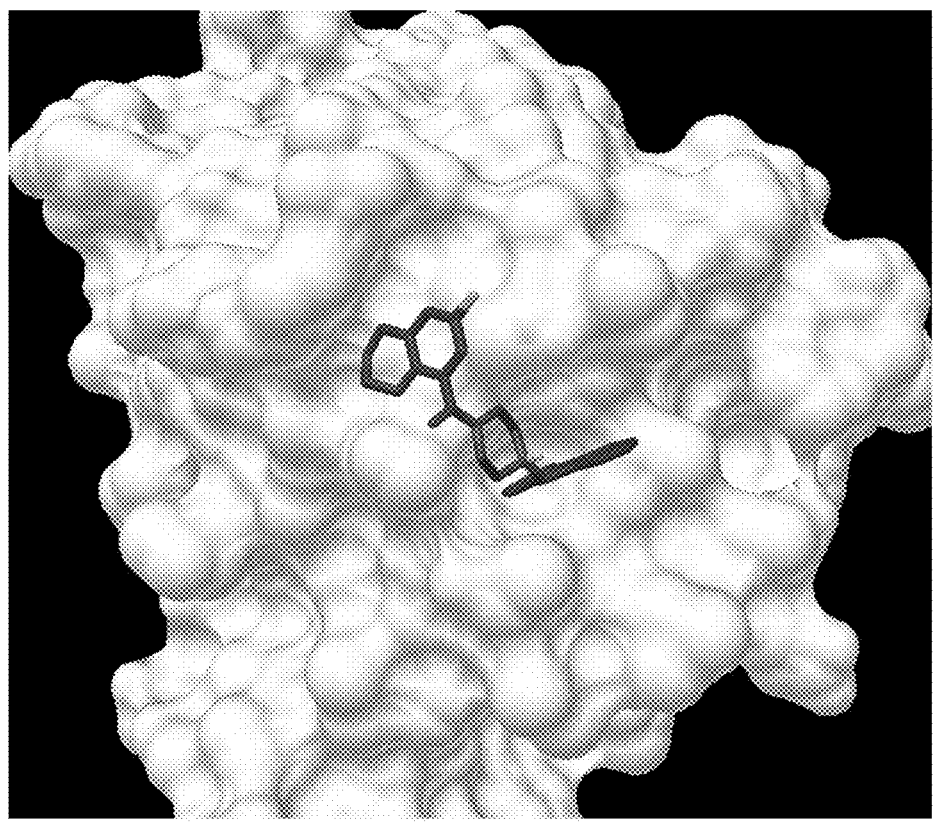
FIG. 12. His-169 Protonation State Does Not Alter C3 Binding In Silico C3 was redocked to the LR crystal structure using an epsilon-protonated state His-169 or a delta-protonated state His-169 residue using Autodock Vina. A near complete superposition of the two poses is depicted in the image, demonstrating that His-169 protonation does not affect C3 binding to the LR pocket.

C3 was redocked to the 37 LR crystal structure using AutoDock Vina and AutoDockTools to assess predicted binding state and visualized using PyMol. Using a grid encompassing the entire protein as described in the methods, C3 was predicted to interact with His-169 of the 37 LR structure via a 3.3 Å hydrogen bond (FIG. 3). Moreover, the predicted interaction site lies within the first binding region for laminin and the known binding region for PEDF. Altering the protonation state of His-169 did not change predicted binding of C3 in simulation (FIG. 12).

Example 4

Figure 4:
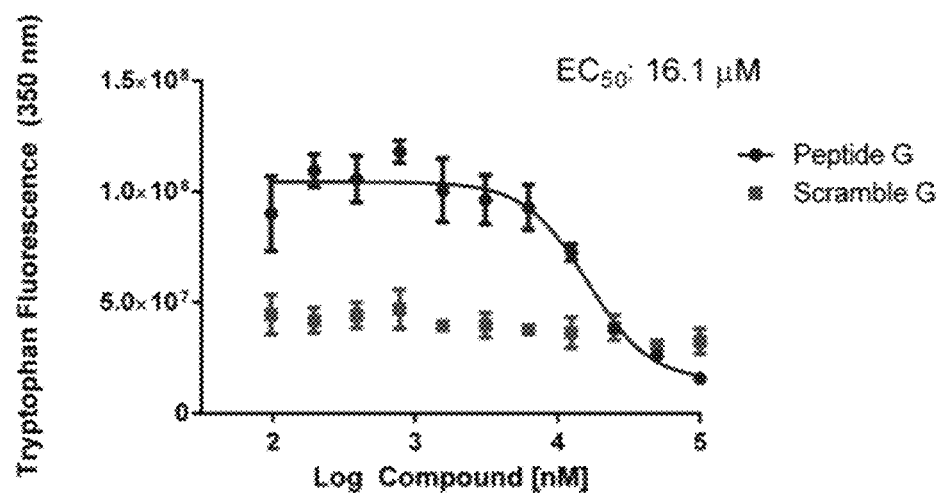
FIG. 4. Reduction of Tryptophan Fluorescence by C3. 50 μM peptide G or Scramble G was incubated with concentrations of C3 ranging from 100 nM to 100 μM. Intrinsic tryptophan fluorescence was quantified at 350 nm emission (270 nm excitation) and graphed as a function of C3 dose after subtracting baseline C3 fluorescence. GraphPad Prism was used to determine an ECso for tryptophan reduction as described in the method (n=3±SEM).

C3 Reduces Intrinsic Tryptophan Fluorescence in Peptide G-A Peptide Representing the 37LR Laminin Binding Pocket Computational redocking suggested that C3 engaged 37LR at His 169, a residue that lies squarely within the laminin binding region of 37 LR and notably, the active laminin binding site spanning amino acids 161 to 180 (61). After inspecting the amino acid sequence, commonly referred to as Peptide G, we noticed that the sequence contained two tryptophans. We tested the hypothesis that alterations to intrinsic tryptophan fluorescence could be a readout for C3 binding to Peptide G by titrating C3 in an assay buffer containing Peptide G or a 20-mer same sequence scramble (Scramble G) (FIG. 4). Titration of C3 from 0.1 to 100 µM reduced intrinsic tryptophan fluorescence in a dose dependent manner with an EC50 of 16.1 µM. Titration of C3 did not appreciably alter the intrinsic tryptophan fluorescence of Scramble G.

Example 5

C3 Treatment Elicits PEDF-Like Gene Expression Changes in PC-3 Cells

Figure 5A:
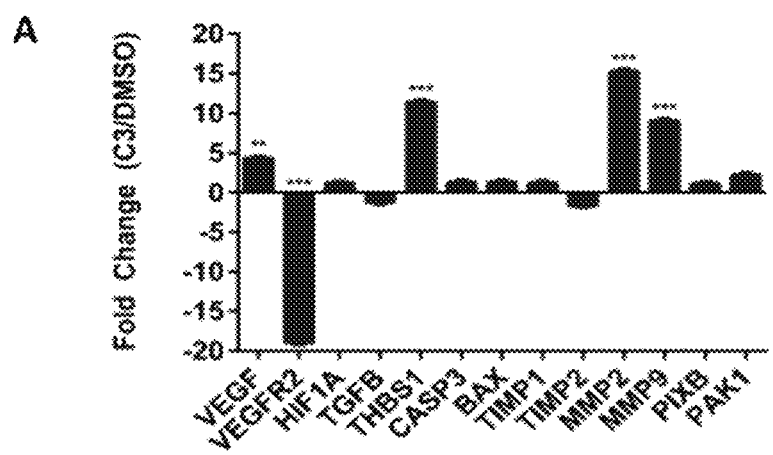
FIG. 5A shows PC-3 response to C3. Expression of PEDF-signaling associated genes from PC-3 cells treated with 50 μM C3, compared to DMSO control and normalized to GAPDH (n=3, mean±SEM). A Holm-Sidak multiple t test was used for statistical analysis (*p<0.05,O<0.01, *<0.001).

Since C3 inhibited cell viability and displayed predicted binding to empirically determined binding sites on 37 LR (34), we used RT-qPCR to screen a panel of known PEDF-signaling related genes involved in PEDF's ability to both inhibit angiogenesis and activate apoptosis in a cell-type dependent manner (FIG. 5A). mRNA levels were examined at 48 hours to provide a window for newly synthesized transcripts to be measured. Genes involved in migration/invasion and/or extracellular matrix (ECM) communication also were assayed. We observed significant ($p<0.05$) upregulations in vascular endothelial growth factor (VEGF), thrombospondin-1 (THBS 1), matrix metalloproteinase (MMP)-2 and -9, and downregulations in vascular endothelial growth factor receptor 2 (VEGFR2). Transforming growth factor beta (TGFB) and tissue inhibitor of metalloproteinase 2 (TIMP2) were downregulated and proapoptotic factors caspase-3 (CASP3) and bcl-2-associated x protein (BAX) and migration/invasion regulators Rho guanine nucleotide exchange factor 7 (PIXB) and PAK1 (P21 (RAC1) Activated Kinase 1) were upregulated as a trend, but these changes were not significant.

Example 6

C3 Inhibits Endothelial Tube Formation

Figure 5B:
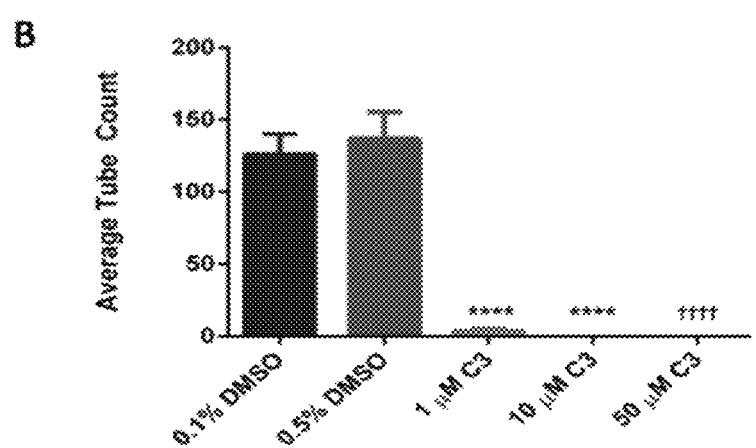
FIG. 5B shows Endothelial Tube Formation Assay. Average tube count for 0.1% DMSO, 0.5% DMSO, and 1, 10 and 50 μM treatment with C3 (n=7, mean±SEM). 1 and 10 μM C3 were compared with respective 0.5% DMSO (unpaired two-tailed t test, ****<0.0001). 50 μM C3 was compared with respective 0.1% DMSO (unpaired two-tailed t test p<0.0001).

Because C3 downregulated VEGFR2 and upregulated THBS 1 in PC3 cells, we tested the hypothesis that C3 exhibited anti-angiogenic potential using an endothelial tube formation assay (FIG. 5B). In this assay, tube formation proceeded uninhibited by the presence of vehicle (DMSO), but not in the presence of 1, 10, or 50 µM of C3 compound ($p<0.05$). Inhibition of tube formation by C3 did not alter calcein uptake (data not shown), suggesting the inhibition was not driven by a direct apoptotic mechanism.

Example 7

C3 does not Inhibit Cell Viability Via Caspase 3/7 Mediated Apoptosis

Figure 6A:
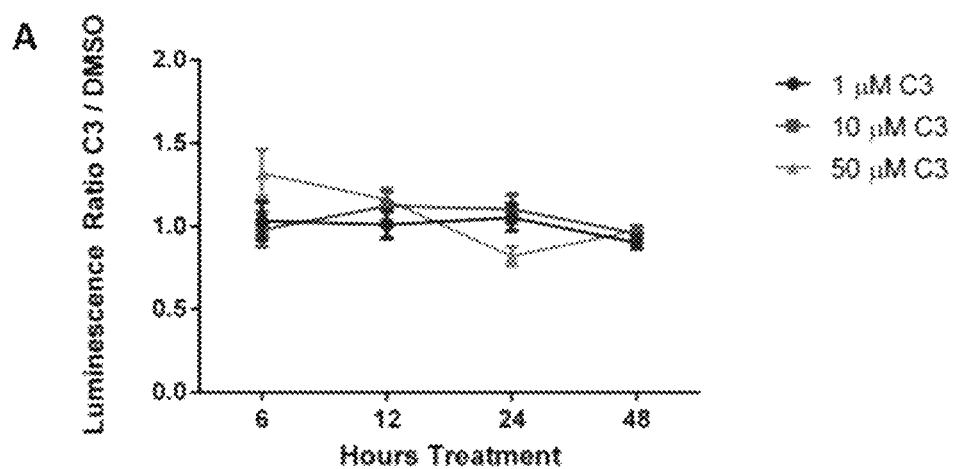
FIG. 6A shows Caspase 3/7 Activation in Response to C3 treatment. Average luminescence ratio (active caspase 3/7) for PC-3 cells treated with 1, 10 or 50 μM C3 for 6, 12, 24 and 48 hours (n=3, mean±SEM) and normalized to DMSO control (results not significant, one-way ANOVA).

To determine the mechanism for inhibition of cell viability by C3, we treated PC-3 cells with 1, 10, or 50 µM of C3 for 6, 12, 24, or 48 hours continuously and measured activation of caspase 3/7 using a luminescence based assay (FIG. 6A). At 6 hours, 50 µM C3 caused a slight increase in caspase 3/7 activity but the results were not significant at any time point for any dose.

Example 8

C3 Inhibits Cell Viability Via Inhibition of Cellular Proliferation

Figure 6B:
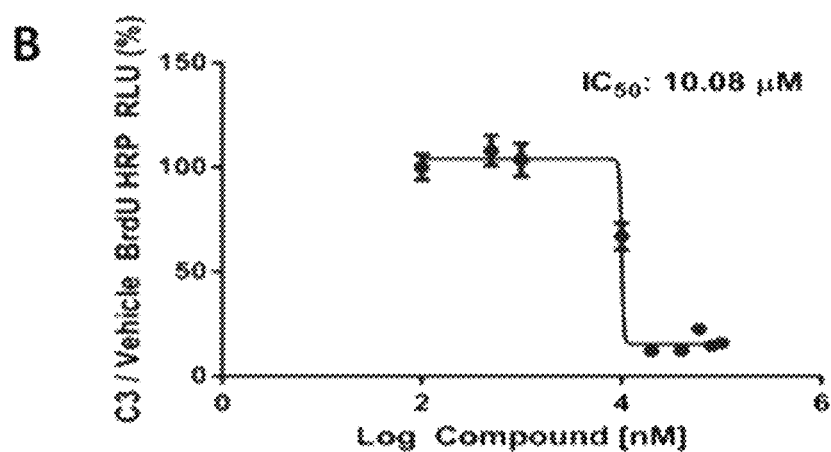
FIG. 6B shows BrdU incorporation in Response to C3 treatment. PC-3 cells were treated with 100 nM to 100 μM C3 for 24 hours and BrdU incorporation was quantified using HRP generated luminescence from an antibody pair recognizing BrdU (n=6, mean±SEM). C3 BrdU signal was normalized to a row where PC-3 cells were exposed to 0.5% DMSO (assay conditions). Curve obtained using GraphPAd Prism as described in the methods.

Since C3 did not appear to inhibit cell viability by an apoptotic mechanism, we tested the hypothesis that PC-3 cells inhibited cell viability due to a reduction in cellular proliferation in response to treatment. A dose curve for C3 was established and bromodeoxyuridine (BrdU) incorporation was used as a readout for proliferation (FIG. 6B). We observed inhibition of BrdU incorporation in a dose dependent manner after treatment for 24 hours with an $IC_{50}$ of 10.08 µM.

Example 9

Figure 7:
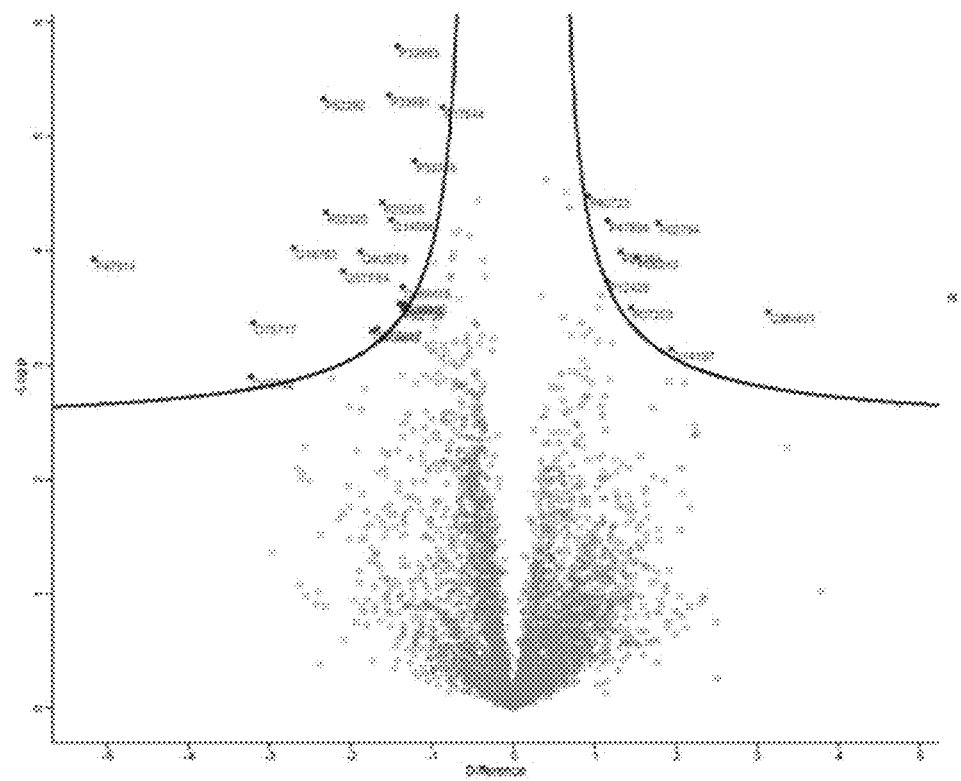
FIG. 7. Volcano Plot of Differentially regulated proteins in response to C3 treatment. PC-3 cells were treated with DMSO or 10 μM C3 for 72 hours and proteins were quantified using label free quantitative mass spectrometry. Proteins were graphed by fold change (Difference) and significance (−Log p) using a false discovery rate of 0.05 and an $S_0$ of 0.1. Protein IDs in red were considered significantly up or down regulated using the Perseus software.

Label-Free Quantitative Proteomics Suggests C3 Alters Levels of Proteins Associated with DNA Maintenance, DNA Synthesis, and Protein Translation To further elucidate potential mechanisms of action for C3, we employed a label free quantitative mass spectrometry approach. Differential changes to the proteome of PC-3 cells were examined at 72 hours to provide a viable window for newly translated proteins to be measured. Perseus was used to generate a volcano plot of significantly up and down regulated proteins from the 3,904 proteins differentially detected between vehicle control (DMSO) and 10 µM C3 after 72 hours of treatment. 29 proteins were significantly differentially regulated in response to C3 treatment (FIG. 7) and 16 proteins were significantly differentially regulated at a fold change cutoff of 1.5 (Table 3). Specific protein changes induced by C3 treatment included downregulation of the mini chromosome maintenance (MCM) family of proteins, responsible for replication fork formation. C3 also downregulated two E2 ubiquitin ligases required for mitotic progression (UBE2C and UBE2S). The most downregulated protein (−5.3 FC), RPL29, is incorporated into the 60S ribosome. Additionally, the second most upregulated protein (1.9 FC), ICT1, responds to stalled mitochondrial ribosomes.

Example 10

Figure 8:
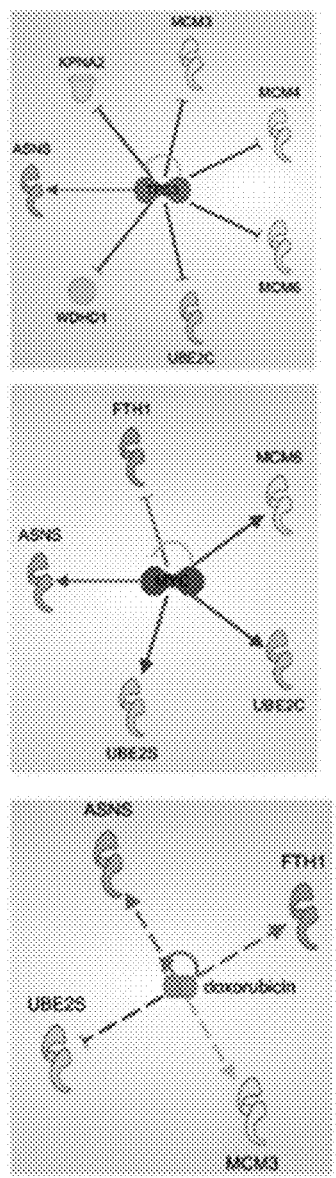
FIG. 8 Ingenuity pathway analysis of proteomic data from C3 treatment of PC-3 cells. Significantly up and down regulated proteins were analyzed using Ingenuity Pathway Analysis Software and mapped to canonical pathways.

Ingenuity Pathway Analysis Predicts Inactivation of Myc, Activation of P53, and Suggests a Doxorubicin Like Phenotype Proteomics analyses utilizing Ingenuity Pathway Analysis (IPA) of significant (p<0.05, FC 1.5) proteins altered upon treatment with 10 µM of compound C3 suggested a predicted activation of tumor suppressor p53 pathways and a predicted deactivation of tumor promoter c-myc (FIG. 8). IPA predicted an activation of P53 corresponding to the experimentally detected downregulations of MCM family proteins and other proteins involved in DNA synthesis and integrity (KPNA2, UBE2C, WDHD1). IPA predicted an inactivation of c-myc corresponding to downregulation of MCM6, UBE2C, and UBE2S and the upregulation of ASNS (asparagine synthase). The proteomic signature obtained with C3 compared to vehicle control (DMSO) was linked to the well-characterized chemotherapeutic doxorubicin by IPA.

Example 11

Figure 9:
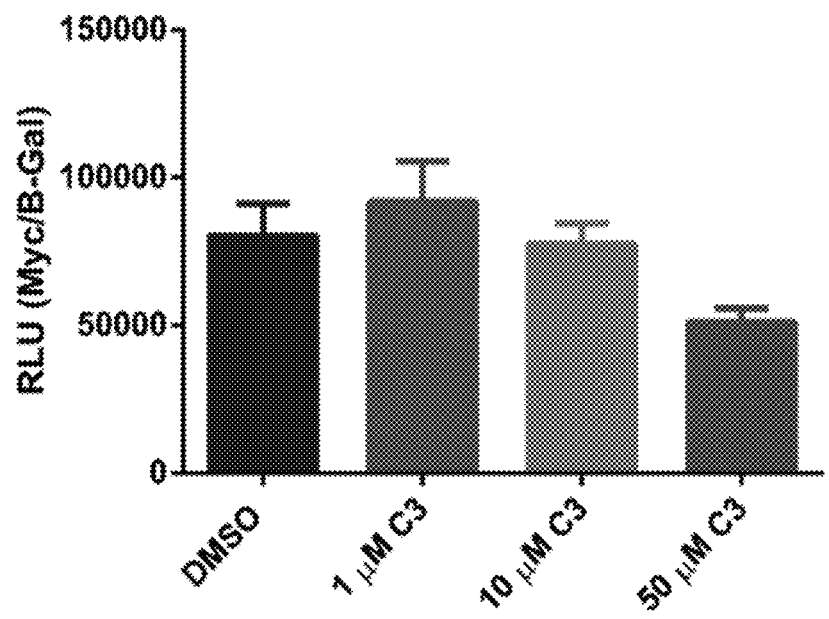
FIG. 9. Luciferase promoter Assay in PC-3 cells. PC-3 cells were treated with 1, 10, 50 μM C3 or DMSO control for 24 hours after a 24 transfection with Myc-Luc and B-Gal plasmid to normalize for transfection efficiency (n=6, mean±SEM). Relative light units calculated by normalizing Myc-Luc signal to B-gal signal. A one-way ANOVA was used for statistical analysis (P<0.05). The linear trend was also significant (pose test for linear trend, p, 0.05).

C3 Inhibits c-Myc Binding Activity at 50 µM
Because P53 status and function is impaired in PC-3 cells, we chose to orthogonally validate the IPA prediction of c-myc inactivation using a promoter-based reporter assay (FIG. 9) consisting of four c-myc binding sites upstream of a luciferase gene (62). 1 and 10 µM C3 had no significant effect on luciferase reporter activity however 50 µM C3 significantly reduced c-myc binding activity by 36%.

Example 12

Compound C3 Inhibits Wound Healing in a Scratch Assay Using PC3 Cells

Figure 10A:
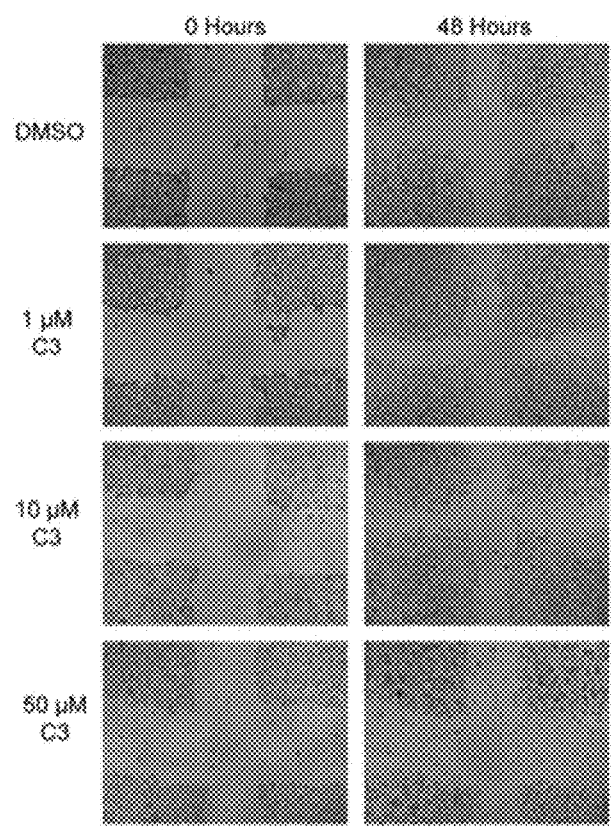
FIG. 10A shows Representative Scratch Assay Brighfield Images for PC-3 cells in Response to C3 Treatment. PC-3 cells were treated with 1, 10, 50 μM C3 or DMSO control after scratch formation and images were recorded using a brightfield microscope as described in the methods.
Figure 10B:
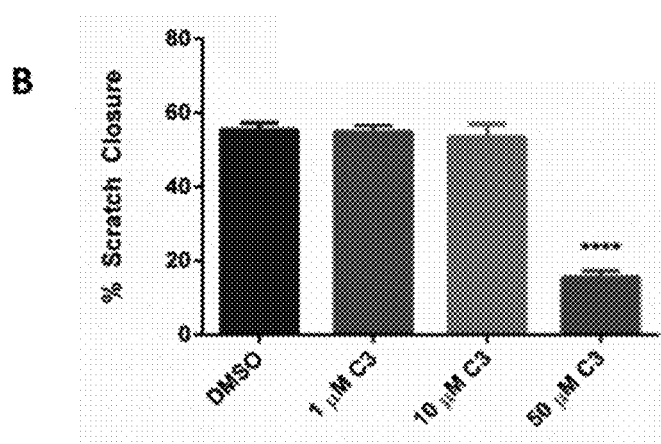
FIG. 10B shows Quantification of Scratch Assay. Brightfield images were quantified using the t-scratch program and represented as % scratch closure after 48 hours of migration compared to a 0 hour control (n=9, mean±SEM). A one-way ANOVA test was used for statistical analysis (p<0.05). A post-hoc Sidak's multiple comparisons test was also used (****p<0.001, 50 μM C3 vs. DMSO, all other doses vs. DMSO were not significant).

Because C3 inhibited growth pathways in several different assays, we decided to investigate whether C3 could inhibit wound healing in a scratch test assay as a measure of cancer cell aggressiveness as it relates to their migration capacity. The scratch assay is a well-developed method for measuring cell migration in vitro and was chosen because it mimics cell migration during wound healing in vivo and is compatible with live cell imaging (63). In this assay, we utilized the t-scratch method to assess the ability of compound C3 to promote wound closure or healing. PC3 cells were treated for 48 h with vehicle control (DMSO), or 1, 10, or 50 µM compound C3. A t-scratch was made in the center of the wells and imaged over time using a brightfield microscope (FIG. 10A). Quantification of the wound closure was performed as described in materials and methods using tscratch software. We observed that compound C3 prevented wound closure by ~70% at 50 uM (p<0.05; FIG. 10B)

Examples for Anti-Inflammatory and Pro-Chondrogenic Effect

Cell Culture. THP-1 human monocytes were purchased from ATCC (Manassas, Va.) and cultured in DMEM/10% FBS/1% Anti-Anti (Gibco). The monocytes were differentiated into macrophages with 5 ng/ml phorbol myristate 13-acetate (PMA) for 48 h and pretreated with drugs for 6 h. Lipopolysaccharide (LPS, 10 ng/ml) stimulation was performed for 1 h and cells were collected for assays. Human adipose-derived mesenchymal stromal/stem cells (ASC) were purchased from LaCell, LLC (Metairie, La.) and grown on fibronectin-coated plates in MCDB-201/DMEM/10% FBS media.

RNA isolation and qPCR. RNA was isolated from cell pellets using an RNAeasy kit (Qiagen) according to manufacturers' specifications for tissue samples. 1 µg RNA was reverse transcribed using a AmfiRivert kit (Genedepot) and 2 µl used in a SYBR green quantitative PCR reaction for detecting differences in gene expression relative to beta-actin control.

Luciferase Assays. THP-1 human monocytes were seeded in OptiMEM/1% anti-anti (Gibco) and transfected using Lipofectamine LTX (Invitrogen, Carlsbad, Calif.) in a 96-well format in white opaque plates. The monocytes were differentiated into macrophages with 5 ng/ml PMA for 48 h and pretreated with drugs for 6 h. LPS (10 ng/ml) stimulation was performed for 1 h and cells were collected for the assay in 40 uL of 1× Reporter Lysis Buffer (Promega, Madison, Wis.). The samples were freeze-thawed once and shaken for 15 min at room temp and 5 µL of lysate used in a Beta-gal luminescent assay (Clontech, Mountain View, Calif.) and the remainder of lysate was used for detecting luciferase activity (Luciferase Assay, Promega). The samples were read in a BiotekNeo (Bindley Bioscience Center).

Chondrogenesis Assay. ASC were seeded in polypropylene tubes at 5×10$^5$ cells/tube, spun to form a pellet, then allowed to spontaneously form round mass cultures or cell pellets that received media plus or minus chondrogenic supplements (TGFβ-containing Stem Xvivo media, RnD) for 8 days with media changed every 2-3 days. Controls received either vehicle (DMSO), PEDF small peptide (P18, Ref. 3), KRT or test compounds.

In vitro data analysis. Presented as mean±SD (n=3). 2-tailed t-test was utilized with p-value ≤0.05 considered statistically significant (*).

Proteomics and IPA analyses. Samples were processed and subjected to LC-MS using the Dionex UltiMate 3000 RSLC Nano System coupled to the Q Exactive™ HF Hybrid Quadrupole-Orbitrap MS (Thermo Scientific) as we have recently described (Oncotarget reference, 2017). Raw files obtained from the QExactive were uploaded using MaxQuant version 1.5.5.1 (Oncotarget Ref). The identified protein groups generated by the MaxQuant program were uploaded to the Perseus program version 1.5.3.0 and site only, reverse, and contaminant peptides were removed from the dataset and missing values were imputed using a normal distribution. Invalid values were then excluded. Empty columns were removed. We identified proteins that were significantly changed using a t-test with a false discovery rate of 0.05 and an $S_0$ of 0.1. A 1.5 log 2 fold cutoff change was applied for Ingenuity Pathway Analysis (IPA, Qiagen).

Example 13

Figure 17:
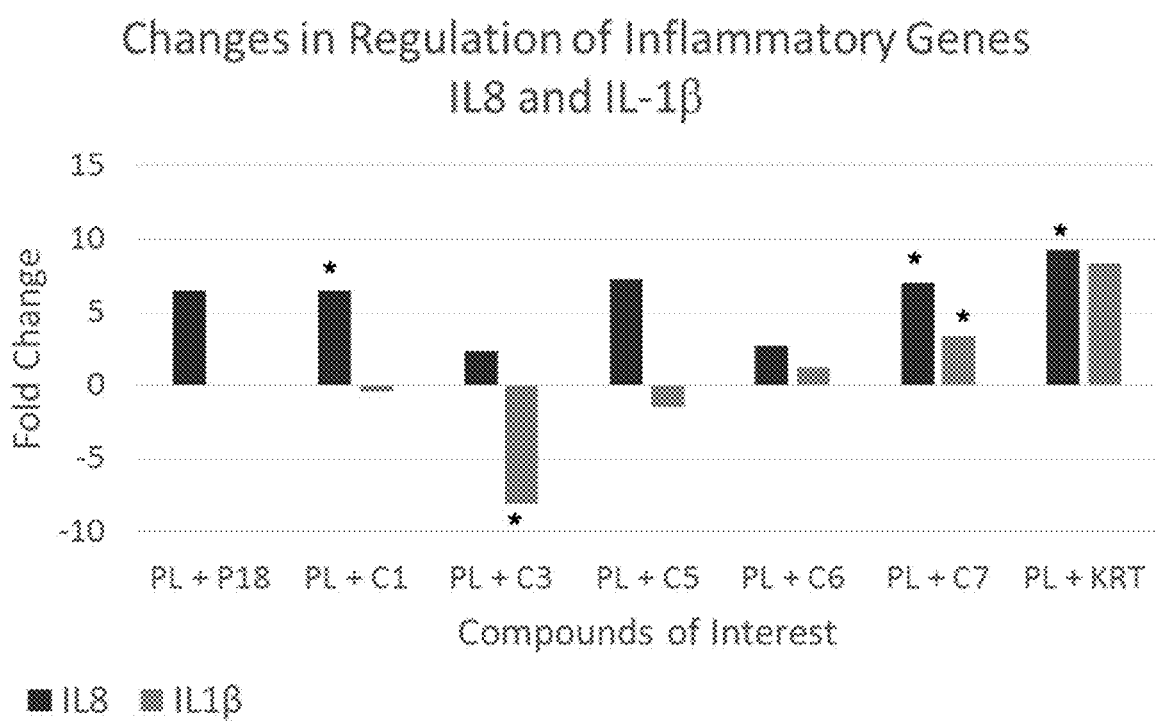
FIG. 17—Fold change in inflammatory gene expression when THP-1 monocytes are treated with Compounds of Interest. Compound C3 treatment downregulated IL1β expression even in the presence of strong LPS stimulus. PL, PMA-differentiated and treated with LPS. P18, PEDF peptide [2]. (*, p<0.05 relative to PL)

THP-1 monocytes treated with compounds of interest C1, C3, C5, C6 and C7 indicates that C3 downregulates IL1β expression even in the presence of strong LPS stimulus. See FIG. 17.

Example 14

Figure 18A:
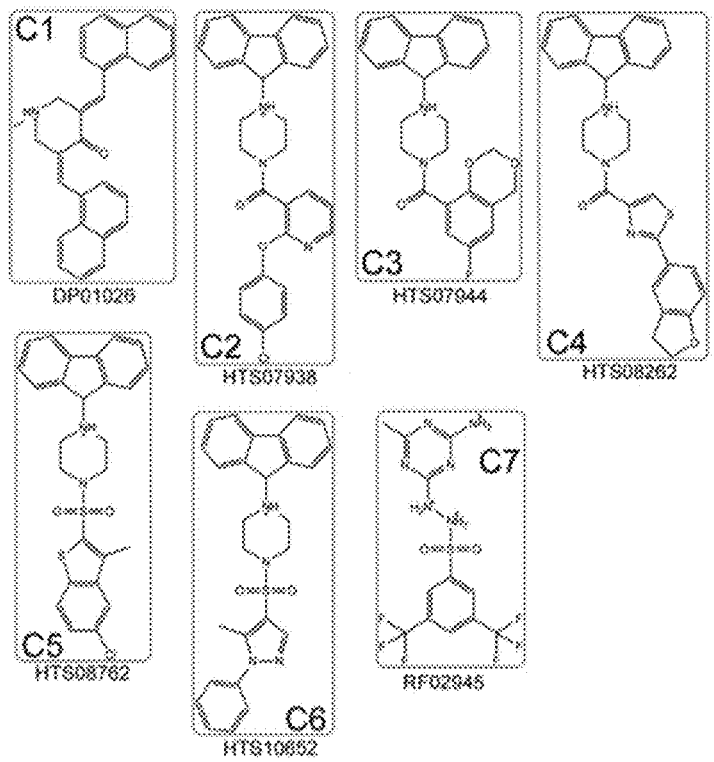
FIG. 18A Fold change in cartilage-specific genes following 8 days of treatment of ASC with Compounds of Interest. ASC show an increase in the expression of cartilage-specific genes both in the absence of chondrogenic supplements (A) and in the presence of chondrogenic supplements (B).
Figure 18A:
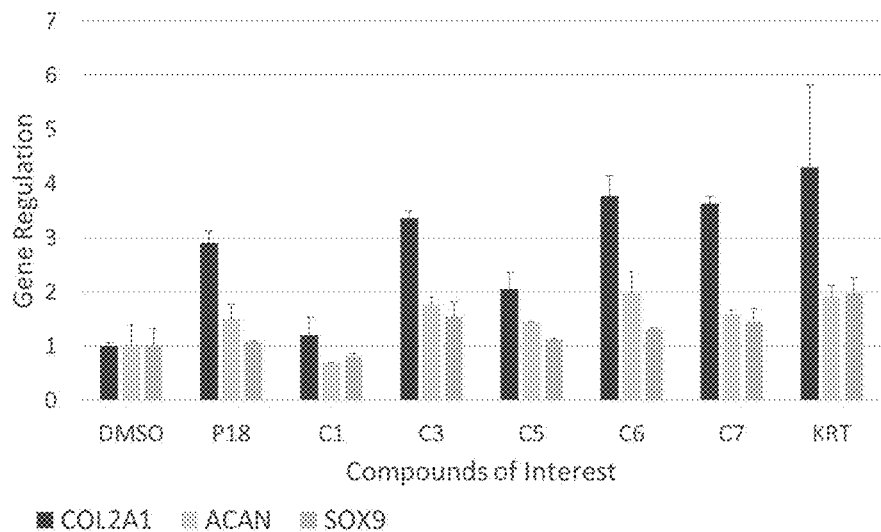
Figure 18B:
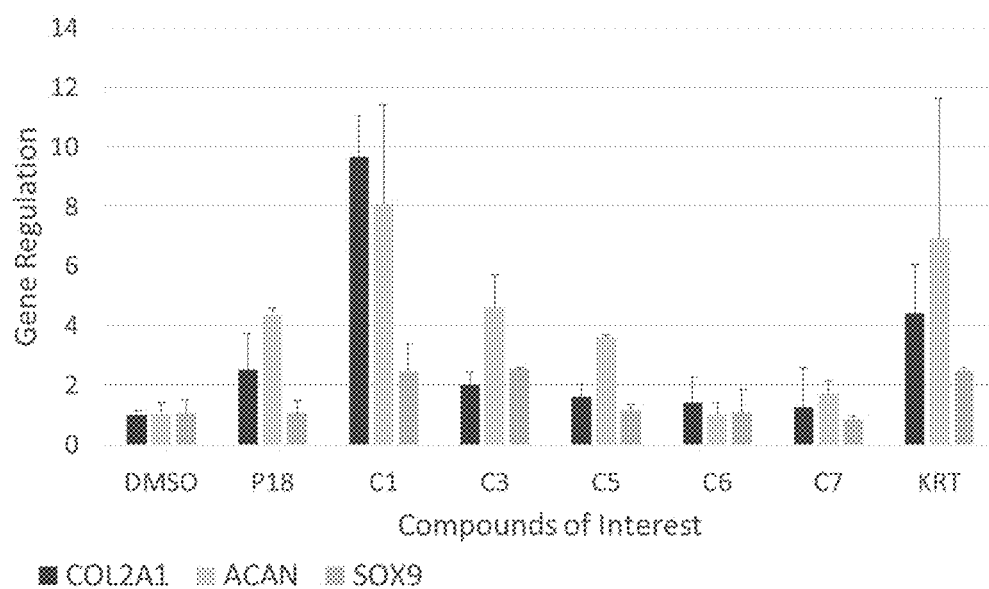
FIG. 18B—Fold change in cartilage-specific genes following 8 days of treatment of ASC with Compounds of Interest. ASC show an increase in the expression of cartilage-specific genes both in the absence of chondrogenic supplements (A) and in the presence of chondrogenic supplements (B).

Adipose derived stromal cells (ASC) treated with compounds of interest C1, C3, C5, C6 and C7 for 8 days. As shown in FIGS. 18A and 18B, in the absence or presence of chondrogenic supplement, cartilage-specific genes including COL2A1, ACAN and SOX9 had increased expression.

Example 15

Figure 19A:
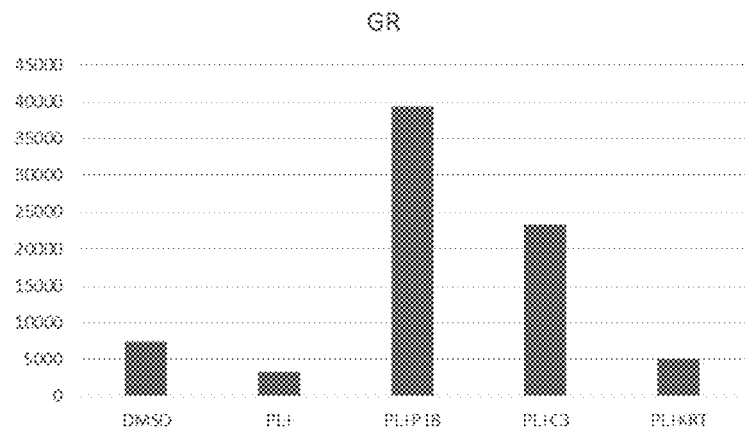
FIGS. 19A-19C Luciferase assay testing potential mechanisms for IL1P gene expression regulation. We examined the human IL10 promoter sequence and selected several transcription factors that could be responsible for regulating IL10 expression, including the Glucocorticoid Receptor (FIG. 19A), Activator Protein-1 (FIG. 19B), and Signal Transducer and Activation of Transcription 3 (FIG. 19C). AP1 and GR can act as transrepressors of inflammatory genes such as IL1 [3].
Figure 19B:
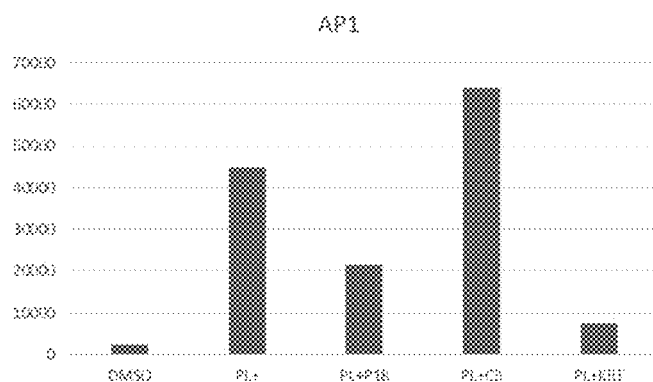
Figure 19C:
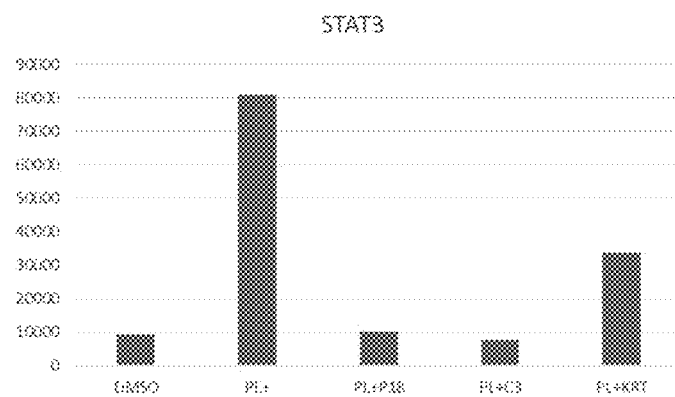
Figure 20A:
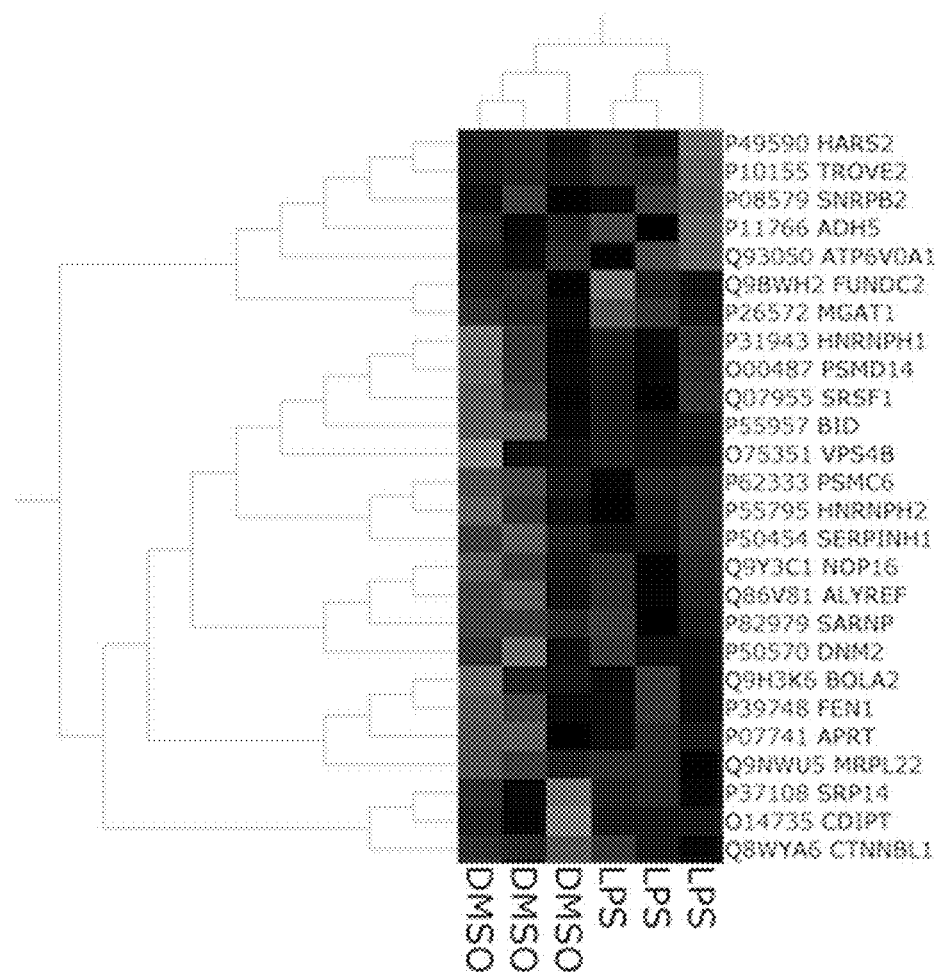
FIGS. 20A-20D Proteomics results with THP-1 monocytes. Heatmap images showing how Compound C3 modifies the LPS protein signature in THP-1 monocytes. Fold changes observed for treatments (LPS, C3, C3 followed by LPS, or LPS followed by C3) relative to DMSO vehicle control.
Figure 20B:
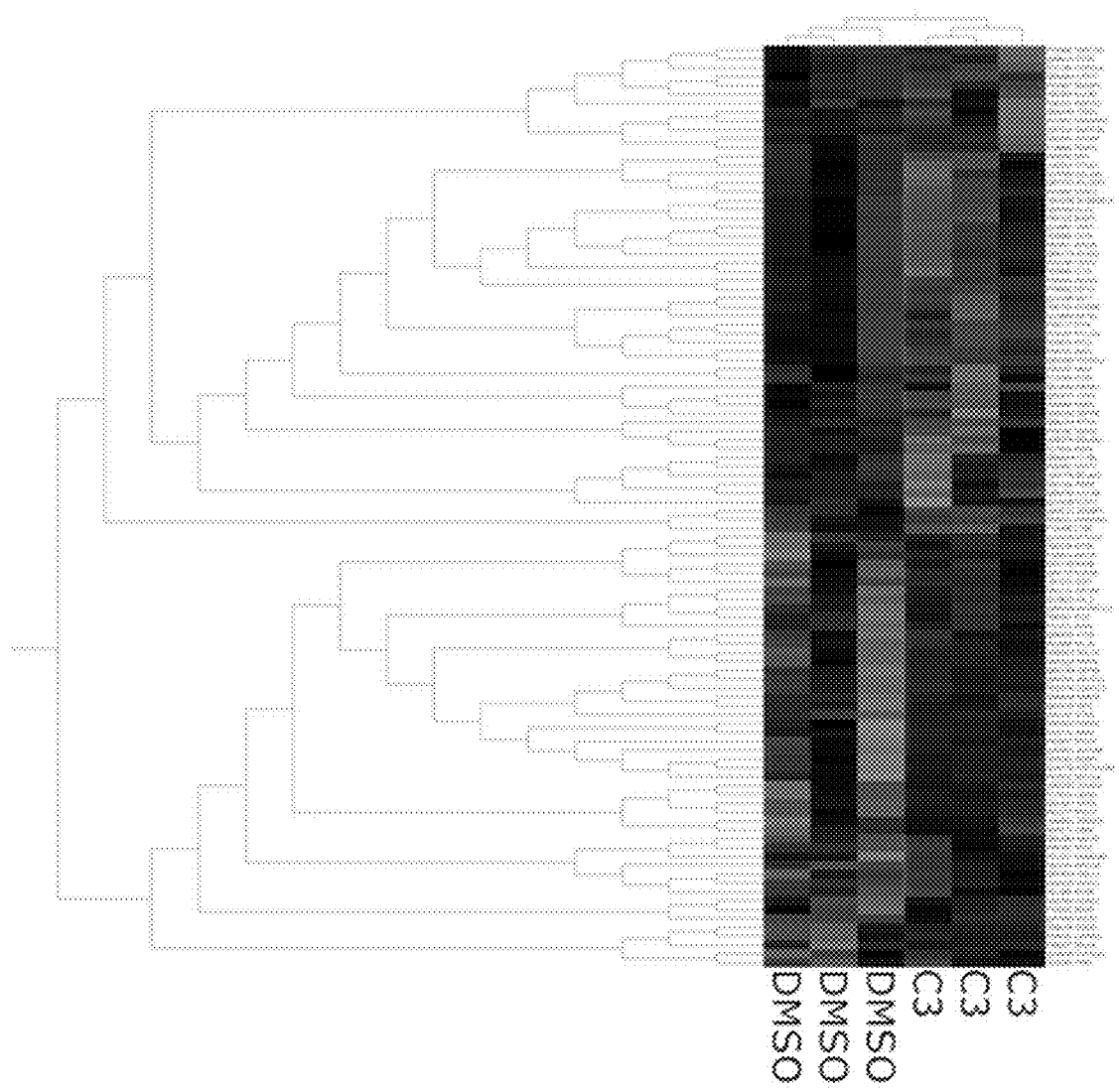
Figure 20C:
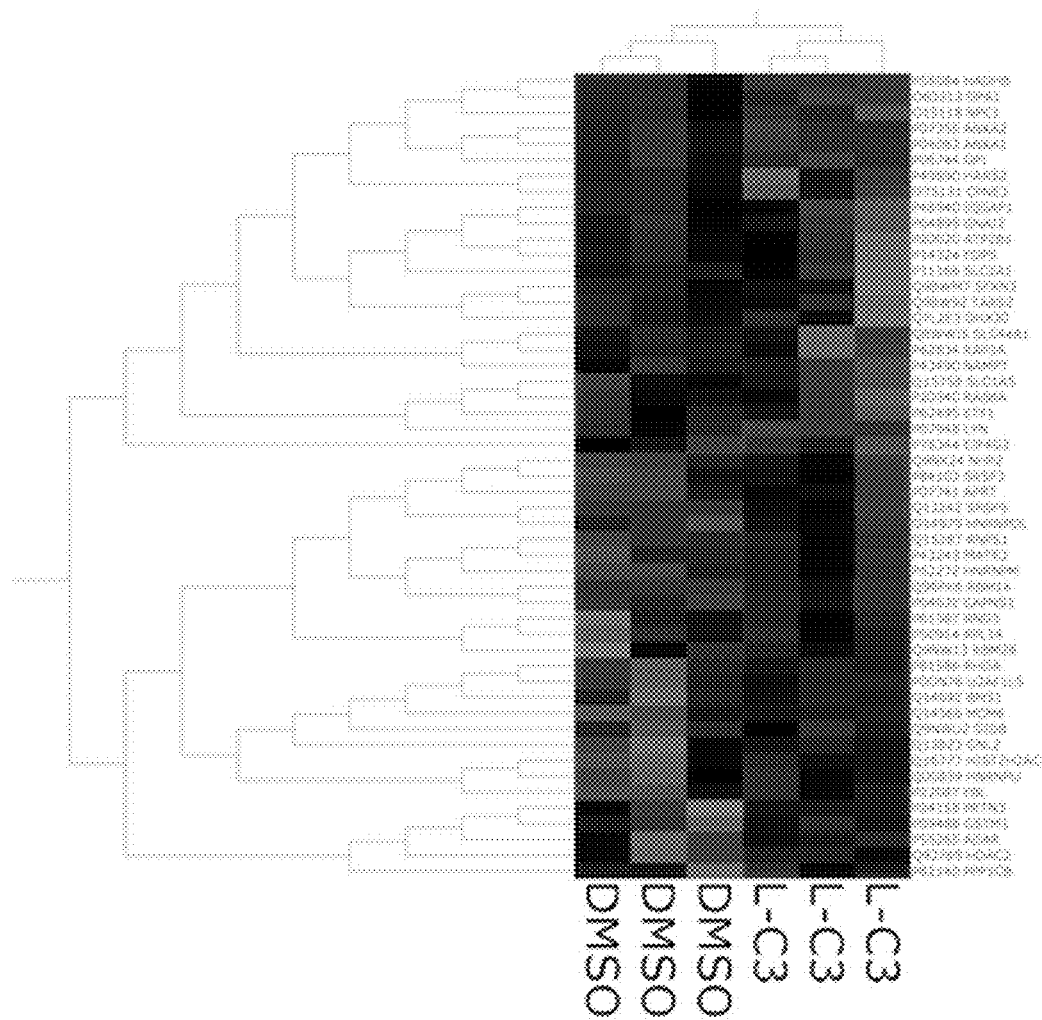
Figure 20D:
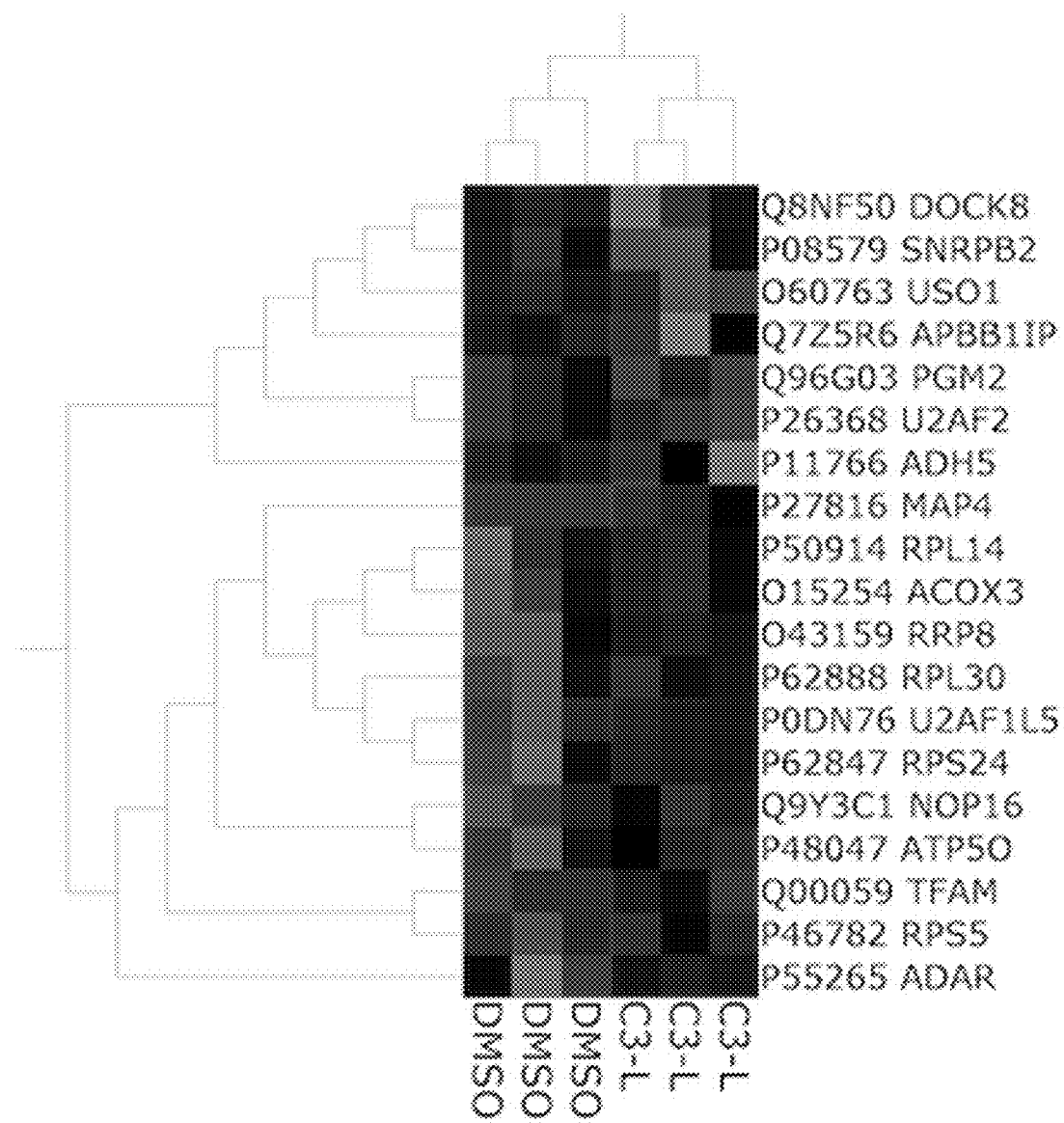

Using luciferase assay to test potential mechanisms of IL1beta gene expression regulation in the presence of Compound 3. See FIG. 19, where Glucocorticoid Receptor (GR), Activator Protein-1 (AP-1) showed as transrepressors of inflammatory genes such as IL-1β.

Example 16

FIG. 20 provided proteomics results of THP-1 monocytes in the presence of LPS stimulation, C3 treatment separately, and LPS stimulation before or after C3 compound treatment. The gene expression profile under these conditions may give suggestions how C3 act on immune system by interfering various signaling pathways.

Example 17

General Synthetic Procedures of Derivative Compounds (Derived from Compound C3)

Derivatives made based on parent compound C3 and their methods of making, characterization. In this Example, derivatives of C3 are made based on the following methods and characterized accordingly.

Method A.

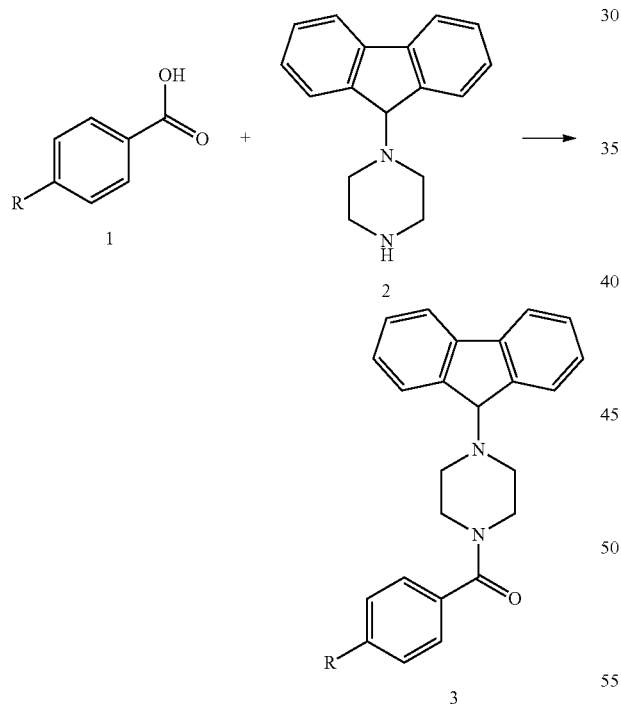

To a solution of acid (1) (1.0 equivalent) in CH$_2$Cl$_2$ (3 mL) was added HBTU (1.2 equivalent) and N,N-diisopropylethylamine (2.8 equivalent), and stirred the reaction mixture at 22° C. for 30 min. Added amine (2) (1.0 equivalent) and continued stirring for another 14 hours. After completion of reaction added sat. NaHCO$_3$ solution 50 mL and extracted aq. layer with dichloromethane (3×30 mL). The combined organic layer was dried over Na$_2$SO$_4$, filtered and evaporated solvent in vacuo to obtain crude. The crude product was purified by flash column chromatography (silica gel) to give compound 3.

Method B.

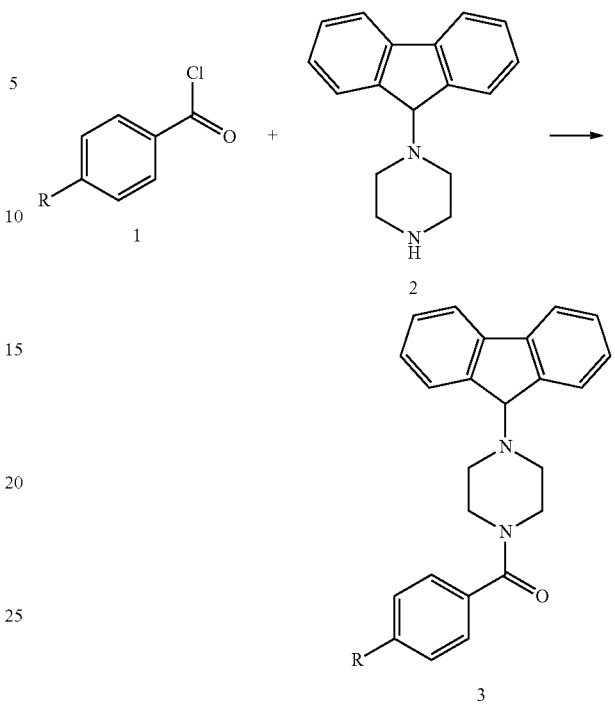

Acid chloride (1) (1.0 equivalent) and Et$_3$N (1.2 equivalent) were added to 1-(9H-fluoren-9-yl)piperazine (2) (0.98 equivalent) in CH$_2$Cl$_2$. After 2 h at 22° C., 50 mL of CH$_2$Cl$_2$ were added and the solution washed with H$_2$O (2×30 mL). The organic layer was dried over Na$_2$SO$_4$, filtered and evaporated solvent in vacuo to obtain crude. The crude product was purified by flash column chromatography (silica gel) to give compound 3.

Method C.

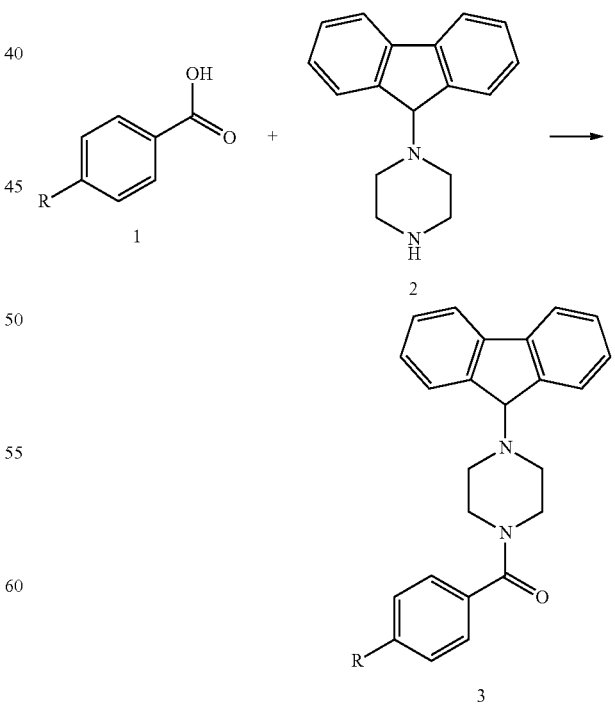

To a solution of acid (1) (1.0 equivalent) in CH$_2$Cl$_2$ (3 mL) was added pivaloyl chloride (1.0 equivalent) and Et$_3$N (1.2 equivalent), and stirred the reaction mixture at 22° C. for 30 min. Added 1-(9H-fluoren-9-yl)piperazine (2) (0.95 equivalent) and Et₃N (1.5 equivalent), and continued stirring for another 14 hours. After completion of reaction added sat. NaHCO₃ solution 50 mL and extracted aq. layer with dichloromethane (3×30 mL). The combined organic layer was dried over Na₂SO₄, filtered and evaporated solvent in vacuo to obtain crude. The crude product was purified by flash column chromatography (silica gel) to give compound 3.

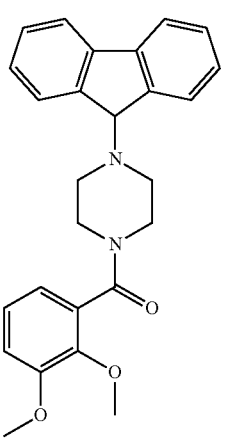

DBGI-196

Synthetic Procedure—Method C.
Notebook reference: DYGI-196
Yield—180 mg (55.74%)
¹H NMR (500 MHz, Chloroform-d) δ 7.68 (dd, J=7.5, 2.5 Hz, 2H), 7.61 (dd, J=11.4, 7.4 Hz, 2H), 7.37 (t, J=7.5 Hz, 2H), 7.28 (td, J=7.4, 1.1 Hz, 2H), 7.04 (t, J=7.9 Hz, 1H), 6.89 (dd, J=8.2, 1.5 Hz, 1H), 6.78 (dd, J=7.7, 1.5 Hz, 1H), 4.86 (s, 1H), 3.85 (s, 3H), 3.81 (s, 3H), 3.73 (ddd, J=12.9, 6.7, 3.8 Hz, 2H), 3.21 (dddd, J=50.1, 12.8, 6.8, 3.0 Hz, 2H), 2.73 (dqd, J=11.1, 7.4, 6.3, 2.2 Hz, 2H), 2.52 (dddd, J=79.1, 10.7, 6.8, 3.1 Hz, 2H).
¹³C NMR (126 MHz, Chloroform-d) δ 167.49, 152.66, 145.03, 143.70, 143.60, 141.21, 141.13, 131.41, 128.38, 127.24, 127.16, 126.03, 125.92, 124.83, 119.94, 119.44, 112.90, 70.12, 61.64, 55.93, 49.30, 49.13, 47.97, 42.62.
HRMS (M+H): Calc. 415.1943, Observed 415.3203

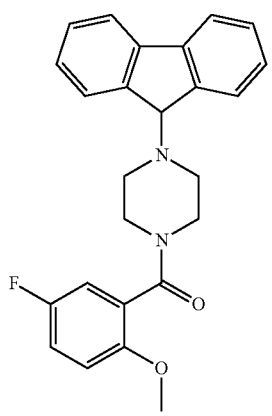

DBGI-199

Synthetic Procedure—Method C.
Notebook reference: DYGI-199
Yield—100 mg (44.49%)
¹H NMR (500 MHz, Chloroform-d) δ 7.68 (dt, J=7.5, 0.9 Hz, 2H), 7.61 (d, J=7.4 Hz, 2H), 7.38 (t, J=7.4 Hz, 2H), 7.35-7.27 (m, 2H), 6.98 (ddd, J=9.0, 7.9, 3.1 Hz, 1H), 6.92 (dd, J=7.9, 3.1 Hz, 1H), 6.78 (dd, J=9.0, 4.1 Hz, 1H), 4.87 (s, 1H), 3.91-3.74 (m, 2H), 3.73 (s, 3H), 3.17 (dt, J=9.7, 4.7 Hz, 2H), 2.95-2.70 (m, 2H), 2.56-2.24 (m, 2H).
¹³C NMR (126 MHz, Chloroform-d) δ 166.35, 157.92, 156.01, 151.54, 143.56, 141.18, 128.43, 127.25, 127.22, 126.98, 125.98, 119.96, 116.56, 116.38, 115.20, 115.00, 112.13, 112.07, 56.19, 49.59, 48.56, 47.69, 42.69.
HRMS (M+H): Calc. 403.1714, Observed 403.2923

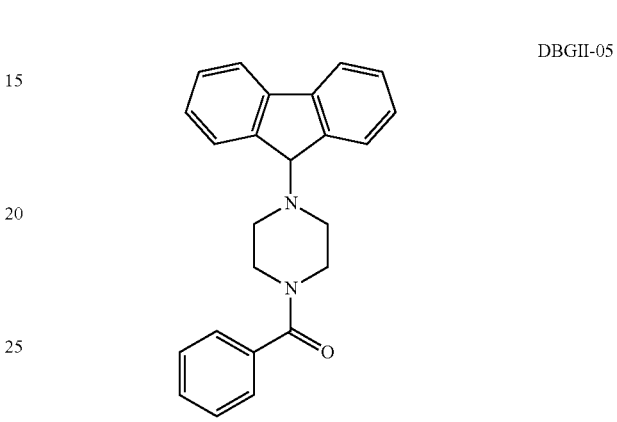

DBGII-05

Synthetic Procedure—Method B.
Notebook reference: DYGII-05
Yield—50 mg (17.65%)
¹H NMR (500 MHz, Chloroform-d) δ 7.60 (dt, J=7.6, 0.9 Hz, 2H), 7.53 (dq, J=7.5, 0.9 Hz, 2H), 7.33-7.26 (m, 3H), 7.26 (d, J=3.0 Hz, 4H), 7.21 (td, J=7.4, 1.2 Hz, 2H), 4.79 (s, 1H), 3.71 (s, 2H), 3.26 (s, 2H), 2.76 (s, 2H), 2.33 (s, 2H).
¹³C NMR (126 MHz, Chloroform-d) δ 170.42, 143.53, 141.16, 135.98, 129.68, 128.49, 128.43, 127.28, 127.17, 126.00, 119.96, 70.08, 49.70, 48.77, 48.62, 43.06.
HRMS (M+H): Calc. 355.1732, Observed 355.2984

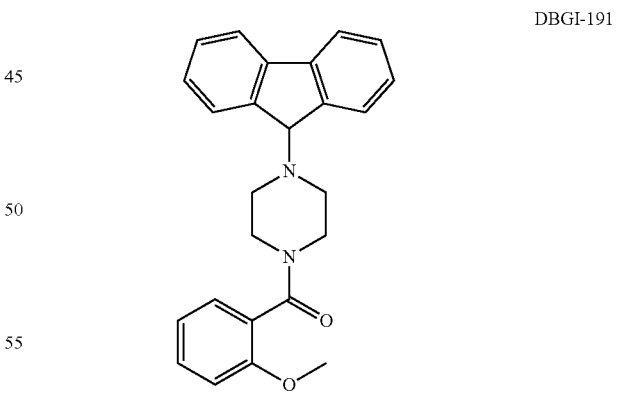

DBGI-191

Synthetic Procedure—Method B.
Notebook reference: DBGI-191
Yield—35 mg (22.78%)
¹H NMR (500 MHz, Chloroform-d) δ 7.65 (d, J=7.5 Hz, 2H), 7.59 (d, J=7.5 Hz, 2H), 7.34 (t, J=7.4 Hz, 2H), 7.27 (d, J=1.4 Hz, 1H), 7.24 (d, J=7.2 Hz, 1H), 7.15 (dd, J=7.4, 1.7 Hz, 1H), 6.94-6.84 (m, 1H), 6.81 (d, J=8.3 Hz, 1H), 4.84 (s, 1H), 3.96-3.74 (m, 2H), 3.72 (s, 3H), 3.14 (dq, J=9.5, 5.1, 4.5 Hz, 2H), 2.88-2.71 (m, 2H), 2.49-2.19 (m, 2H).

¹³C NMR (126 MHz, Chloroform-d) δ 167.87, 155.37, 143.65, 141.16, 130.38, 128.37, 128.04, 127.19, 125.99, 125.93, 120.95, 119.93, 110.89, 70.13, 55.53, 49.68, 48.58, 47.69, 42.61.
HRMS (M+H): Calc. 385.1838, Observed 385.3795

¹³C NMR (126 MHz, Chloroform-d) δ 165.78, 147.66, 144.01, 143.57, 141.15, 128.42, 127.27, 126.01, 122.05, 121.10, 119.95, 117.77, 109.74, 101.35, 70.09, 49.61, 48.82, 48.07, 43.00.
HRMS (M+H): Calc. 399.1630, Observed 399.1723

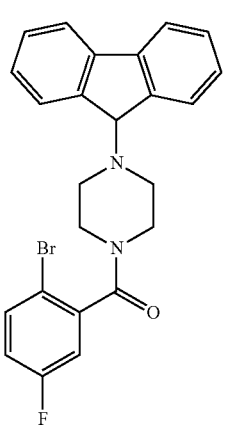

DBGII-04

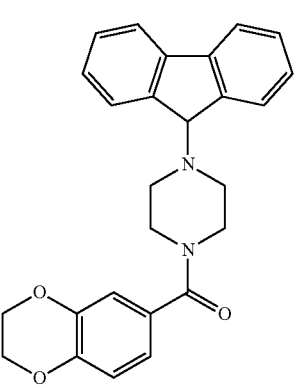

DBGII-02

Synthetic Procedure—Method C.
Notebook reference: DBGII-04
Yield—70 mg (28.70%)
¹H NMR (500 MHz, Chloroform-d) δ 7.68 (ddd, J=7.6, 2.1, 1.1 Hz, 2H), 7.60 (ddd, J=7.3, 2.3, 1.1 Hz, 2H), 7.49 (ddd, J=8.4, 4.9, 0.7 Hz, 1H), 7.43-7.34 (m, 2H), 7.29 (tdd, J=7.4, 2.2, 1.2 Hz, 2H), 7.02-6.83 (m, 2H), 4.87 (s, 1H), 4.07-3.59 (m, 2H), 3.18 (dddd, J=44.2, 12.8, 6.8, 3.2 Hz, 2H), 2.81 (dddd, J=45.0, 11.1, 6.9, 3.4 Hz, 2H), 2.50 (dddd, J=85.6, 11.0, 6.8, 3.3 Hz, 2H).
¹³C NMR (126 MHz, Chloroform-d) δ 166.41, 162.94, 160.95, 143.47, 143.36, 141.20, 141.13, 139.69, 134.51, 134.44, 128.50, 127.33, 127.29, 125.96, 125.89, 120.03, 119.97, 117.77, 117.59, 115.35, 115.16, 113.57, 77.41, 77.16, 76.91, 70.08, 49.18, 48.72, 47.63, 42.64, 1.17.
HRMS (M+H): Calc. 451.0743, Observed 453.0976

Synthetic Procedure—Method C.
Notebook reference: DBGII-02
Yield—120 mg (44.13%)
¹H NMR (500 MHz, Chloroform-d) δ 7.68 (dt, J=7.6, 0.9 Hz, 2H), 7.61 (dd, J=7.4, 1.0 Hz, 2H), 7.44-7.33 (m, 2H), 7.29 (td, J=7.4, 1.2 Hz, 2H), 6.90 (d, J=1.9 Hz, 1H), 6.88-6.77 (m, 2H), 4.87 (s, 1H), 4.23 (h, J=1.3 Hz, 4H), 3.57 (d, J=160.7 Hz, 4H), 2.61 (d, J=163.3 Hz, 4H).
¹³C NMR (126 MHz, Chloroform-d) δ 169.89, 144.90, 143.55, 143.35, 141.14, 129.04, 128.40, 127.27, 126.01, 120.84, 119.93, 117.23, 116.86, 70.07, 64.55, 64.39.
HRMS (M+H): Calc. 413.1787, Observed 413.2651

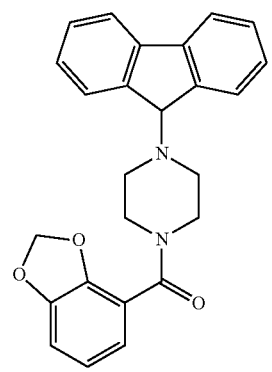

DBGI-200

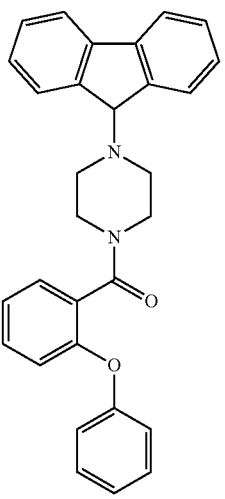

DBGI-195

Synthetic Procedure—Method C.
Notebook reference: DBGI-200
Yield—70 mg (30.75%)
¹H NMR (500 MHz, Chloroform-d) δ 7.68 (dt, J=7.5, 0.9 Hz, 2H), 7.61 (dq, J=7.4, 1.0 Hz, 2H), 7.38 (tt, J=7.4, 0.9 Hz, 2H), 7.29 (td, J=7.5, 1.2 Hz, 2H), 6.96-6.62 (m, 3H), 5.95 (s, 2H), 4.87 (s, 1H), 3.79 (s, 2H), 3.35 (t, J=5.0 Hz, 2H), 2.83 (t, J=5.0 Hz, 2H), 2.45 (t, J=4.9 Hz, 2H).

Synthetic Procedure—Method C.
Notebook reference: DBGI-195
Yield—150 mg (50.49%)
¹H NMR (500 MHz, Chloroform-d) δ 7.68 (d, J=7.5 Hz, 2H), 7.58 (d, J=7.5 Hz, 1H), 7.51 (d, J=7.5 Hz, 1H), 7.40-7.28 (m, 5H), 7.28-7.26 (m, 1H), 7.26-7.20 (m, 1H), 7.10 (tdd, J=7.3, 2.6, 1.1 Hz, 2H), 6.97-6.90 (m, 2H), 6.85 (dd, J=8.3, 1.0 Hz, 1H), 4.84 (s, 1H), 3.73 (dt, J=11.2, 5.0 Hz, 2H), 3.50-3.15 (m, 2H), 2.72 (t, J=5.1 Hz, 2H), 2.67-2.47 (m, 1H), 2.41 (t, J=8.9 Hz, 1H).

¹³C NMR (126 MHz, Chloroform-d) δ 166.98, 156.68, 152.84, 143.53, 141.17, 130.51, 129.89, 128.82, 128.43, 128.36, 127.19, 126.01, 123.82, 123.69, 119.91, 118.90, 118.44, 77.41, 77.16, 76.91, 70.10, 49.36, 48.88, 47.91, 42.64, 1.17.

HRMS (M+H): Calc. 447.1994, Observed 447.2909

DBGII-01

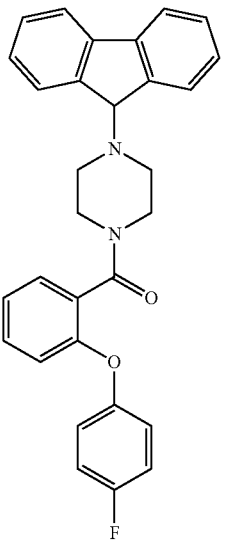

Synthetic Procedure—Method C.
Notebook reference: DBGII-01
Yield—100 mg (52.64%)
¹H NMR (500 MHz, Chloroform-d) δ 7.68 (d, J=7.5 Hz, 2H), 7.56 (dd, J=12.5, 7.4 Hz, 2H), 7.37 (td, J=7.2, 3.4 Hz, 2H), 7.31 (dd, J=7.5, 1.7 Hz, 1H), 7.27 (dd, J=7.2, 1.5 Hz, 1H), 7.26-7.20 (m, 2H), 7.10 (td, J=7.5, 1.0 Hz, 1H), 7.04-6.95 (m, 2H), 6.92-6.85 (m, 2H), 6.79 (dd, J=8.3, 0.9 Hz, 1H), 4.85 (s, 1H), 3.75 (dt, J=10.2, 5.0 Hz, 2H), 3.29 (ddd, J=22.7, 6.7, 3.7 Hz, 2H), 2.77 (t, J=5.1 Hz, 2H), 2.66-2.18 (m, 2H).
¹³C NMR (126 MHz, Chloroform-d) δ 166.92, 160.00, 158.08, 153.15, 152.48, 143.53, 141.17, 130.56, 128.76, 128.40, 128.22, 127.22, 125.99, 123.84, 120.43, 120.37, 119.94, 117.92, 116.54, 116.35, 70.08, 49.61, 48.64, 47.89, 42.68.

HRMS (M+H): Calc. 465.1900, Observed 465.3101

DBGII-09

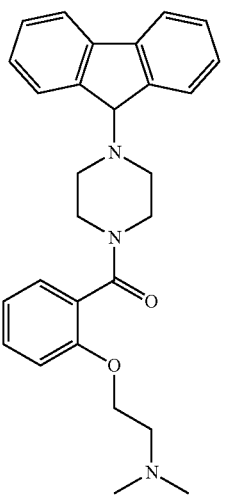

Synthetic Procedure—Method A.
Notebook reference: DBGII-09
Yield—75 mg (33.38%)
¹H NMR (500 MHz, Chloroform-d) δ 7.68 (dt, J=7.6, 0.9 Hz, 2H), 7.61 (d, J=7.4 Hz, 2H), 7.37 (t, J=7.4 Hz, 2H), 7.32-7.26 (m, 3H), 7.18 (dd, J=7.5, 1.8 Hz, 1H), 6.94 (td, J=7.4, 0.9 Hz, 1H), 6.85 (dd, J=8.4, 0.9 Hz, 1H), 4.87 (s, 1H), 4.05 (t, J=6.1 Hz, 2H), 3.94-3.60 (m, 2H), 3.34-3.05 (m, 2H), 2.92-2.72 (m, 2H), 2.68 (td, J=6.1, 1.1 Hz, 2H), 2.48-2.34 (m, 2H), 2.31 (s, 6H).
¹³C NMR (126 MHz, Chloroform-d) δ 167.84, 154.49, 143.61, 141.16, 130.38, 128.39, 128.10, 127.27, 127.22, 126.40, 125.97, 121.27, 119.94, 112.23, 70.09, 67.27, 58.03, 49.63, 48.73, 47.72, 46.21, 42.50.

HRMS (M+H): Calc. 442.2416, Observed 442.3809

DBGI-197

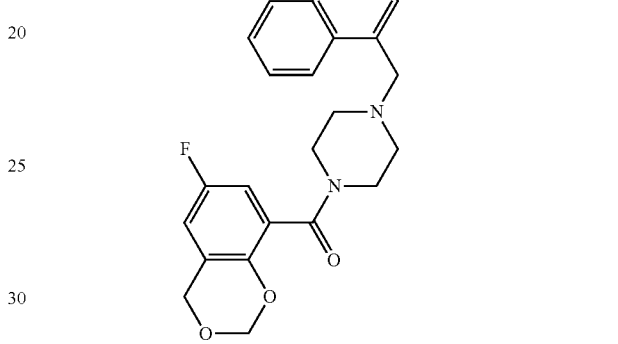

Synthetic Procedure—Method C.
Notebook reference: DBGI-197
Yield—340 mg (87.18%)
¹H NMR (500 MHz, Chloroform-d) δ 8.46-8.17 (m, 1H), 7.97-7.71 (m, 2H), 7.61-7.44 (m, 2H), 7.46-7.35 (m, 2H), 6.90 (ddt, J=8.1, 3.0, 0.8 Hz, 1H), 6.71 (ddt, J=8.0, 3.0, 1.0 Hz, 1H), 5.36-5.09 (m, 2H), 5.01-4.77 (m, 2H), 3.93 (d, J=2.1 Hz, 2H), 3.78 (d, J=62.9 Hz, 2H), 3.30 (dt, J=24.4, 5.7 Hz, 2H), 2.79-2.27 (m, 4H).
¹³C NMR (126 MHz, Chloroform-d) δ 165.35, 157.90, 155.97, 144.72, 134.00, 133.50, 132.57, 128.57, 128.37, 127.67, 126.57, 126.52, 125.94, 125.83, 125.20, 124.81, 122.96, 122.91, 113.92, 113.72, 112.74, 112.55, 91.54, 77.41, 77.16, 76.91, 66.01, 61.22, 53.47, 53.00, 47.11, 42.01.

HRMS (M+H): Calc. 407.1693, Observed 407.3178

DBGII-11

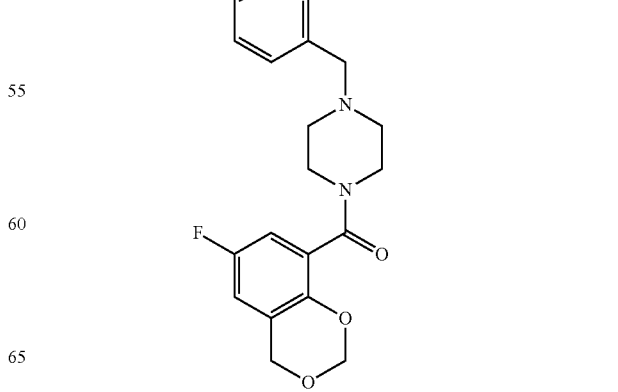

Synthetic Procedure—Method C.
Notebook reference: DBGII-11
Yield—100 mg (29.43%)
$^1$H NMR (500 MHz, Chloroform-d) δ 7.31 (d, J=5.3 Hz, 5H), 6.89 (dd, J=8.1, 3.0 Hz, 1H), 6.71 (dd, J=8.1, 2.9 Hz, 1H), 5.35-5.13 (m, 2H), 4.87 (q, J=14.6 Hz, 2H), 3.89-3.69 (m, 2H), 3.41-3.24 (m, 2H), 2.59-2.30 (m, 4H).
$^{13}$C NMR (126 MHz, Chloroform-d) δ 165.37, 157.91, 155.98, 144.73, 137.74, 129.22, 128.46, 127.41, 126.56, 126.51, 122.97, 122.91, 113.93, 113.73, 112.75, 112.57, 91.55, 66.03, 62.98, 53.33, 52.75, 47.07, 41.94.
HRMS (M+H): Calc. 357.1536, Observed 357.2724

DBGI-190

Synthetic Procedure—Method B.
Notebook reference: DBGI-190
Yield—80 mg (55.72%)
$^1$H NMR (500 MHz, Chloroform-d) δ 7.69 (d, J=7.5 Hz, 2H), 7.61 (d, J=7.5 Hz, 2H), 7.38 (t, J=7.5 Hz, 2H), 7.31 (q, J=7.4, 6.9 Hz, 3H), 7.11 (d, J=7.6 Hz, 1H), 7.06 (d, J=8.4 Hz, 2H), 4.88 (s, 1H), 3.78 (s, 2H), 3.33 (s, 2H), 2.84 (s, 2H), 2.43 (s, 2H).
$^{13}$C NMR (126 MHz, Chloroform-d) δ 168.91, 163.58, 161.61, 143.43, 141.17, 138.06, 138.01, 130.35, 130.29, 128.49, 127.32, 125.99, 122.83, 119.99, 116.81, 116.64, 114.57, 114.39 70.05, 49.60, 48.79, 48.56, 43.13.
HRMS (M+H): Calc. 373.1678, Observed 373.3588

DBGII-03

Synthetic Procedure—Method C.
Notebook reference: DBGII-03
Yield—100 mg (40.53%)
$^1$H NMR (500 MHz, Chloroform-d) δ 8.39 (d, J=4.8 Hz, 1H), 8.25 (s, 1H), 7.68 (d, J=7.5 Hz, 2H), 7.65-7.46 (m, 2H), 7.45-7.29 (m, 4H), 7.27 (d, J=4.4 Hz, 1H), 7.26 (d, J=2.7 Hz, 2H), 7.20-7.09 (m, 1H), 6.95 (dd, J=7.7, 1.5 Hz, 2H), 4.84 (s, 1H), 3.71 (q, J=6.8, 4.8 Hz, 2H), 3.27 (d, J=22.4 Hz, 2H), 2.72 (t, J=5.1 Hz, 2H), 2.50 (d, J=57.5 Hz, 2H).
$^{13}$C NMR (126 MHz, Chloroform-d) δ 164.52, 156.20, 148.90, 145.22, 143.37, 141.40, 141.18, 135.50, 130.17, 128.48, 127.27, 125.95, 124.42, 122.47, 119.99, 118.59, 70.05, 49.24, 48.79, 47.83, 42.67.
HRMS (M+H): Calc. 448.1947, Observed 448.2688

DBGII-14

Synthetic Procedure—Method B.
Notebook reference: DBGII-14
Yield—110 mg (27.46%)
$^1$H NMR (500 MHz, Chloroform-d) δ 7.68 (d, J=7.5 Hz, 2H), 7.65-7.56 (m, 2H), 7.38 (t, J=7.5 Hz, 2H), 7.29 (t, J=7.5 Hz, 2H), 7.25-7.22 (m, 1H), 7.17 (d, J=2.6 Hz, 1H), 6.77 (d, J=8.8 Hz, 1H), 4.86 (s, 1H), 3.74 (s, 5H), 3.30-3.06 (m, 2H), 2.95-2.64 (m, 2H), 2.56-2.19 (m, 2H).
$^{13}$C NMR (126 MHz, Chloroform-d) δ 166.23, 154.00, 143.56, 141.17, 130.08, 128.43, 128.00, 127.41, 127.26, 127.20, 126.04, 125.98, 119.97, 112.22, 70.11, 55.92, 49.58, 48.58, 47.69, 42.69.
HRMS (M+H): Calc. 419.1448, Observed 419.3161

DBGII-54

Synthetic Procedure—Method C.
Notebook reference: DBGII-54
Yield—290 mg (69.95%)
$^1$H NMR (500 MHz, Chloroform-d) δ 7.40 (t, J=5.3 Hz, 4H), 7.32-7.26 (m, 4H), 7.18 (t, J=7.4 Hz, 2H), 6.93-6.82 (m, 1H), 6.69 (ddd, J=8.0, 3.0, 1.0 Hz, 1H), 5.28-5.07 (m, 2H), 5.02-4.63 (m, 2H), 4.26 (s, 1H), 3.79 (d, J=47.3 Hz, 2H), 3.48-3.19 (m, 2H), 2.73-2.18 (m, 4H).
$^{13}$C NMR (126 MHz, CDCl$_3$) δ 165.18, 157.76, 155.84, 144.57, 142.12, 128.62, 127.83, 127.17, 126.47, 126.42, 122.79, 122.73, 113.78, 113.58, 112.56, 112.37, 91.41, 77.28, 77.03, 76.78, 75.90, 65.88, 52.07, 51.51, 47.13, 41.97.
HRMS (M+H): Calc. 432.1849, Observed

DBGII-55

Synthetic Procedure—Method C.
Notebook reference: DBGII-55
Yield—320 mg (71.35%)
$^1$H NMR (500 MHz, Chloroform-d) δ 7.34 (t, J=4.5 Hz, 4H), 6.97 (t, J=8.5 Hz, 4H), 6.87 (dd, J=8.2, 3.0 Hz, 1H), 6.69 (dd, J=8.0, 3.0 Hz, 1H), 5.31-5.10 (m, 2H), 4.97-4.75 (m, 2H), 4.25 (s, 1H), 3.97-3.67 (m, 2H), 3.32 (dt, J=32.4, 6.4 Hz, 2H), 2.61-2.10 (m, 4H).
$^{13}$C NMR (126 MHz, CDCl$_3$) δ 165.33, 163.02, 161.07, 157.91, 155.98, 144.71, 137.76, 129.35, 129.28, 126.47, 126.42, 122.97, 122.91, 115.80, 115.63, 113.92, 113.72, 112.78, 112.59, 91.55, 77.41, 77.16, 76.91, 74.37, 66.01, 52.10, 51.51, 47.18, 42.01.
HRMS (M+H): Calc. 468.1661, Observed

DBGII-67

Synthetic Procedure—Method A.
Notebook reference: DBGII-67
Yield—100 mg (26.28%)

$^1$H NMR (500 MHz, Chloroform-d) δ 7.67 (dt, J=7.6, 1.0 Hz, 2H), 7.61 (d, J=7.4 Hz, 2H), 7.54 (dd, J=6.9, 2.1 Hz, 1H), 7.37 (t, J=7.4 Hz, 2H), 7.28 (dd, J=7.4, 1.2 Hz, 2H), 7.16 (dd, J=6.5, 2.1 Hz, 1H), 6.25 (t, J=6.7 Hz, 1H), 4.86 (s, 1H), 3.80 (d, J=5.1 Hz, 2H), 3.26 (s, 2H), 2.89 (d, J=5.1 Hz, 2H), 2.42 (s, 2H).
$^{13}$C NMR (126 MHz, CDCl$_3$) δ 165.62, 161.83, 143.63, 141.17, 136.31, 128.37, 128.14, 127.24, 126.06, 119.92, 106.73, 70.10, 49.94, 48.33, 47.91, 42.91.
HRMS (M+H): Calc. 372.4400, Observed 372.1706.

DBGII-64

Synthetic Procedure—Method A.
Notebook reference: DBGII-64
Yield—180 mg (38.98%)
$^1$H NMR (500 MHz, Chloroform-d) δ 7.98 (s, 1H), 7.74 (dd, J=7.9, 1.2 Hz, 1H), 7.66 (dt, J=7.5, 0.9 Hz, 2H), 7.59 (dd, J=7.5, 1.0 Hz, 2H), 7.42-7.33 (m, 2H), 7.28 (dd, J=7.4, 1.2 Hz, 1H), 7.26-7.23 (m, 1H), 7.20 (t, J=7.7 Hz, 1H), 4.87 (s, 1H), 3.68 (s, 4H), 2.64 (s, 4H).
$^{13}$C NMR (126 MHz, CDCl$_3$) δ 168.43, 143.36, 141.68, 141.16, 128.48, 127.30, 125.99, 122.12, 121.67, 120.00, 70.00, 49.29.
HRMS (M+H): Calc. 395.4780, Observed 395.1868.

DBGII-69

Synthetic Procedure—Method A.
Notebook reference: DBGII-69
Yield—250 mg (65.41%)
$^1$H NMR (500 MHz, Chloroform-d) δ 8.06 (dd, J=5.0, 1.8 Hz, 1H), 7.69 (dt, J=7.6, 0.9 Hz, 2H), 7.61 (dd, J=7.5, 1.1 Hz, 2H), 7.39 (tdd, J=7.5, 1.2, 0.6 Hz, 2H), 7.35-7.27 (m, 3H), 6.60 (dd, J=7.5, 5.0 Hz, 1H), 5.27 (d, J=29.2 Hz, 2H), 4.89 (s, 1H), 3.59 (s, 4H), 2.65 (s, 4H).

$^{13}$C NMR (126 MHz, CDCl$_3$) δ 168.46, 156.98, 149.27, 143.24, 141.20, 136.80, 128.56, 127.35, 126.00, 120.04, 113.79, 112.94, 70.00, 49.31.

HRMS (M+H): 370.1794, Observed

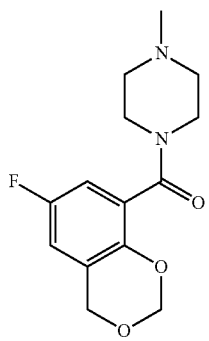

DBGI-194

Synthetic Procedure—Method C.

Notebook reference: DBGI-194

Yield—100 mg (35.32%)

$^1$H NMR (500 MHz, Chloroform-d) δ 6.90 (dd, J=8.2, 3.0 Hz, 1H), 6.73 (dt, J=8.0, 1.8 Hz, 1H), 5.45-5.10 (m, 2H), 4.88 (d, J=17.3 Hz, 2H), 3.80 (d, J=29.4 Hz, 2H), 3.33 (dt, J=25.9, 6.0 Hz, 2H), 2.46 (dt, J=42.8, 8.3 Hz, 3H), 2.31 (s, 4H).

$^{13}$C NMR (126 MHz, CDCl$_3$) δ 165.40, 157.92, 155.99, 144.73, 126.49, 126.44, 123.01, 122.95, 113.95, 113.75, 112.81, 112.62, 91.57, 66.04, 55.36, 54.75, 46.98, 46.19, 41.85.

HRMS (M+H): 281.1223, Observed 281.2029

Example 18. Screen of all the Derivatives Made in Example 17

Figure 22A:
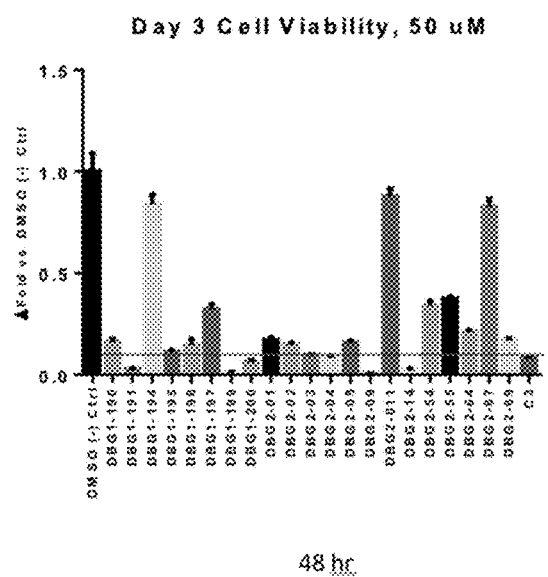
FIGS. 22A-22B. Screen of all the derivatives made in Example 17 in CCK8 cell viability assay with PC3 prostate cancer cell lines at day 3 (FIG. 22A) and day 5 (FIG. 22B).
Figure 22B:
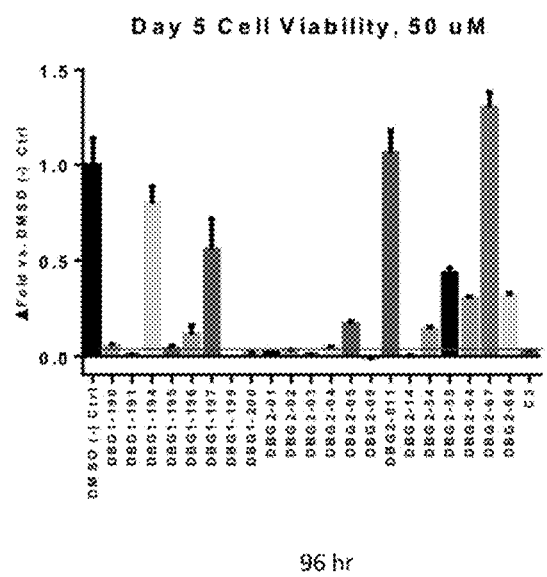
Figure 23:
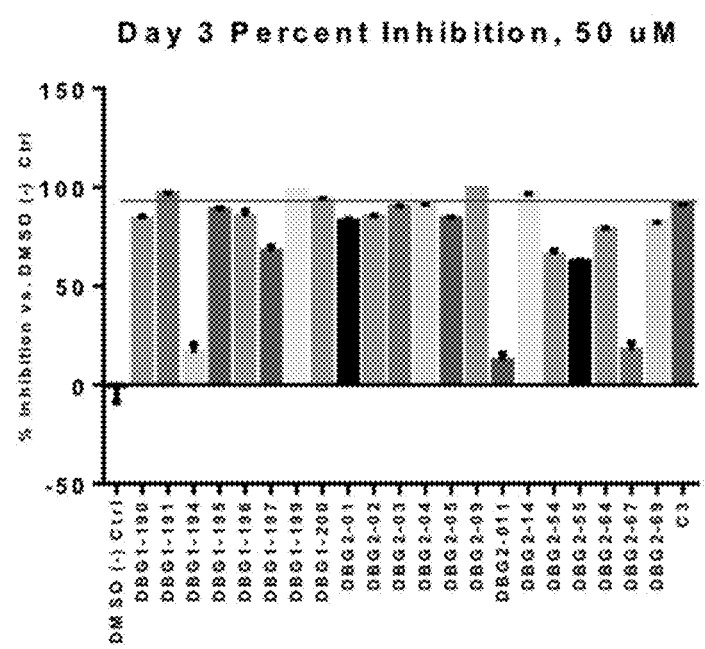
FIG. 23. All derivatives made in Example 17 are tested for cell inhibition percentage at day 3.

CCK8 cell viability assay with PC3 prostate cancer cell lines is conducted and cell viability on day 3, day 5 are examined, see FIGS. 22A-22B. Additionally, the cell inhibition percentage for compounds DBG1-191, 1-200, 02-09, 2-14, among others were further characterized in CCK8 assay against PC3. At day three of the assay, DBG-02-09 achieved the highest inhibition compared to all other derivatives. See FIG. 23.

Figure 24:
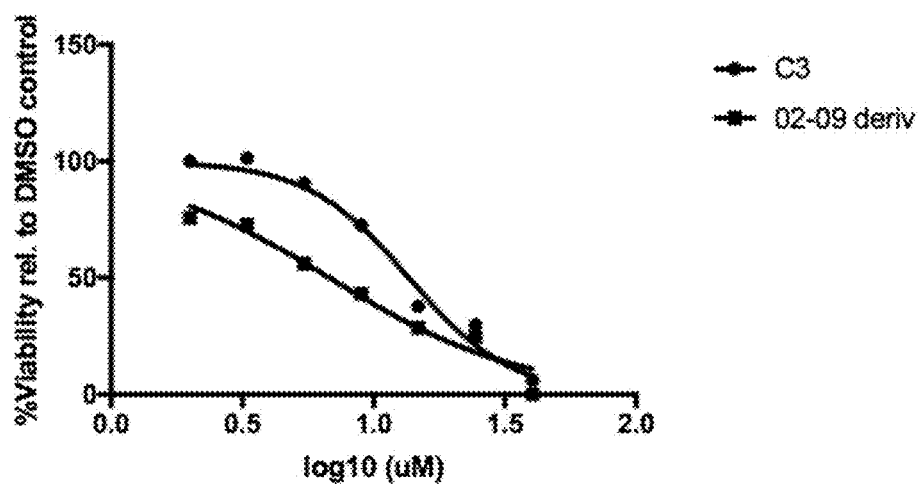
FIG. 24. The compounds DBG1-191, 1-200, 02-09, 2-14 were further characterized in CCK8 assay against C3. The one with best $IC_{50}$ reductions was derivative compound DBG-02-09 (also known as DBG-II-09 in the synthesis scheme of Example 17).

Example 19. Comparison Between the Best Derivative DBG-II-09 and Parental Compound C3. The Derivative has an Improvement in IC50. PC3 Cells were Used in a Cell Titer Glo (Promega) Cell Viability Assay In this series of cell viability experiments, we used the highly sensitive Cell Titer Glo reagents from Promega in PC3 prostate cancer cell line. We compared the parental compound C3 effect on reducing cell viability with the best derivative compound, DBG-02-09. We found that the compound 02-09 reduced the IC50 by 2.2 fold. See FIG. 24.

IC50 C3=16.7±7.6 uM

IC50 derivative 02–09=7.6±0.52 uM (p<0.05=significant difference detected in IC50 using paired t-test).

Figure 25:
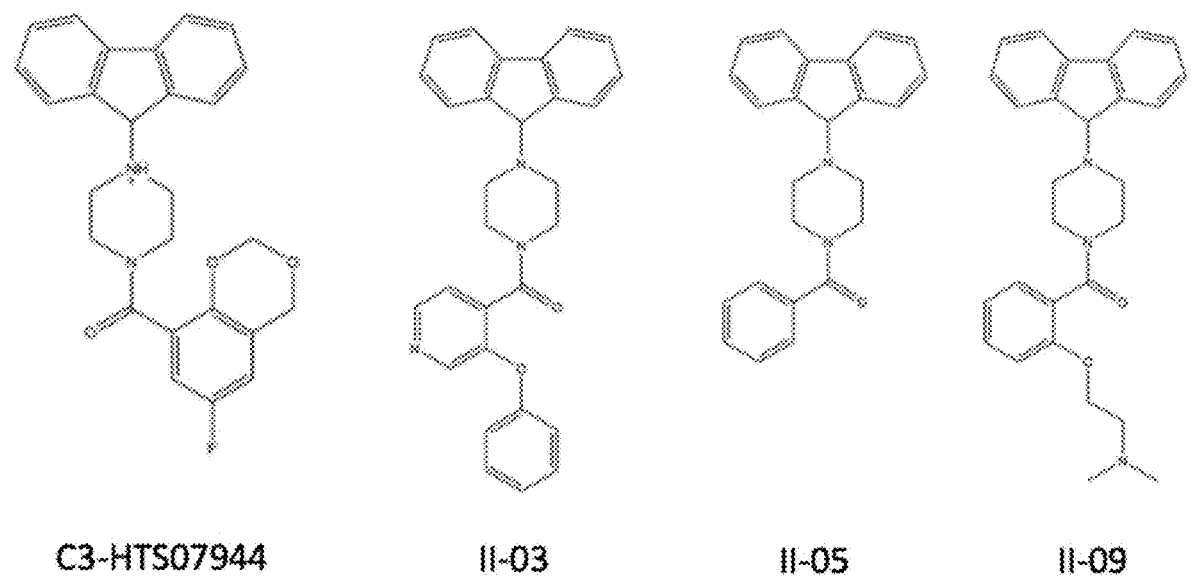
FIG. 25. Structure of C3 (original) and the derivatives 11-03, 11-05, and 11-09, the lead compounds FIGS. 26A-26C. Screening compounds for inhibition of prostate cancer cell line PC3 migration inhibition. PC3 migration in the presence of indicated compounds reported as wound width (μm).

Example 20. Structures of Top Performing Potential Inhibitors of Laminin Receptor Our current top performing potential inhibitors of the Laminin Receptor are 11-03, 11-05, and II-09 as lead compounds utilizing migration inhibition, cell viability and angiogenesis assays. FIG. 25 shows the structures of these compounds derived from our original hit, C3.

Example 21. Activity of Compounds Against Cancer Cell Migration

Figure 26A:
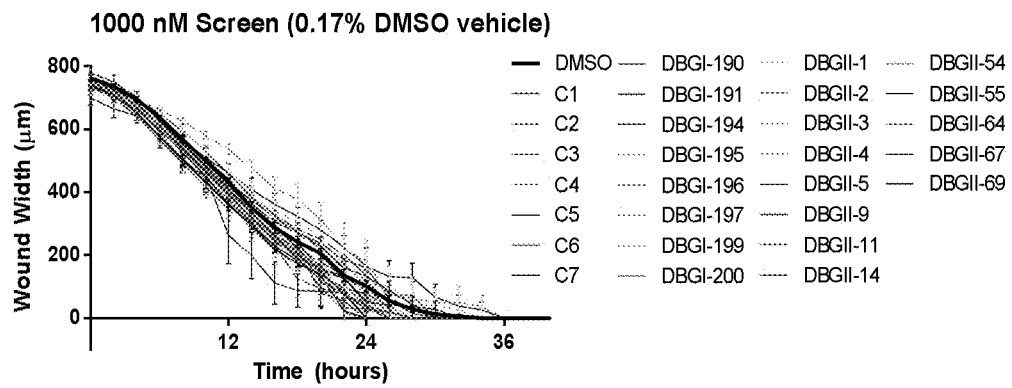
(FIG. 26A); The first 6 hours of top panel enlarged to show the changing wound width.
Figure 26B:
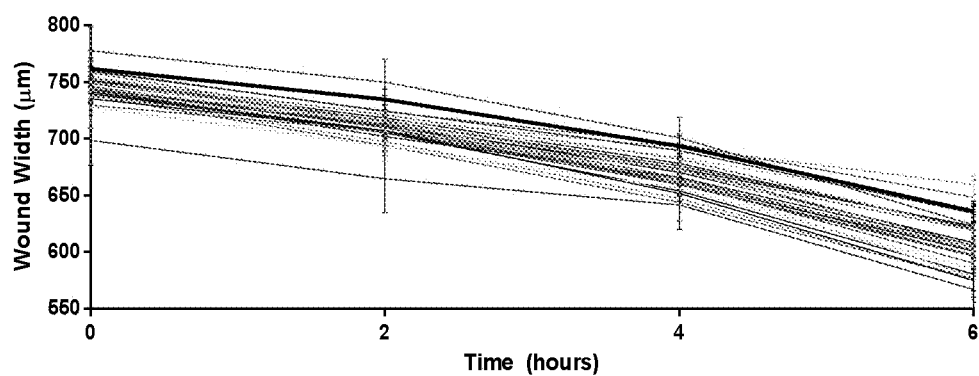
(FIG. 26B); The calculated rate of wound width change.
Figure 26C:
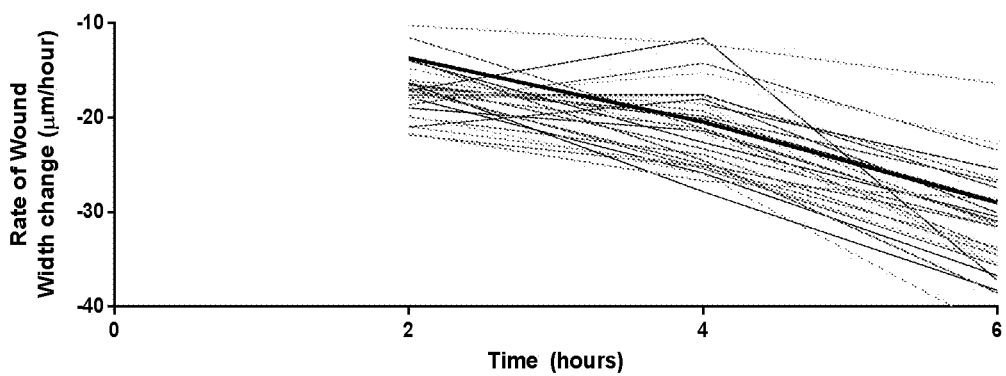
(FIG. 26C). Vehicle (DMSO=0.17%). compounds n=2; DMSO n=12.
Figure 27A:
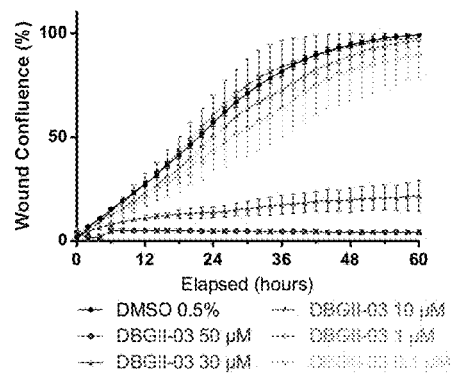
FIGS. 27A-27D. Examples of PC3 Migration (FIG. 27A) and Viability response (FIG. 27B) of DBGII-03 and Examples of PC3 Migration (FIG. 27C) and Viability response (FIG. 27D) of DBGII-09. Vehicle (DMSO=0.5%). n=2, DMSO n=16.
Figure 27C:
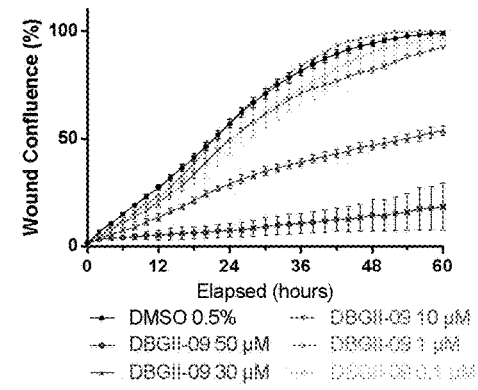
Figure 27B:
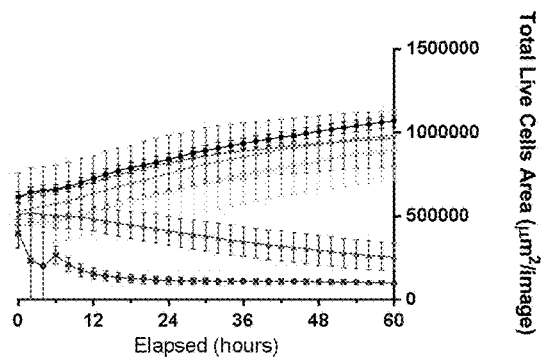
Figure 27D:
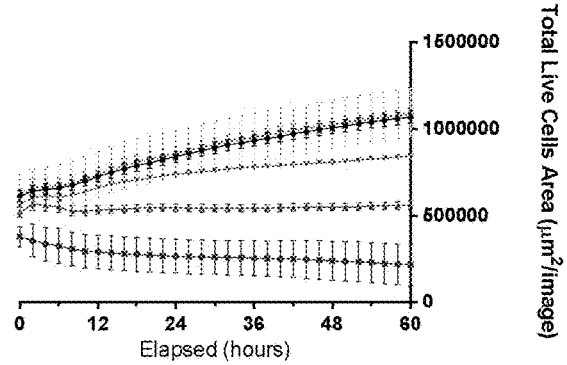
Figure 28A:
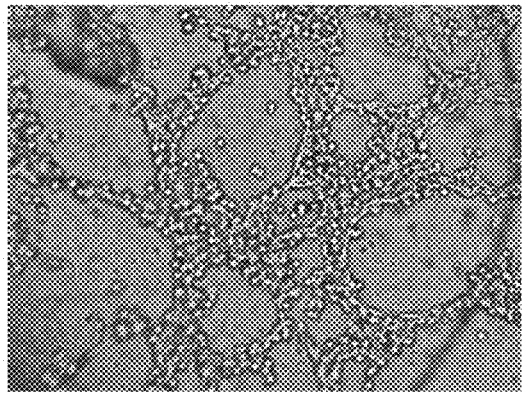
FIGS. 28A-28F Representative images of tube formation. 7 hour incubation period with respective compounds.
Figure 28B:
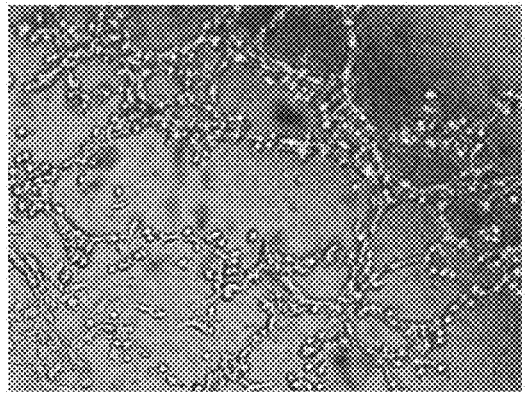
Figure 28C:
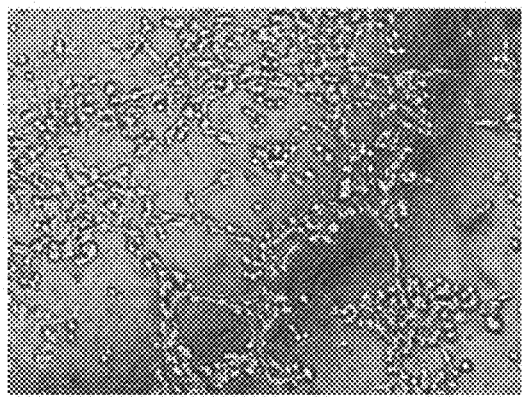
Figure 28D:
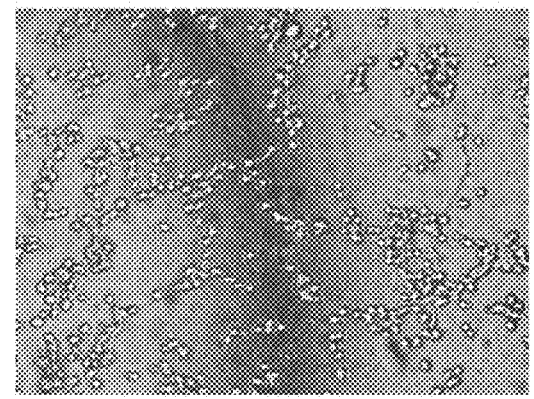
Figure 28E:
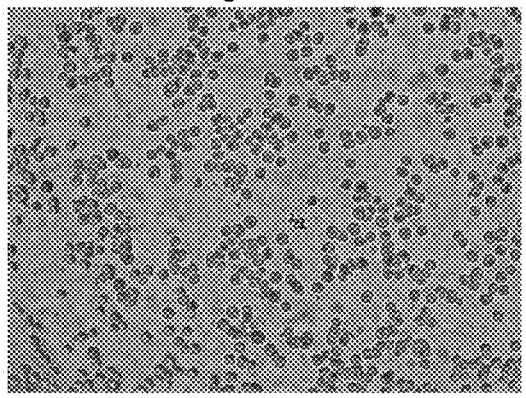
Figure 28F:
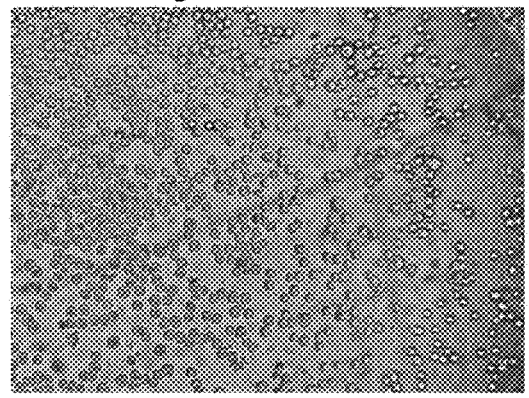

In FIGS. 26A-26C, we illustrate the results of a compound screen at 1 uM for a series of compound derivatives of C3. This screen used a migration assay (scratch assay) to examine compounds able to slow the rate of wound closure (i.e. reduce cancer cell migration) relative to vehicle control (DMSO). The data presents the rate of wound closure over the first 6 hours of the assay. We selected compounds that demonstrated the most favorable inhibition of migration, preferably over the first 6 hours in our selection process. Top compounds were further characterized in their ability to inhibit migration at a wider dose range of 50, 30, 10, 1 and 0.1 μM (FIGS. 27A-27D).

Example 23. Activity of Compounds Against Angiogenesis

An angiogenesis tube formation assay was used to characterize the impact of compounds against endothelial vessel formation in vitro (i.e., tube formation). Thinning of tubes formed was observed in DBGII-03, DBGII-05, and DBGII-09, which approximated the tube inhibition seen with the parent compound, C3 (FIGS. 28A-28F).

Example 24. General Procedure for Formation of 2-chloroethoxybenzoate

K$_2$CO$_3$ (181 mg, 1.314 mmol, 2 eq) was added to methyl salicylate or methyl 3-hydroxy benzoate or methyl 4-hydroxy benzoate (0.657 mmol, 1 eq) in 1 mL of methyl ethyl ketone in a pressure tube and was refluxed for 2.5 hrs. After 2.5 hrs, 1-bromo-2-chloroethane (206.69 mg, 2.2 eq) was added and refluxed for an additional 4 hrs. After 4 hours, additional K$_2$CO$_3$ (181 mg, 1.44 mmol, 2 eq.) and 1-bromo-2-chloroethane (93.9 mg, 0.657 mmol, 1 eq) were added. This process was repeated until reaction was completed via TLC. The reaction was allowed to cool to room temperature and solid filtered off. The filtrate was then diluted with hexanes and washed with water. Organic layers were combined, dried over anhydrous sodium sulphate, filtered and concentrated in vacuo Methyl 2-(2-chloroethoxy)benzoate

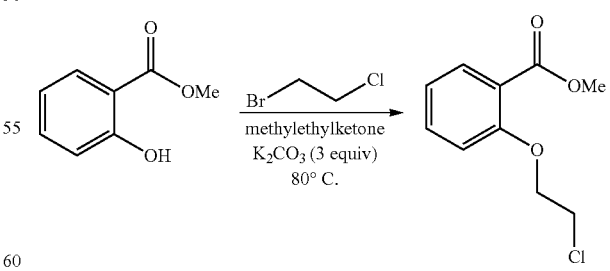

$^1$H NMR (500 MHz, Chloroform-d) δ 7.77 (dt, J=7.8, 1.7 Hz, 1H), 7.54-7.38 (m, 1H), 7.00 (tq, J=7.5, 1.2 Hz, 1H), 6.94 (dq, J=8.4, 1.4 Hz, 1H), 4.26 (ddd, J=8.0, 4.7, 1.6 Hz, 2H), 3.86 (t, J=1.4 Hz, 3H), 3.81 (tt, J=6.0, 1.4 Hz, 2H); $^{13}$C NMR (126 MHz, Chloroform-d) δ 166.57, 157.71, 133.44, 131.70, 121.31, 121.22, 114.42, 69.46, 52.01, 41.71.

Methyl 3-(2-chloroethoxy)benzoate

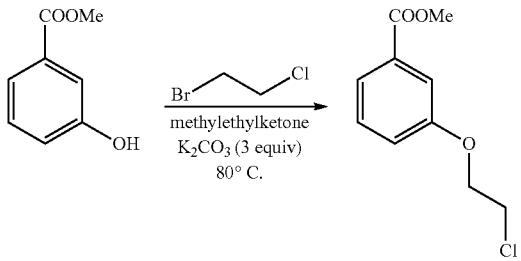

$^1$H NMR (500 MHz, Chloroform-d) δ 7.65 (dq, J=7.7, 1.3 Hz, 1H), 7.55 (dt, J=2.8, 1.5 Hz, 1H), 7.34 (td, J=7.9, 1.6 Hz, 1H), 7.11 (ddt, J=8.3, 2.7, 1.2 Hz, 1H), 4.26 (td, J=5.8, 1.8 Hz, 2H), 3.90 (d, J=1.5 Hz, 3H), 3.81 (td, J=5.8, 1.4 Hz, 2H); $^{13}$C NMR (126 MHz, Chloroform-d) δ 166.76, 158.18, 131.57, 129.59, 122.68, 120.15, 114.78, 68.19, 52.23, 41.84.

Methyl 4-(2-chloroethoxy)benzoate

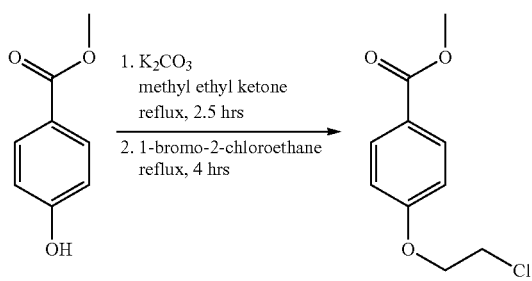

$^1$H NMR (500 MHz, DMSO-d$_6$) δ 7.93-7.83 (m, 2H), 7.09-7.00 (m, 2H), 4.35-4.27 (m, 2H), 4.00-3.92 (m, 2H), 3.81 (s, 3H). $^{13}$C NMR (126 MHz, DMSO-d$_6$) δ 166.3, 162.3, 131.7, 122.7, 115.0, 68.6, 52.3, 43.3, 40.5, 40.3, 40.2, 40.0, 39.8, 39.7, 39.5.

Example 25. General Procedure for Amination Via S$_N$2 Displacement 2-chloroethoxy benzoate (238 mmol, 1 eq), K$_2$CO$_3$ (1.64 g, 11.9 mmol, 5 eq), and KI (cat. amount) were added to a pressure tube with 5 mL of anhydrous DMF. To the reaction vessel, amine (7.15 mmol, 3 eq) was added. The reaction was then heated to 70° C. and allowed to run overnight. The reaction was then cooled to room temperature and reaction mixture was diluted with EtOAc (40 mL). Organic layer was washed with water (3×15 mL) and dried over anhydrous sodium sulfate, filtered and concentrated in vacuo. Pure product was obtained via column chromatography.

Methyl 2-(2-(diethylamino)ethoxy)benzoate

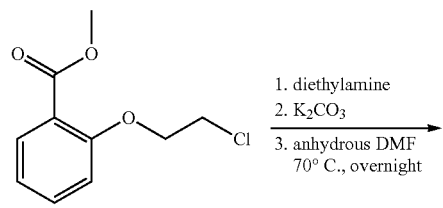

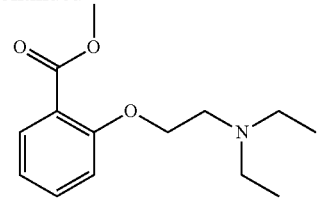

$^1$H NMR (500 MHz, Methanol-d$_4$) δ 7.71-7.67 (m, 1H), 7.50-7.45 (m, 1H), 7.11-7.06 (m, 1H), 6.99 (td, J=7.5, 1.0 Hz, 1H), 4.14 (t, J=5.6 Hz, 2H), 3.84 (s, 3H), 2.95 (t, J=5.6 Hz, 2H), 2.69 (q, J=7.2 Hz, 4H), 1.08 (t, J=7.2 Hz, 6H).

Methyl 2-(2-(pyrrolidin-1-yl)ethoxy)benzoate

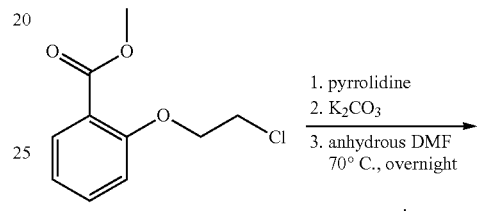

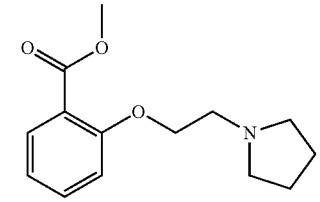

$^1$H NMR (500 MHz, DMSO-d$_6$) δ 7.60 (dd, J=7.7, 1.8 Hz, 1H), 7.49 (ddd, J=8.4, 7.3, 1.8 Hz, 1H), 7.13 (dd, J=8.4, 1.0 Hz, 1H), 6.99 (td, J=7.5, 1.0 Hz, 1H), 4.10 (t, J=5.8 Hz, 2H), 3.75 (s, 3H), 2.77 (t, J=5.8 Hz, 2H), 2.51 (ddt, J=5.4, 3.9, 1.9 Hz, 4H), 1.65 (p, J=3.2 Hz, 4H). $^{13}$C NMR (126 MHz, DMSO-d$_6$) δ 166.9, 157.8, 133.8, 131.0, 121.0, 120.6, 114.0, 68.6, 54.7, 54.5, 52.2, 40.5, 40.3, 40.2, 40.0, 39.8, 39.7, 39.5, 23.7.

Methyl 2-(2-(piperidin-1-yl)ethoxy)benzoate

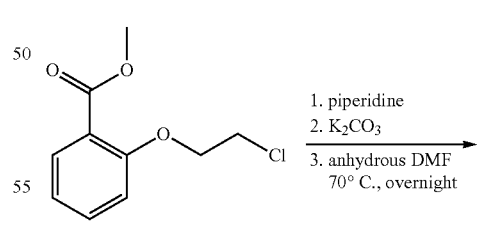

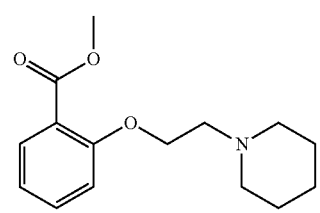

$^1$H NMR (500 MHz, DMSO-d$_6$) δ 7.59 (dd, J=7.7, 1.8 Hz, 1H), 7.48 (ddd, J=8.4, 7.4, 1.8 Hz, 1H), 7.13 (dd, J=8.5, 1.0

Hz, 1H), 6.98 (td, J=7.5, 1.0 Hz, 1H), 4.10 (t, J=5.8 Hz, 2H), 3.75 (s, 3H), 2.64 (t, J=5.8 Hz, 2H), 2.43 (d, J=5.8 Hz, 4H), 1.46 (p, J=5.6 Hz, 5H), 1.35 (q, J=6.3 Hz, 2H). $^{13}$C NMR (126 MHz, DMSO-$d_6$) δ 166.9, 157.8, 133.8, 131.0, 121.0, 120.6, 114.1, 67.7, 57.6, 54.9, 52.2, 40.5, 40.3, 40.2, 40.0, 39.8, 39.7, 39.5, 26.1, 24.3.

Methyl
2-(2-(4-methylpiperazin-1-yl)ethoxy)benzoate

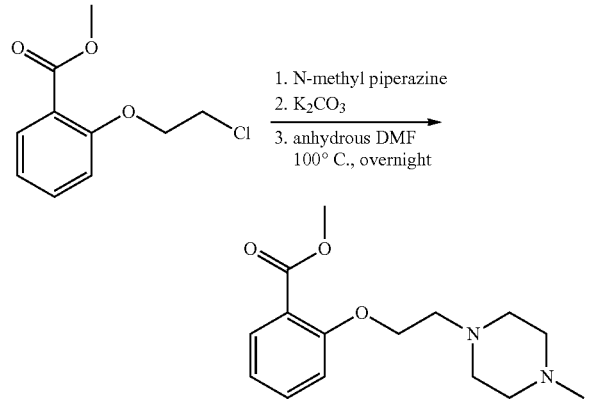

$^1$H NMR (500 MHz, DMSO-$d_6$) δ 7.60 (dd, J=7.7, 1.8 Hz, 1H), 7.49 (ddd, J=8.9, 7.4, 1.9 Hz, 1H), 7.13 (dd, J=8.5, 0.9 Hz, 1H), 6.99 (td, J=7.5, 1.0 Hz, 1H), 4.10 (t, J=5.7 Hz, 2H), 3.75 (s, 3H), 2.67 (t, J=5.7 Hz, 2H), 2.48 (p, J=1.9 Hz, 4H), 2.29 (s, 4H), 2.12 (s, 3H). $^{13}$C NMR (126 MHz, DMSO-$d_6$) δ 166.9, 157.8, 133.8, 131.0, 121.0, 120.6, 114.1, 67.7, 56.9, 55.3, 53.6, 52.6, 52.3, 46.2, 40.5, 40.3, 40.2, 40.0, 39.8, 39.6, 39.5.

Methyl 2-(2-morpholinoethoxy)benzoate

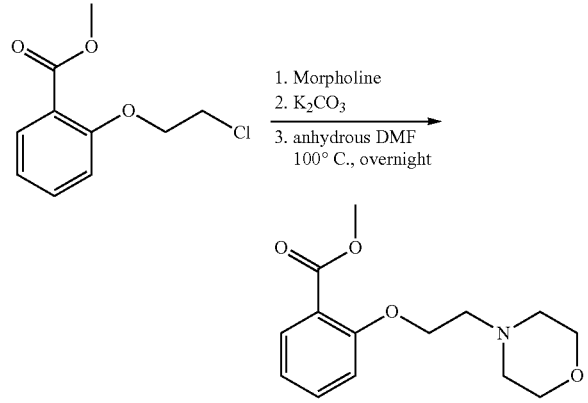

$^1$H NMR (500 MHz, DMSO-$d_6$) δ 7.60 (dd, J=7.6, 1.8 Hz, 1H), 7.49 (ddd, J=8.4, 7.4, 1.8 Hz, 1H), 7.14 (dd, J=8.4, 1.0 Hz, 1H), 6.99 (td, J=7.5, 1.0 Hz, 1H), 4.13 (t, J=5.6 Hz, 2H), 3.75 (s, 3H), 3.55 (t, J=4.7 Hz, 4H), 2.69 (t, J=5.7 Hz, 2H), 2.54-2.43 (m, 4H). $^{13}$C NMR (126 MHz, DMSO-$d_6$) δ 166.9, 157.7, 133.8, 131.0, 121.0, 120.7, 114.1, 67.6, 66.7, 57.3, 54.2, 52.3, 40.5, 40.3, 40.2, 40.0, 39.8, 39.7, 39.5.

Methyl
2-(2-(4-methylpiperidin-1-yl)ethoxy)benzoate

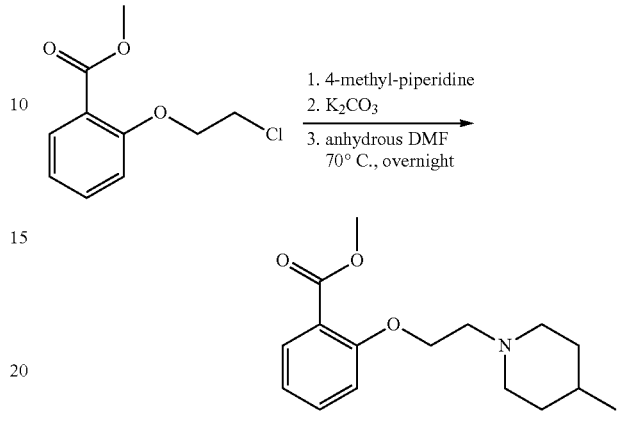

$^1$H NMR (500 MHz, Chloroform-d) δ 7.78-7.74 (m, 1H), 7.45-7.41 (m, 1H), 6.98-6.94 (m, 2H), 4.21 (t, J=6.0 Hz, 2H), 3.86 (s, 3H), 3.03 (dt, J=11.0, 2.8 Hz, 2H), 2.88 (t, J=6.0 Hz, 2H), 2.18 (td, J=11.7, 2.5 Hz, 2H), 1.67-1.59 (m, 2H), 1.44-1.35 (m, 1H), 1.35-1.23 (m, 3H), 0.92 (d, J=6.2 Hz, 3H). $^{13}$C NMR (126 MHz, Chloroform-d) δ 166.8, 158.2, 133.4, 131.6, 120.5, 120.4, 113.3, 77.3, 77.0, 76.8, 67.2, 57.3, 54.5, 51.9, 34.1, 30.4, 21.8.

Methyl
2-(2-(3,5-dimethylpiperidin-1-yl)ethoxy)benzoate

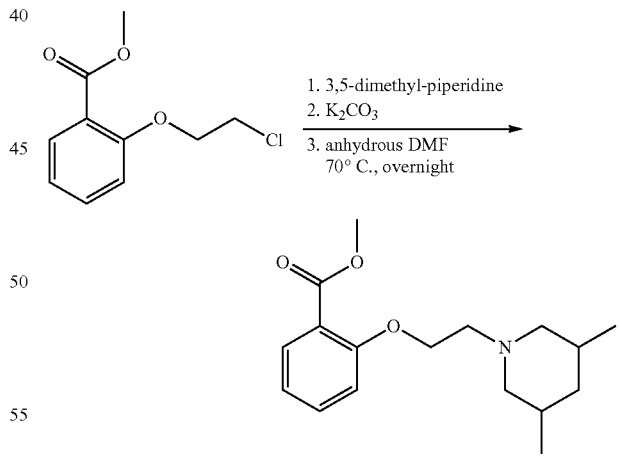

$^1$H NMR (500 MHz, Chloroform-d) δ 7.80-7.76 (m, 1H), 7.44 (dddd, J=8.4, 7.4, 3.7, 1.8 Hz, 1H), 7.00-6.95 (m, 2H), 4.26 (t, J=5.8 Hz, 2H), 3.87 (s, 3H), 3.04 (d, J=9.6 Hz, 2H), 2.98-2.89 (m, 2H), 1.87-1.69 (m, 5H), 0.96 (d, J=6.9 Hz, 1H), 0.87 (d, J=6.2 Hz, 6H), 0.61-0.51 (m, 1H). $^{13}$C NMR (126 MHz, Chloroform-d) δ 166.7, 158.0, 133.5, 131.6, 120.5, 113.4, 77.3, 77.0, 76.8, 66.8, 61.7, 57.1, 51.9, 41.5, 30.7, 19.5.

Methyl (S)-2-(2-(3-(dimethylamino)pyrrolidin-1-yl)ethoxy)benzoate

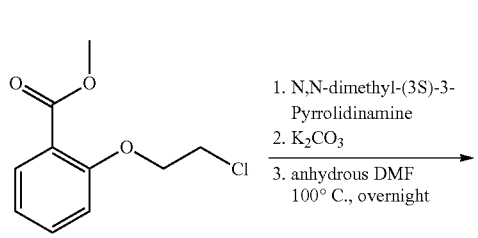

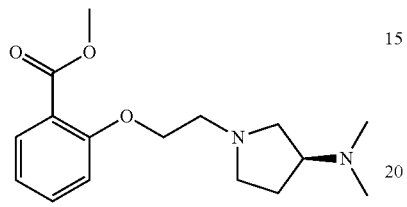

¹H NMR (500 MHz, DMSO-d₆) δ 7.62-7.57 (m, 1H), 7.51-7.46 (m, 1H), 7.12 (dd, J=8.5, 1.0 Hz, 1H), 6.98 (td, J=7.5, 1.0 Hz, 1H), 4.08 (t, J=5.7 Hz, 2H), 3.75 (s, 3H), 2.80-2.74 (m, 2H), 2.72 (t, J=5.7 Hz, 1H), 2.70-2.59 (m, 2H), 2.34 (dd, J=9.2, 6.9 Hz, 1H), 2.07 (s, 6H), 1.79 (dddd, J=12.5, 8.8, 7.7, 5.9 Hz, 1H), 1.55 (ddt, J=12.4, 8.6, 6.1 Hz, 1H). ¹³C NMR (126 MHz, DMSO-d₆) δ 166.8, 157.7, 133.8, 131.0, 121.0, 120.6, 114.0, 68.5, 65.6, 59.0, 54.6, 54.2, 52.2, 43.9, 40.5, 40.3, 40.1, 40.0, 39.8, 39.6, 39.5, 28.9.

Methyl (R)-2-(2-(3-(dimethylamino)pyrrolidin-1-yl)ethoxy)benzoate

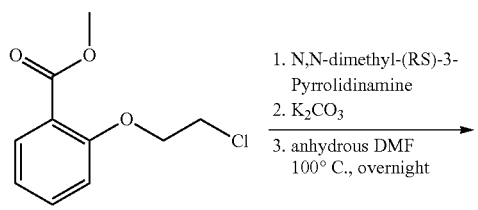

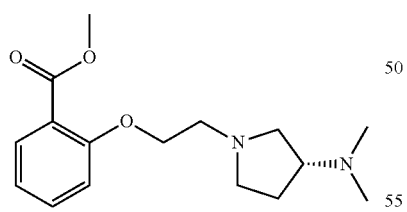

¹H NMR (500 MHz, Chloroform-d) δ 7.76 (dd, J=7.7, 1.8 Hz, 1H), 7.43 (ddd, J=8.4, 7.4, 1.8 Hz, 1H), 7.02-6.92 (m, 2H), 4.16 (t, J=5.8 Hz, 2H), 3.86 (s, 3H), 3.04-2.82 (m, 5H), 2.68 (td, J=9.1, 6.2 Hz, 1H), 2.57 (dd, J=9.4, 7.0 Hz, 1H), 2.27 (s, 6H), 2.02 (dddd, J=12.9, 8.8, 8.0, 6.2 Hz, 1H), 1.77 (ddt, J=12.9, 8.8, 5.8 Hz, 1H). ¹³C NMR (126 MHz, Chloroform-d) δ 166.7, 158.2, 133.4, 131.6, 120.5, 120.4, 113.3, 77.3, 77.0, 76.8, 68.2, 65.4, 59.0, 54.6, 54.1, 51.9, 43.6, 28.8.

Methyl 2-(2-(4-(dimethylamino)piperidin-1-yl)ethoxy)benzoate

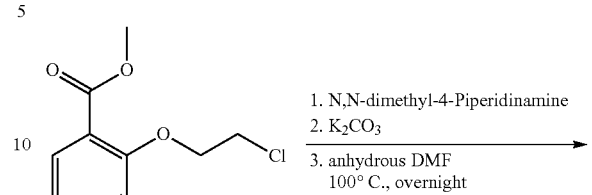

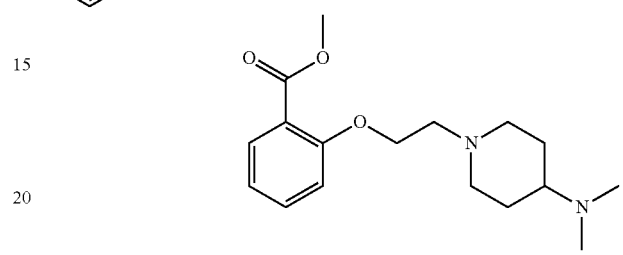

¹H NMR (500 MHz, Chloroform-d) δ 7.76 (dd, J=7.7, 1.8 Hz, 1H), 7.43 (ddd, J=8.4, 7.4, 1.8 Hz, 1H), 6.99-6.92 (m, 2H), 4.16 (t, J=5.9 Hz, 2H), 3.86 (s, 3H), 3.11-3.06 (m, 2H), 2.84 (t, J=5.9 Hz, 2H), 2.32 (s, 6H), 2.29-2.20 (m, 2H), 2.16 (td, J=12.0, 2.4 Hz, 2H), 1.83 (dq, J=12.4, 3.0 Hz, 3H), 1.58 (td, J=12.1, 3.8 Hz, 2H). ¹³C NMR (126 MHz, Chloroform-d) δ 166.8, 158.2, 133.4, 131.6, 120.4, 113.4, 77.3, 77.0, 76.8, 67.6, 62.2 56.9, 53.6, 51.9, 41.4, 41.3, 28.0, 27.8.

Example 26. General Procedure for Hydrolysis of Ester

A solution of methylbenzoate analog in a 2:1 THF:H₂O solution, 1 M NaOH (127.8 mg, 3.195 mmol, 5 eq) was stirred. After 22 hrs. additional 1M NaOH (127.8 mg, 3.195 mmol, 5 eq) was added. After 8 hrs, additional 1M NaOH (511.2 mg, 12.78 mmol, 20 eq) was added. The reaction then ran for 17 hrs. Once completed on TLC, the reaction was then concentrated, diluted with water, and acidified. The water was removed in vacuo resulting in a solid 2-(2-(diethylamino)ethoxy)benzoic Acid

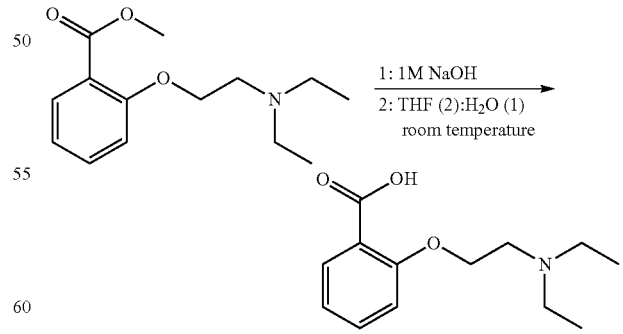

¹H NMR (500 MHz, DMSO-d₆) δ 7.67 (dd, J=7.6, 1.8 Hz, 1H), 7.52 (ddd, J=8.4, 7.4, 1.9 Hz, 1H), 7.15 (dd, J=8.5, 1.0 Hz, 1H), 7.04 (td, J=7.5, 0.9 Hz, 1H), 4.49-4.40 (m, 2H), 3.48 (dd, J=5.4, 4.0 Hz, 2H), 3.25 (d, J=7.5 Hz, 4H), 1.24 (t, J=7.2 Hz, 6H). ¹³C NMR (126 MHz, DMSO-d₆) δ 167.7, 156.9, 133.7, 131.4, 121.9, 121.4, 113.9, 63.9, 49.9, 47.6, 40.5, 40.3, 40.1, 40.0, 39.8, 39.6, 39.5, 9.1.

2-(2-morpholinoethoxy)benzoic Acid

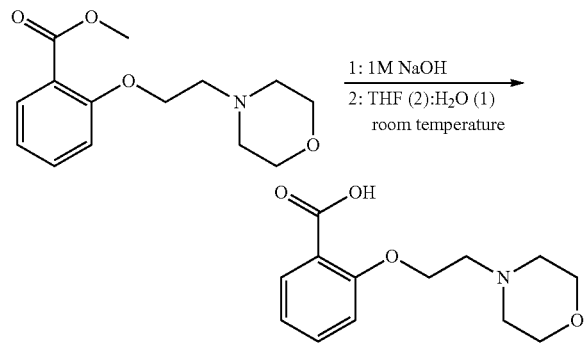

2-(2-(4-methylpiperidin-1-yl)ethoxy)benzoic Acid

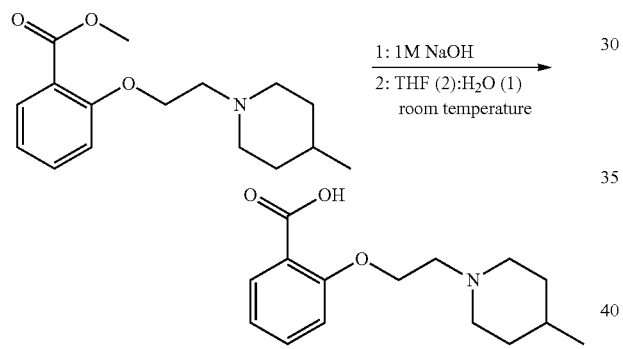

¹H NMR (500 MHz, DMSO-d₆) δ 7.65 (dd, J=7.7, 1.8 Hz, 1H), 7.53-7.48 (m, 1H), 7.14 (d, J=8.4 Hz, 1H), 7.03 (t, J=7.5 Hz, 1H), 4.50 (t, J=4.8 Hz, 2H), 3.65-3.48 (m, 3H), 3.43 (t, J=4.9 Hz, 4H), 3.06 (d, J=13.4 Hz, 2H), 1.73 (d, J=12.3 Hz, 2H), 1.63-1.47 (m, 3H), 0.90 (d, J=5.1 Hz, 3H). ¹³C NMR (126 MHz, DMSO-d₆) δ 167.6, 156.9, 133.7, 131.3, 122.0, 121.33, 114.0, 63.9, 55.2, 55.0, 40.5, 40.3, 40.1, 40.0, 39.8, 39.6, 39.5, 31.4, 28.4, 21.6.

2-(2-(3,5-dimethylpiperidin-1-yl)ethoxy)benzoic Acid

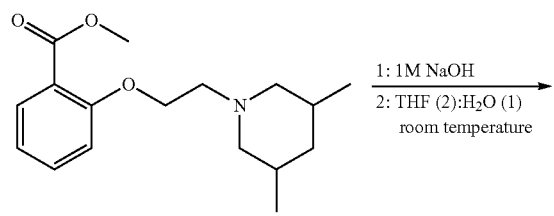

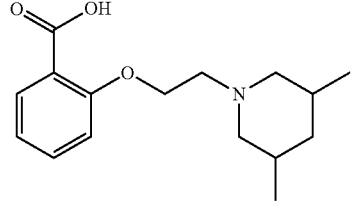

¹H NMR (500 MHz, DMSO-d₆) δ 7.69-7.65 (m, 1H), 7.51 (ddd, J=8.9, 7.4, 1.8 Hz, 1H), 7.16-7.12 (m, 1H), 7.03 (td, J=7.5, 0.9 Hz, 1H), 4.55-4.48 (m, 2H), 3.55-3.46 (m, 2H), 3.44 (q, J=4.7 Hz, 3H), 2.58 (t, J=12.1 Hz, 2H), 2.05 (ddh, J=15.9, 7.3, 3.8 Hz, 2H), 1.75-1.67 (m, 1H), 0.87 (dd, J=6.7, 3.4 Hz, 6H), 0.75 (q, J=12.3 Hz, 1H). ¹³C NMR (126 MHz, DMSO-d₆) δ 167.6, 156.8, 133.7, 131.4, 121.8, 121.4, 121.3, 113.9, 113.9, 63.8, 58.2, 55.5, 39.13, 28.7, 18.8.

Example 27. General Procedure for Preparation of Fluorenyl Compounds

To a solution of 1-(9H-fluoren-9-yl) piperazine (75 mg, 0.3 mmol, 1 eq.) and HBTU (125.1 mg, 0.33 mmol, 1.1 eq.) in DCM, DIPEA (116.1 mg, 0.9 mmol, 3 eq.) was added. Upon addition of HBTU, 2-(2-amino ethoxy)benzoic acid (0.3 mmol, 1 eq) was added. The reaction was then allowed to run overnight at room temperature. The reaction was then cooled to room temperature and reaction mixture was dilute with EtOAc (40 mL). Organic layer was washed with water (3×15 mL) and dried over anhydrous sodium sulfate, filtered and concentrated in vacuo. Pure compound was obtained via column chromatography.

(4-(9H-Fluoren-9-yl)piperazin-1-yl)(2-(2-(4-methylpiperidin-1-yl) ethoxy)phenyl)methanone

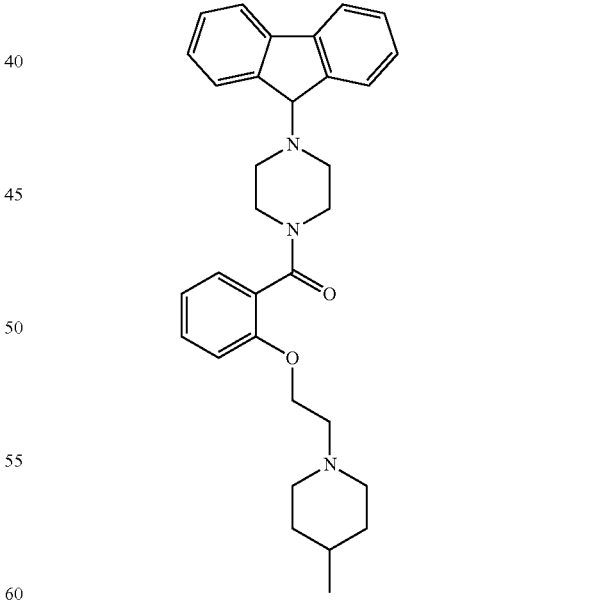

HSMD01

¹H NMR (500 MHz, Methanol-d₄) δ 7.73 (d, J=7.5 Hz, 2H), 7.64 (d, J=7.5 Hz, 2H), 7.42-7.36 (m, 3H), 7.31 (td, J=7.5, 1.1 Hz, 2H), 7.17 (dd, J=7.5, 1.7 Hz, 1H), 7.09 (d, J=8.4 Hz, 1H), 7.04 (t, J=7.5 Hz, 1H), 4.93 (s, 1H), 4.29 (t, J=5.3 Hz, 2H), 3.73 (dt, J=11.0, 5.2 Hz, 2H), 3.28-3.16 (m, 4H), 3.11-3.05 (m, 2H), 2.68 (q, J=6.2 Hz, 2H), 2.61-2.51 (m, 4H), 1.75 (dt, J=14.2, 2.8 Hz, 2H), 1.59-1.51 (m, 1H), 1.41-1.32 (m, 2H), 0.97 (d, J=6.5 Hz, 3H); $^{13}$C NMR (126 MHz, Methanol-d$_4$) δ 168.7, 154.0, 143.1, 141.0, 130.80, 128.1, 127.3, 126.9, 125.6, 125.3, 121.4, 119.5, 112.6, 69.5, 56.2, 53.8, 53.5, 48.9, 48.4, 42.2, 32.1, 20.3.

(4-(9H-Fluoren-9-yl)piperazin-1-yl)(3-(2-morpholinoethoxy)phenyl)methanone

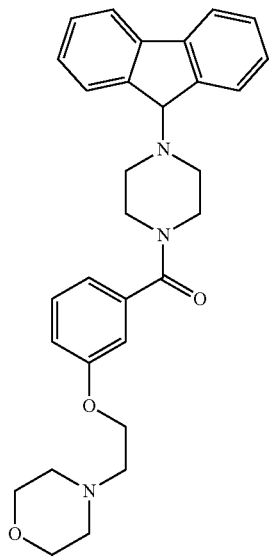

HSMD02

$^1$H NMR (500 MHz, Methanol-d$_4$) δ 7.74 (d, J=7.5 Hz, 2H), 7.65 (d, J=7.5 Hz, 2H), 7.38 (td, J=7.7, 2.8 Hz, 3H), 7.30 (t, J=7.4 Hz, 2H), 7.09 (dd, J=8.2, 2.6 Hz, 1H), 7.02-6.96 (m, 2H), 4.96 (s, 1H), 4.36 (t, J=4.9 Hz, 2H), 3.90 (s, 6H), 3.75 (s, 2H), 3.58 (d, J=26.8 Hz, 2H), 3.45-3.33 (m, 5H), 2.78 (s, 2H), 2.48 (s, 2H). $^{13}$C NMR (126 MHz, Methanol-d$_4$) δ 170.39, 157.85, 143.00, 141.05, 136.91, 136.54, 129.75, 128.16, 126.88, 125.63, 119.82, 119.49, 115.88, 112.97, 63.70, 56.10, 52.37, 48.85, 48.54, 48.22.

(4-(9H-Fluoren-9-yl)piperazin-1-yl)(2-(2-morpholinoethoxy)phenyl)methanone

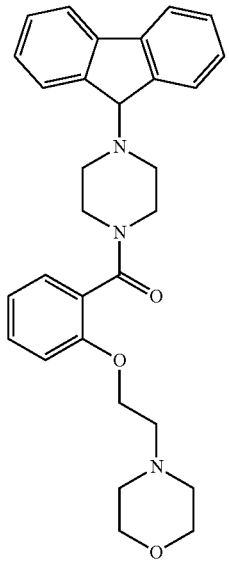

HSMD03

$^1$H NMR (500 MHz, Methanol-d$_4$) δ 7.73 (d, J=7.5 Hz, 2H), 7.64 (d, J=7.7 Hz, 2H), 7.37 (td, J=8.6, 4.3 Hz, 3H), 7.31 (dt, J=9.3, 4.5 Hz, 2H), 7.16 (d, J=7.4 Hz, 1H), 7.06-6.96 (m, 2H), 4.92-4.93 (m, 1H), 4.14 (h, J=5.4 Hz, 2H), 3.76-3.67 (m, 6H), 3.19-3.15 (m, 2H), 2.76 (dd, J=11.5, 5.7 Hz, 4H), 2.68-2.38 (m, 6H).

The invention claimed is:

1. A compound having the structure of

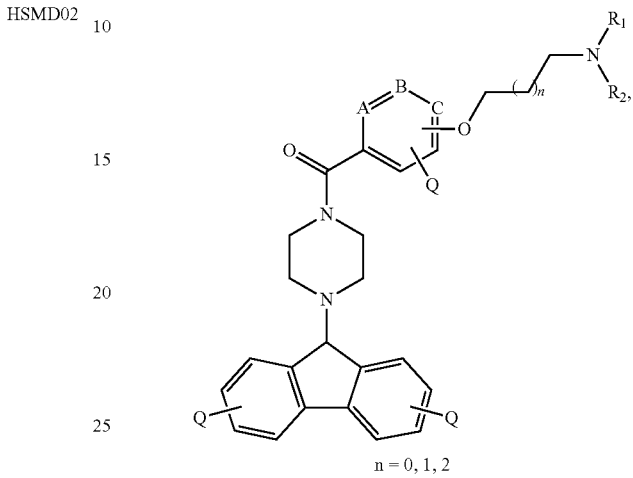

n = 0, 1, 2 or a pharmaceutically acceptable salt thereof,
wherein R$_1$ and R$_2$, independently, are hydrogen, an alkyl, heteroalkyl, acyclic alkyl, or cyclic heteroalkyl;
Q represents, independently, a substituent selected from the group consisting of hydrogen, halogen (F, Cl, Br, I), or CN; and
A, B or C=Carbon or N, wherein A, B, and C are not N at the same time.

2. The compound according to claim 1, wherein said compound is selected from the group consisting of

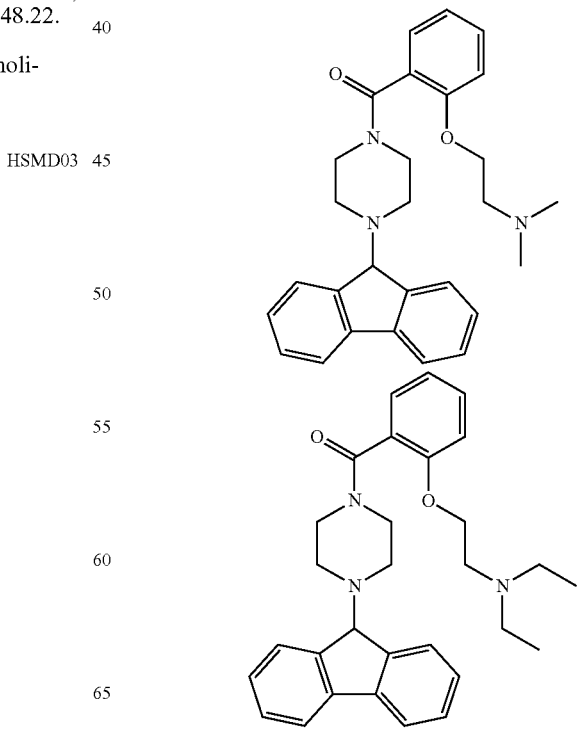

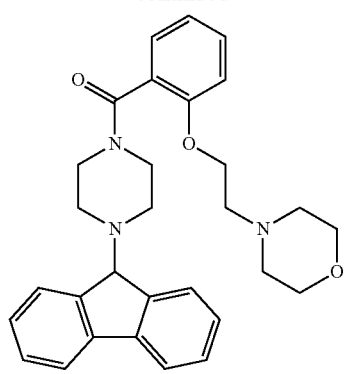
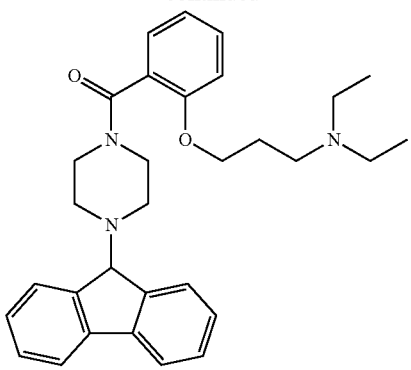
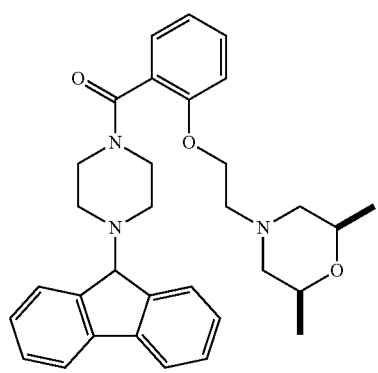
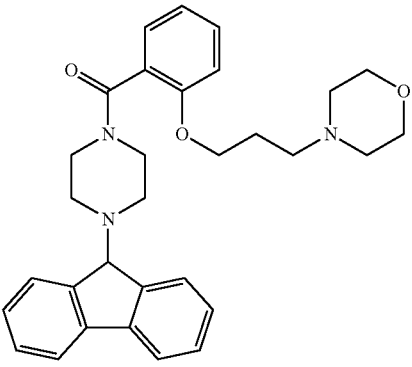
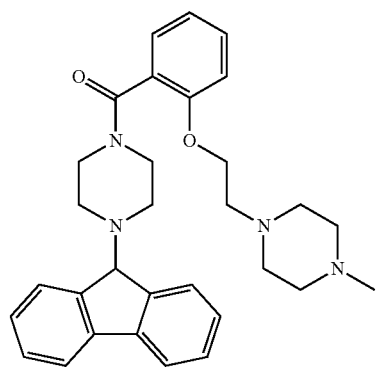
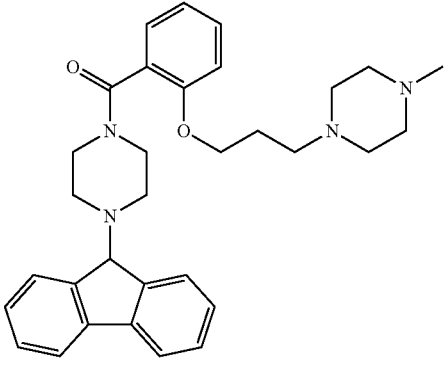
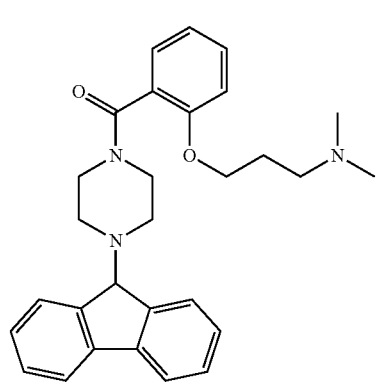
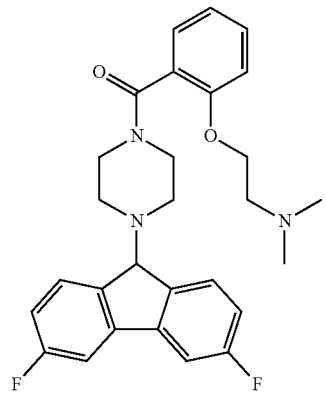

49
-continued
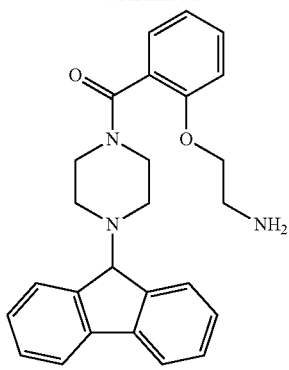
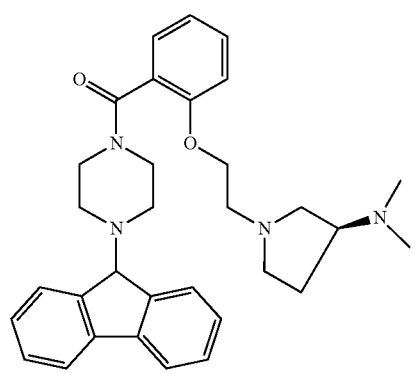
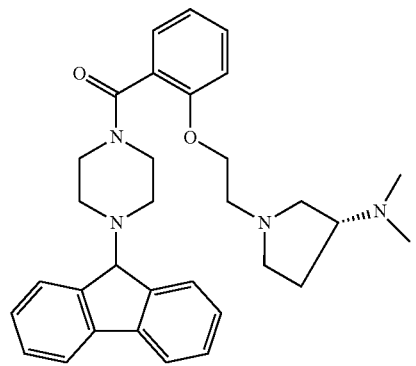
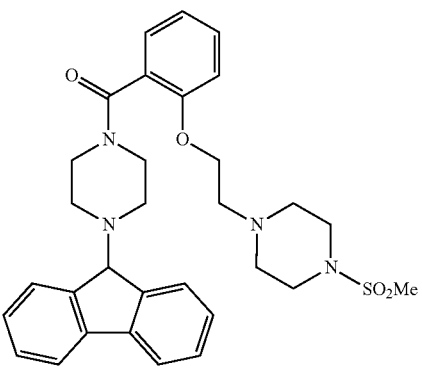
50
-continued
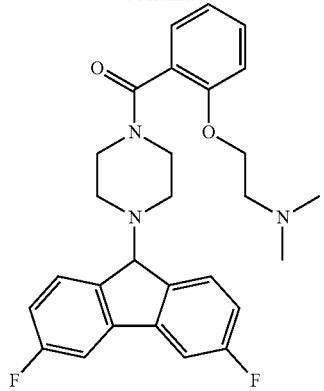
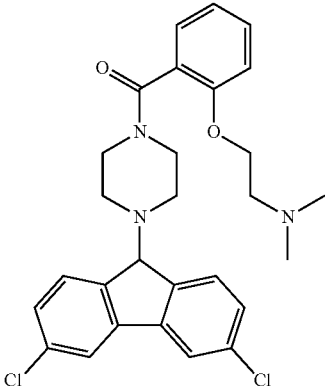
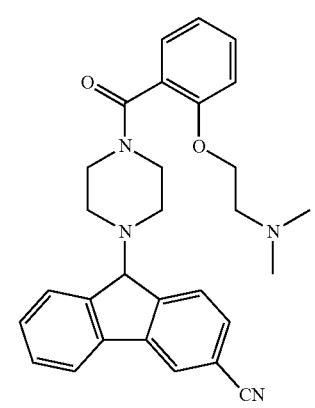
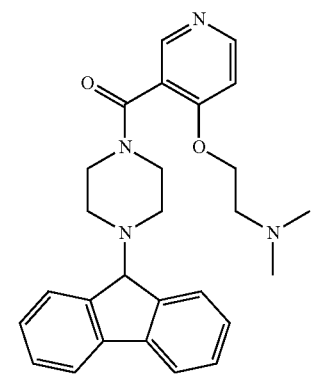

51
-continued
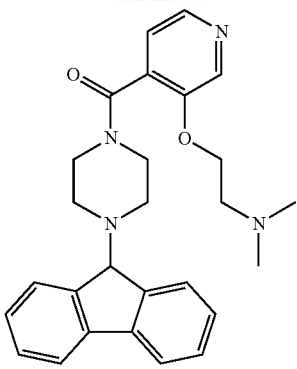
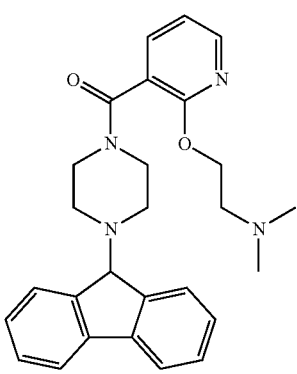
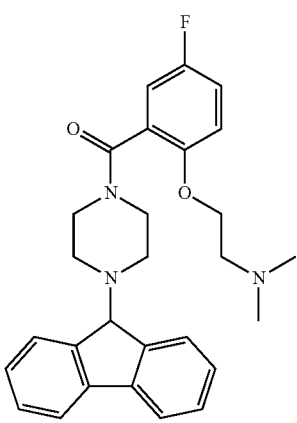
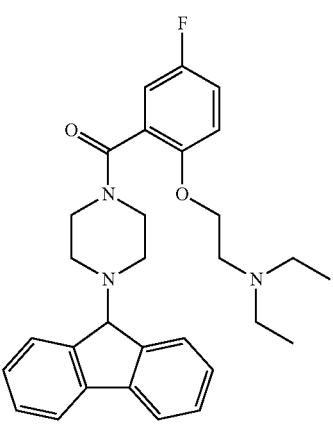
52
-continued
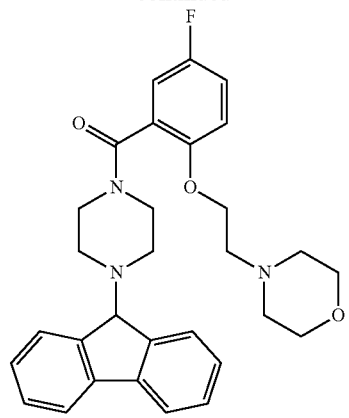
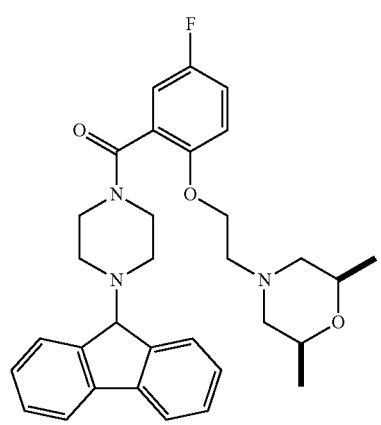
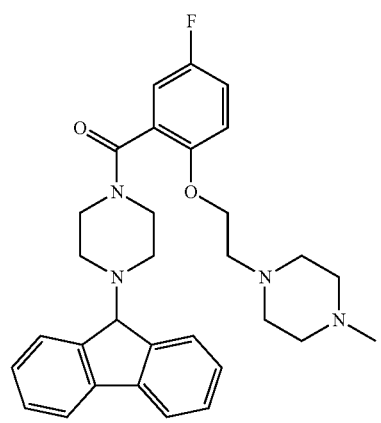

53
-continued
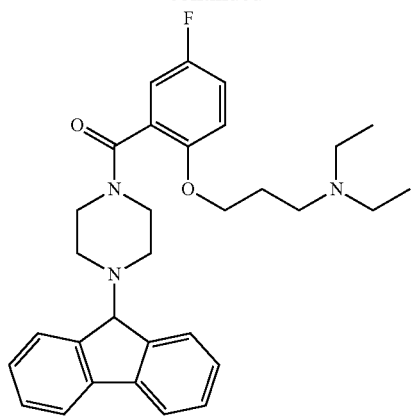
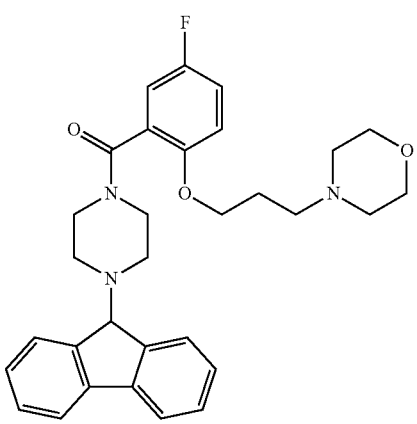
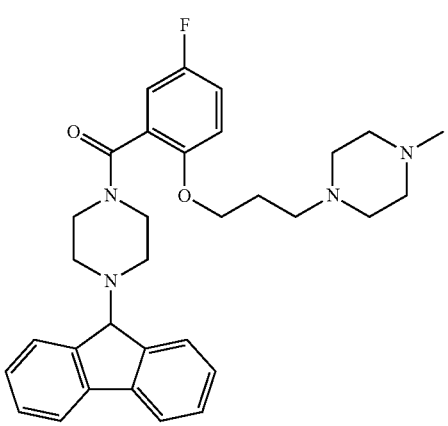
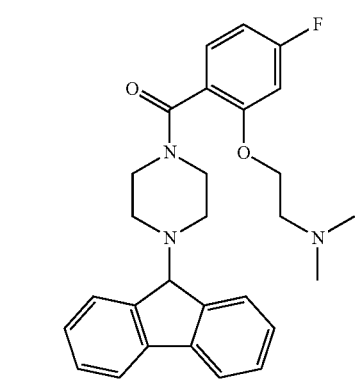
54
-continued
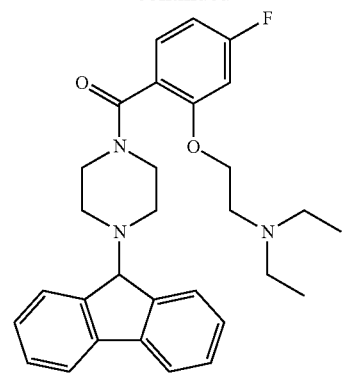
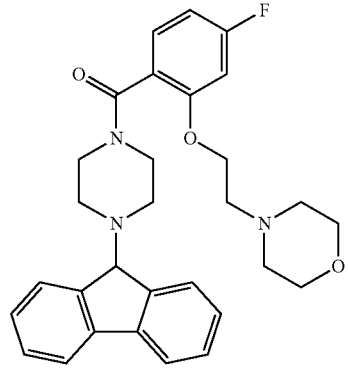
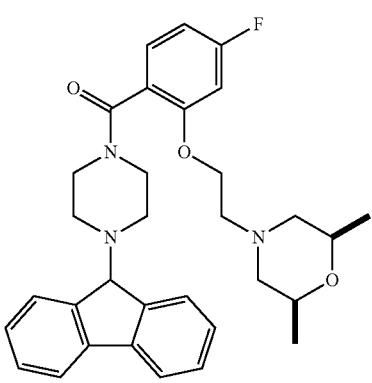
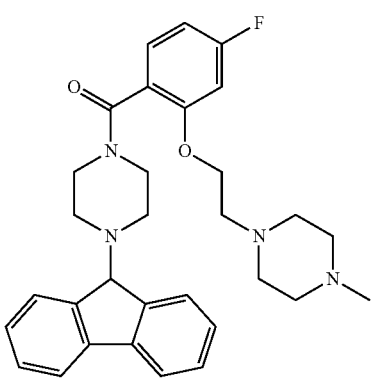

-continued
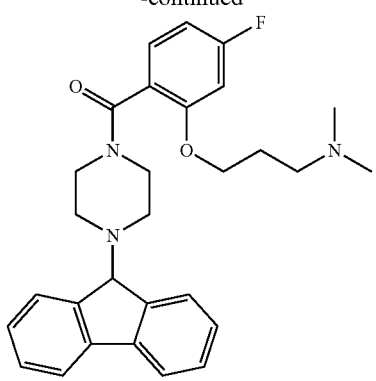
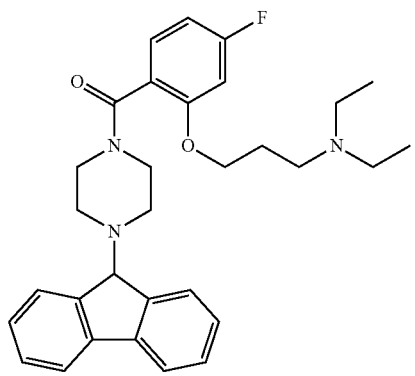
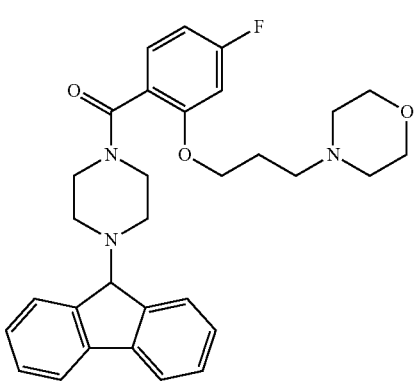
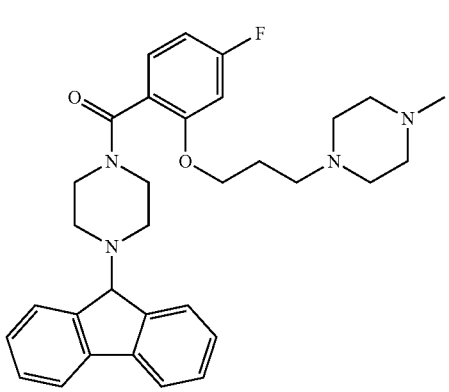
-continued
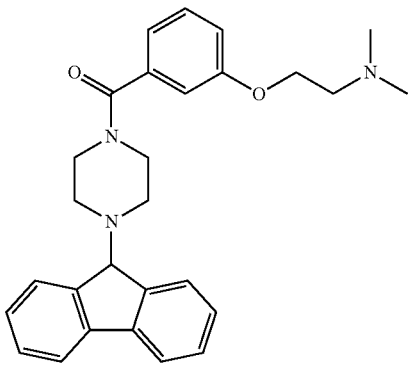
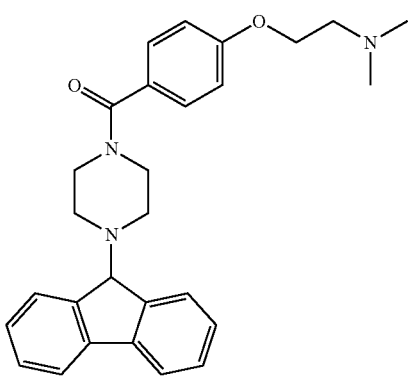
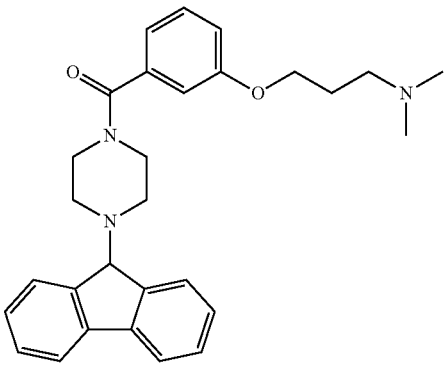
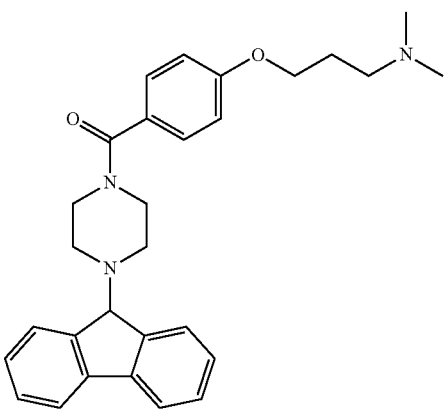

57
-continued
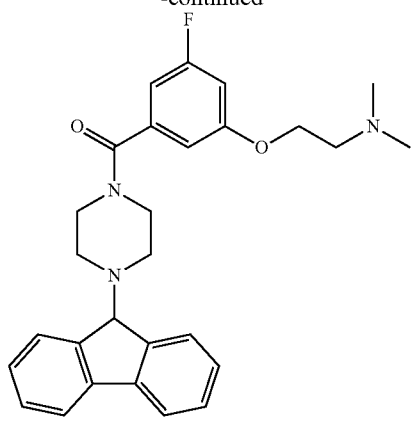
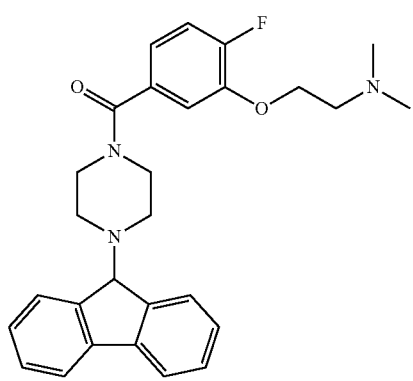
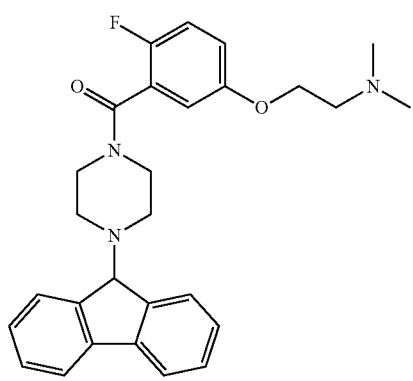
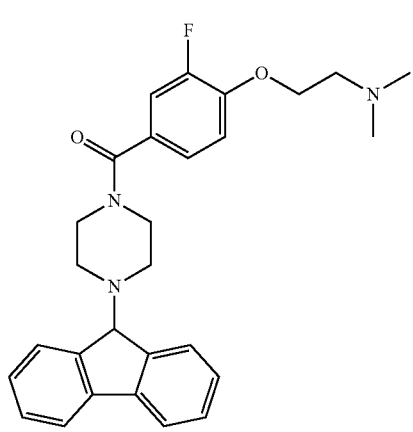
58
-continued
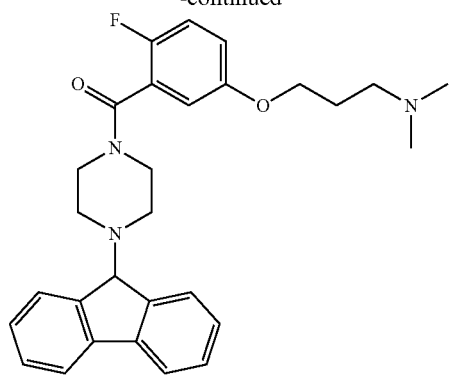
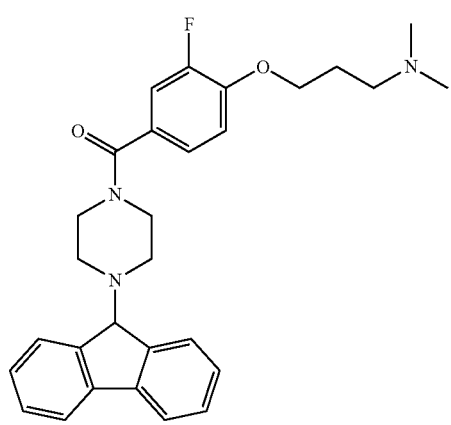
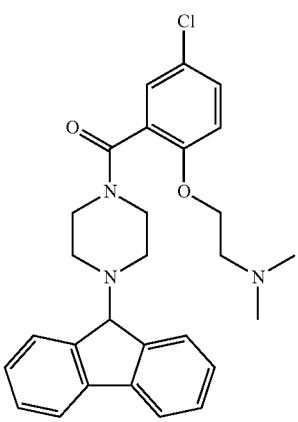
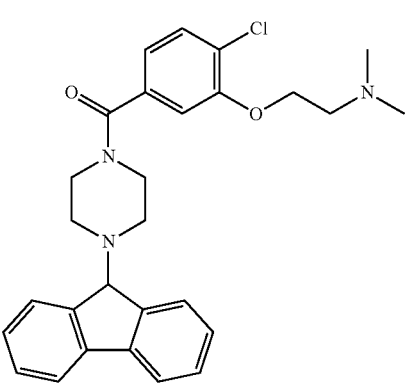

-continued

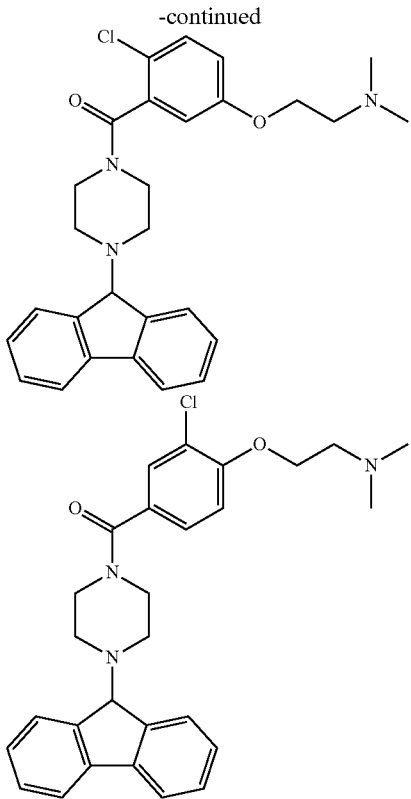

-continued

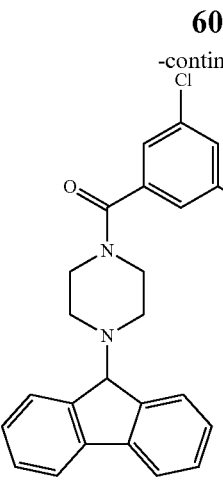

3. A pharmaceutical composition comprising a compound, or a pharmaceutically acceptable salt thereof, according to claim 1, together with one or more diluents, excipients or carriers.

4. A method for treating a patient with osteoarthritis or prostate cancer comprising the step of administering a therapeutically effective amount of the compound according to claim 1 to the patient in need of treatment of said osteoarthritis or prostate cancer.

* * * * *